US008528634B2

(12) United States Patent
Hendrickson et al.

(10) Patent No.: US 8,528,634 B2
(45) Date of Patent: *Sep. 10, 2013

(54) METHOD OF IMPROVING OIL RECOVERY FROM AN OIL RESERVOIR USING AN ENRICHED ANAEROBIC STEADY STATE MICROBIAL CONSORTIUM

(75) Inventors: Edwin R. Hendrickson, Hockessin, DE (US); Abigail K. Luckring, West Chester, PA (US); Sharon Jo Keeler, Bear, DE (US); Michael P. Perry, Landenberg, PA (US); Eric R. Choban, Williamstown, NJ (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 462 days.

This patent is subject to a terminal disclaimer.

(21) Appl. No.: 12/704,589

(22) Filed: Feb. 12, 2010

(65) Prior Publication Data

US 2010/0212888 A1    Aug. 26, 2010

Related U.S. Application Data

(60) Provisional application No. 61/154,498, filed on Feb. 23, 2009.

(51) Int. Cl.
*E21B 43/22* (2006.01)

(52) U.S. Cl.
USPC ........................................................ 166/246

(58) Field of Classification Search
None
See application file for complete search history.

(56) References Cited

U.S. PATENT DOCUMENTS

| | | | |
|---|---|---|---|
| 5,044,435 A | 9/1991 | Sperl et al. | |
| 5,858,766 A | 1/1999 | Premuzic et al. | |
| 6,543,535 B2* | 4/2003 | Converse et al. | 166/246 |
| 6,852,234 B2 | 2/2005 | Breitenbeck | |
| 7,124,817 B1 | 10/2006 | Sunde | |
| 7,172,688 B2 | 2/2007 | Petersen | |
| 7,201,804 B2 | 4/2007 | Tunnicliffe et al. | |
| 7,442,313 B2 | 10/2008 | Kerfoot | |
| 7,449,429 B2 | 11/2008 | Goldman | |
| 7,465,395 B2 | 12/2008 | Carbonell et al. | |
| 7,473,672 B2 | 1/2009 | Kotlar et al. | |
| 7,708,065 B2 | 5/2010 | Hendrickson et al. | |
| 7,740,063 B2* | 6/2010 | Fallon et al. | 166/246 |
| 7,977,056 B2* | 7/2011 | Toledo et al. | 435/6.13 |
| 2004/0244969 A1* | 12/2004 | Kotlar et al. | 166/246 |
| 2007/0092930 A1 | 4/2007 | Lal et al. | |
| 2007/0181300 A1* | 8/2007 | Busche et al. | 166/246 |
| 2009/0082227 A1 | 3/2009 | Hnatow et al. | |

FOREIGN PATENT DOCUMENTS

WO    2010037000 A1    4/2010

OTHER PUBLICATIONS

Roling, Wilfred et al., Bacterial Community Dynamics and Hydrocarbon Degradation during a Field-Scale Evaluation of Bioremediation on a Mudflat Beach Contaminated with Buried Oil, Applied and Environmental Microbiology, May 2004, pp. 2603-2613, vol. 70, No. 5.
Vazquez, S. et al., Bacterial Community Dynamics during Bioremediation of Diesel Oil-Contaminated Antarctic Soil, Microbial Ecology, 2009, pp. 598-610, vol. 57, No. 4.
Watanabe, Kazuya, Microorganisms relevant to bioremediation, Current Opinion in Biotechnology, Jun. 2001, pp. 237-241, vol. 12, No. 3.
Almeida, P. F. et al., Selection and Application of Microorganisms to Improve Oil Recovery, Engineering in Life Sciences, 2004, pp. 319-325, vol. 4, No. 4.
Beristain-Cardoso, Ricardo et al., Phenol and sulfide oxidation in a denitrifying biofilm reactor and its microbial community analysis, Process Biochemistry, 2009, pp. 23-28, vol. 44.
Breinig, Sabine et al., Genes Involved in Anaerobic Metabolism of Phenol in the Bacterium Thauera aromatica, Journal of Bacteriology, Oct. 2000, pp. 5849-5863, vol. 182, No. 20.
Chen, Chuan et al., Functional consortium for denitrifying sulfide removal process, Applied Microbiology Biotechnology, 2010, pp. 353-358, vol. 86.
Farhadian, Mehrdad et al., in situ bioremediation of monoaromatic pollutants in groundwater: A review, Bioresource Technology, 2008, pp. 5296-5308, vol. 99.
Foght, Julia, Anaerobic Biodegradation of Aromatic Hydrocarbons: Pathways and Prospects, Journal of Molecular Microbiology and Biotechnology, Jul. 28, 2008, pp. 93-120, vol. 15.
Jiang, Xin et al., Bacterial Diversity of Active Sludge in Wastewater Treatment Plant, Earth Science Frontiers, 2008, pp. 163-168, vol. 15, No. 6.
Mechichi, Tahar et al., Anaerobic degradation of methoxylated aromatic compounds by *Clostridium methoxybenzovorans* and a nitrate-reducing bacterium *Thauera* sp. Strain Cin3,4, International Biodeterioration & Biodegradation, 2005, pp. 224-230, vol. 56.
Song, Bongkeun et al., Characterization of halobenzoate-degrading, denitrifying Azoarcus and Thauera isolates and description of *Thauera chlorobenzoica* sp. nov., International Journal of Systematic and Evolutionary Microbiology, 2001, pp. 589-602, vol. 51.
Song, Bongkeun et al., Characterization of bacterial consortia capable of degrading 4-chlorobenzoate and 4-bromobenzoate under denitrifying conditions, FEMS Microbiology Letters, 2002, pp. 183-188, vol. 213.
Song, Bongkeun et al., Nitrite reductase genes in halobenzoate degrading denitrifying bacteria, FEMS Microbiology Ecology, 2003, pp. 349-357, vol. 43.
Thomsen, Trine Rolighed et al., Ecophysiology of abundant denitrifying bacteria in activated sludge, FEMS Microbiology Ecology, 2007, pp. 370-382, vol. 60.
International Search Report and Written Opinion of corresponding PCT/US2010/024516 mailed Oct. 22, 2010.

(Continued)

Primary Examiner — Zakiya W Bates
Assistant Examiner — Silvana Runyan
(74) Attorney, Agent, or Firm — Scully, Scott, Murphy & Presser, P.C.

(57) ABSTRACT

The present disclosure relates to developing an enriched steady state microbial consortium capable of modifying crude oil components of an oil reservoir under anaerobic denitrifying conditions. The steady state consortium may be used to improve oil recovery.

11 Claims, 6 Drawing Sheets

(56) References Cited

OTHER PUBLICATIONS

Figure 1:
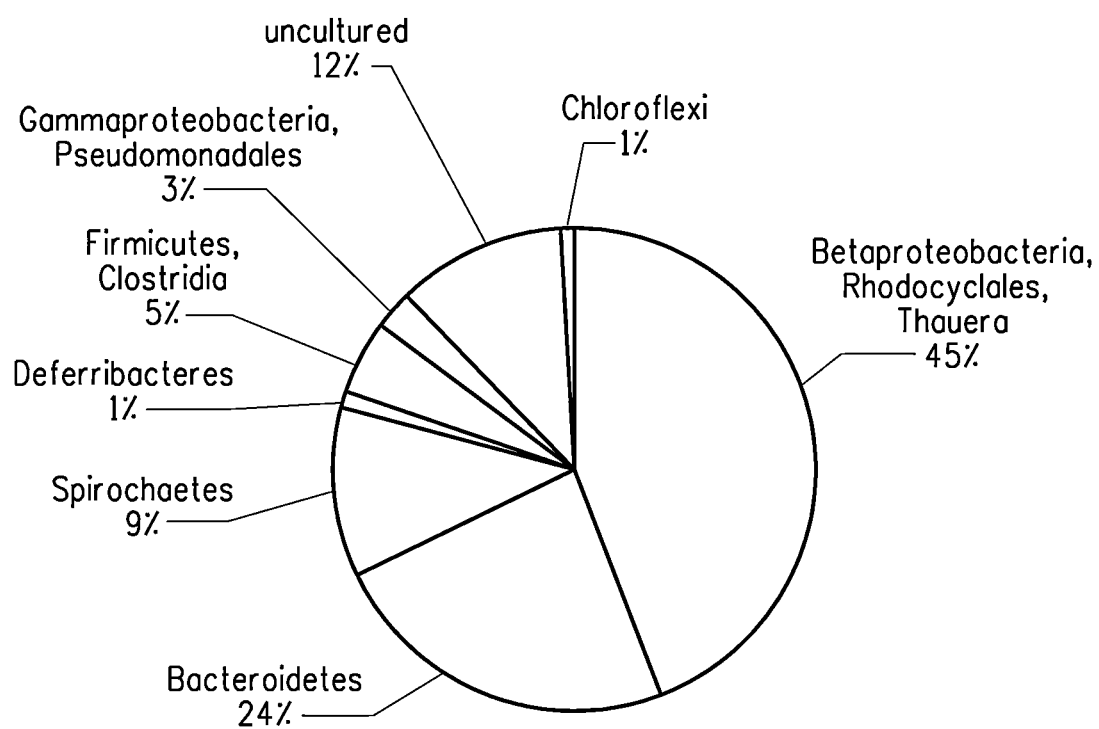

Hubert et al., "Oil field souring control by nitrate-reducing *Sulfurospirillum* spp. that outcompete sulfate-reducing bacteria for organic electron donors", Applied and Environmental Microbiology, American Society for Microbiology, vol. 73, No. 8, Apr. 1, 2007, pp. 2644-2652.

Hubert et al., "Containment of biogenic sulfide production in continuous up-flow packed-bed bioreactors with nitrate or nitrite", Biotechnology Progress, vol. 19, No. 2, Mar. 2003, pp. 338-345.

Bell et al., "Anaerobic degradation of oil hydrocarbons by sulfate-reducing and nitrate-reducing bacteria", Microbial Biosystems—New Frontiers: Proceedings of the $8^{th}$ International Symposium on Microbial Ecology, Halifax, Canada, Aug. 9-14, 1998, Atlantic Canada Society for Microbial Ecology, Halifax, Canada, pp. 1-9.

Rempel et al., "Dynamics of corrosion rates associated with nitrite or nitrate mediated control of souring under biological conditions simulating an oil reservoir", Journal of Industrial Microbiology & Biotechnology; Official Journal of the Society for Industrial Microbiology, Springer, Berlin, DE, vol. 33, No. 10, Jun. 7, 2006, pp. 878-886.

Khire et al., "Microbially enhanced oil recovery (MEOR), Part 1, Importance and mechanism of MEOR", Enzyme and Microbial Technology, Stoneham, MA, vol. 16, No. 2, Feb. 1, 1994, pp. 170-172.

Khire et al., "Microbially enhanced oil recovery (MEOR), Part 2, Microbes and the subsurface environment for MEOR", Enzyme and Microbial Technology, Stoneham, MA, vol. 16, No. 3, Mar. 1, 1994, pp. 258-259.

Smith, "MEOR screening criteria fit 27% of US oil reservoirs", Oil and Gas Journal, Pennwell, Houston, TX, vol. 89, No. 15, Apr. 15, 1991, pp. 56-59.

Nelson et al., "Stripper well production increased with MEOR treatment", Oil and Gas Journal, Pennwell, Houston, TX, vol. 89, No. 11, Mar. 18, 1991 pp. 114, 116-118.

Kianipey, S. A. et al., Mechanisms of Oil Displacement by Microorganisms, $61^{st}$ Annual Technical Conference and Exhibition of the Society of Petroleum Engineers, SPE 15601, Oct. 5-8, 1986, New Orleans, LA, pp. 1-13.

Brown, L. R. et al., Slowing Production Decline and Extending the Economic Life of an Oil Field: New MEOR Technology, SPE/DOE Improved Oil Recovery Symposium, SPE 59306, Apr. 3-5, 2000, Tulsa, OK, pp. 1-16.

Sunde, Egil et al., Aerobic Microbial Enhanced Oil Recovery for Offshore Use, SPE/DOE Symposium on Enhanced Oil Recovery, SPE/DOE 24204, Apr. 22-24, 1992, Tulska, OK, pp. 497-502.

Kowalewski, E. et al., Microbial improved oil recovery—bacterial induced wettability and interfacial tension effects on oil production, Journal of Petroleum Science & Engineering, 2006, pp. 275-286, vol. 52.

Office Action mailed Sep. 15, 2009, in co-pending U.S. Appl. No. 12/194,749.

Office Action mailed Mar. 9, 2009, in co-pending U.S. Appl. No. 12/240,205.

\* cited by examiner

METHOD OF IMPROVING OIL RECOVERY FROM AN OIL RESERVOIR USING AN ENRICHED ANAEROBIC STEADY STATE MICROBIAL CONSORTIUM

This Application claims the benefit of U.S. Provisional Patent Application 61/154,498 filed Feb. 23, 2009.

FIELD OF INVENTION

This disclosure relates to the field of environmental microbiology and modification of heavy crude oil properties using microorganisms that anaerobically modify the physiochemical properties of crude oil and/or a reservoir environment resulting in enhanced recovery of the crude oil.

BACKGROUND OF THE INVENTION

The challenge to meet the ever increasing demand for oil includes increasing crude oil recovery from heavy oil reservoirs. This challenge has resulted in expanding efforts to develop alternative cost efficient oil recovery processes (Kianipey, S. A. and Donaldson, E. C. $61^{st}$ Annual Technical Conference and Exhibition, New Orleans, La., USA, Oct. 5-8, 1986). Heavy hydrocarbons in the form of petroleum deposits and oil reservoirs are distributed worldwide. These oil reservoirs are measured in the hundreds of billions of recoverable barrels. Because heavy crude oil has a relatively high viscosity, it is essentially immobile and cannot be easily recovered by conventional primary and secondary means.

Microbial Enhanced Oil Recovery (MEOR) is a methodology for increasing oil recovery by the action of microorganisms (Brown, L. R., et al., SPE 59306, SPE/DOE Improved Oil Recovery Symposium, Oklahoma, Apr. 3-5, 2000). MEOR research and development is an ongoing effort directed at discovering techniques to use microorganisms to modify crude oil properties to benefit oil recovery (Sunde. E., et al., SPE 24204, SPE/DOE $8^{th}$ Symposium on enhanced Oil Recovery, Tulsa, Okla., USA, Apr. 22-24, 1992).

In MEOR processes, useful microbes are typically hydrocarbon-utilizing, non-pathogenic microorganisms, which use hydrocarbons as their energy source to grow or excrete natural bio-products such as alcohols, gases, acids, surfactants and polymers. These bio-products change the physio/chemical properties of the crude oil and stimulate changes in the oil-water-rock interactions to improve oil recovery.

The positive effects of the MEOR technology in a reservoir include: 1) altering the permeability of the subterranean formation to improve water sweep efficiency; (2) producing biosurfactants to decrease surface and interfacial tensions; (3) mediating changes in wettability; (4) producing polymers which facilitate mobility of petroleum; and (5) generating gases (predominantly $CO_2$), increasing formation pressure and reducing oil viscosity thus promoting and re-establishing the gas drive in the reservoir. The combined effects of these bio-products decrease the capillary forces acting between the oil, the water and the rock, releasing the trapped oil.

Methods for identifying microorganisms useful in MEOR processes previously described require identification of the consortium of microorganisms in the samples drawn from an oil well or the sample under specific conditions with a defined nutrient medium in the presence of anaerobic gas mixtures (U.S. Patent Application No. 200710092930A1). A process for stimulating the in situ activity of a microbial consortium to produce methane for oil was described in U.S. Pat. No. 6,543,535B2. Such processes are time consuming and labor-intensive. Thus, there is a need for developing methods to: 1) develop a steady state population of consortium of microorganisms that can grow in or on oil under anaerobic denitrifying conditions; 2) identify the members of the steady state consortium for properties that might be useful in oil modification and/or interactions and 3) use said steady state consortium of microorganisms, in a cost-effective way, to improve oil recovery under anaerobic conditions.

SUMMARY ON THE INVENTION

A method for enhancing oil recovery from an oil reservoir using an enriched anaerobic steady state consortium of microorganisms is provided. The method includes obtaining environmental samples comprising indigenous microbial populations exposed to crude oil and enriching said populations per an enrichment protocol. The enrichment protocol employs a chemostat bioreactor to provide a steady state population. The steady state population may be characterized by using phylogenetic DNA sequence analysis techniques, which include 16S rDNA profiling and/or DGGE fingerprint profiling as described herein. The steady state population is further characterized as an enriched consortium comprising microbial constituents having relevant functionalities for improving oil recovery. The steady state enriched consortium may grow in situ, under reservoir conditions, using one or more electron acceptors and the reservoir's crude oil as the carbon source for microbial enhancement of oil recovery. The steady state consortium may be used with other microorganisms to enhance oil recovery in reservoirs or wells with analogous reservoir conditions of the selected/targeted wells.

In one aspect, a method for enhancing oil recovery from a target oil reservoir using an enriched steady state microbial consortium is provided, said method comprising:

(a) providing environmental samples comprising indigenous microbial populations of said target oil reservoir;

(b) enriching for one or more steady state microbial consortium present in said samples wherein said enriching results in a consortium that utilizes crude oil as a carbon source under anaerobic, denitrifying conditions;

(c) characterizing the enriched steady state consortiums of (b) using 16S rDNA profiling;

(d) assembling a consortium using the characterization of (c) comprising microbial genera comprising one or more *Thauera* species and any two additional species that are members of genera selected from the group consisting of Rhodocyclaceae, Pseudomonadales, Bacteroidaceae, Clostridiaceae, Incertae Sedis, Spirochaetaceaes, Deferribacterales, Brucellaceae and Chloroflexaceae;

(e) identifying at least one relevant functionality of the consortium of (d);

(f) growing the enriched steady state consortium of (e) having at least one relevant functionality to a concentration sufficient for reservoir inoculation; and (g) inoculating the target reservoir with said sufficient concentration of the consortium of (f) and injection water comprising one or more electron acceptors wherein the consortium grows in the reservoir and wherein said growth promotes increased oil recovery.

BRIEF DESCRIPTION OF FIGURES OF THE INVENTION

FIG. 1: Distribution of microorganisms in the parent POG1 consortium after three months in second-generation parent populations as determined by 16S rDNA identities.

Figure 2A:
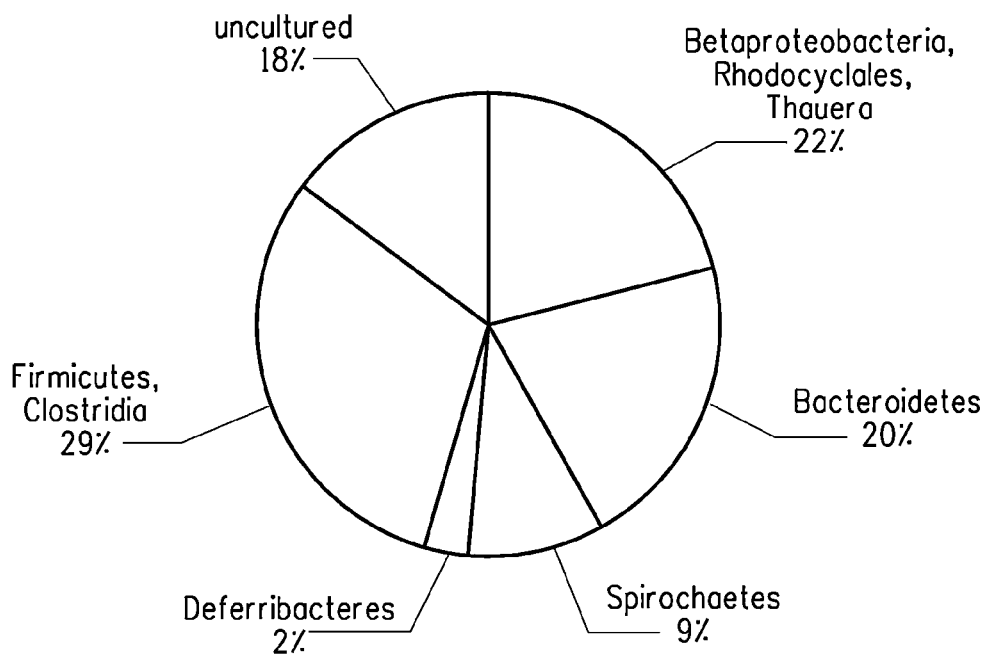
Figure 2B:
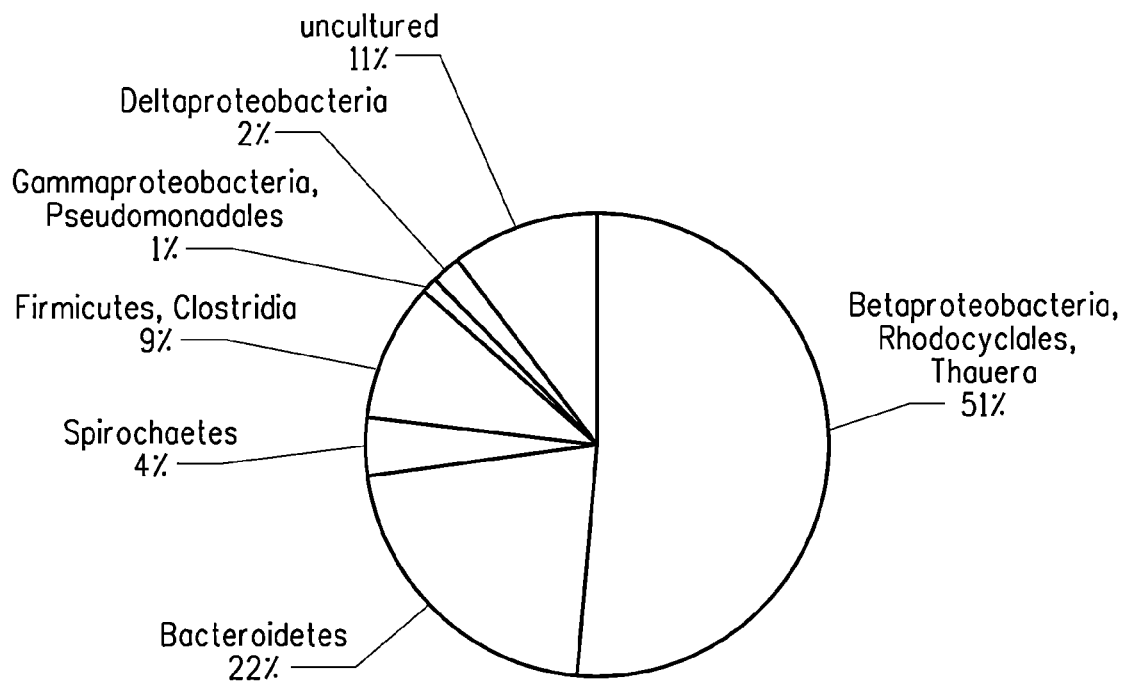

FIGS. 2A and 2B: Distribution of microorganisms in the parent POG1 consortium after 190 days in second- and third-generation parent populations determined by 16S rDNA identities. FIG. 2A: Population distribution of third-generation parent at 190 days while 6400 ppm Nitrate had been reduced. FIG. 2B: Population distribution of second-generation parent at 240 days while 6400 ppm Nitrate had been reduced FIG. 3: Diagram of the anaerobic chemostat bioreactor for denitrifying growth studies with the steady state POG1 consortium: A) Reverse flow bubbler; B) Nitrogen manifold; C) Feed sampling syringe and relief valve (5 psi); D) Feed syringe pump; E) Feed reservoir head space nitrogen gas port; F) Feed input port on chemostat bioreactor; G) Feed medium reservoir (minimal and nitrate); H) Chemostat Bioreactor; I) Minimal salt medium and consortium culture; J) Magnetic stirrer; K) Crude oil supplement; L) Effluent reservoir; M) Effluent exit port on chemostat bioreactor; N) Effluent reservoir head space nitrogen gas port; O) Effluent syringe port; P) Effluent sampling syringe and relief valve (5 psi); Q) Inoculation and sampling port on chemostat bioreactor; R) Extra port and plug; S) Chemostat bioreactor head space nitrogen gas port.

Figure 4:
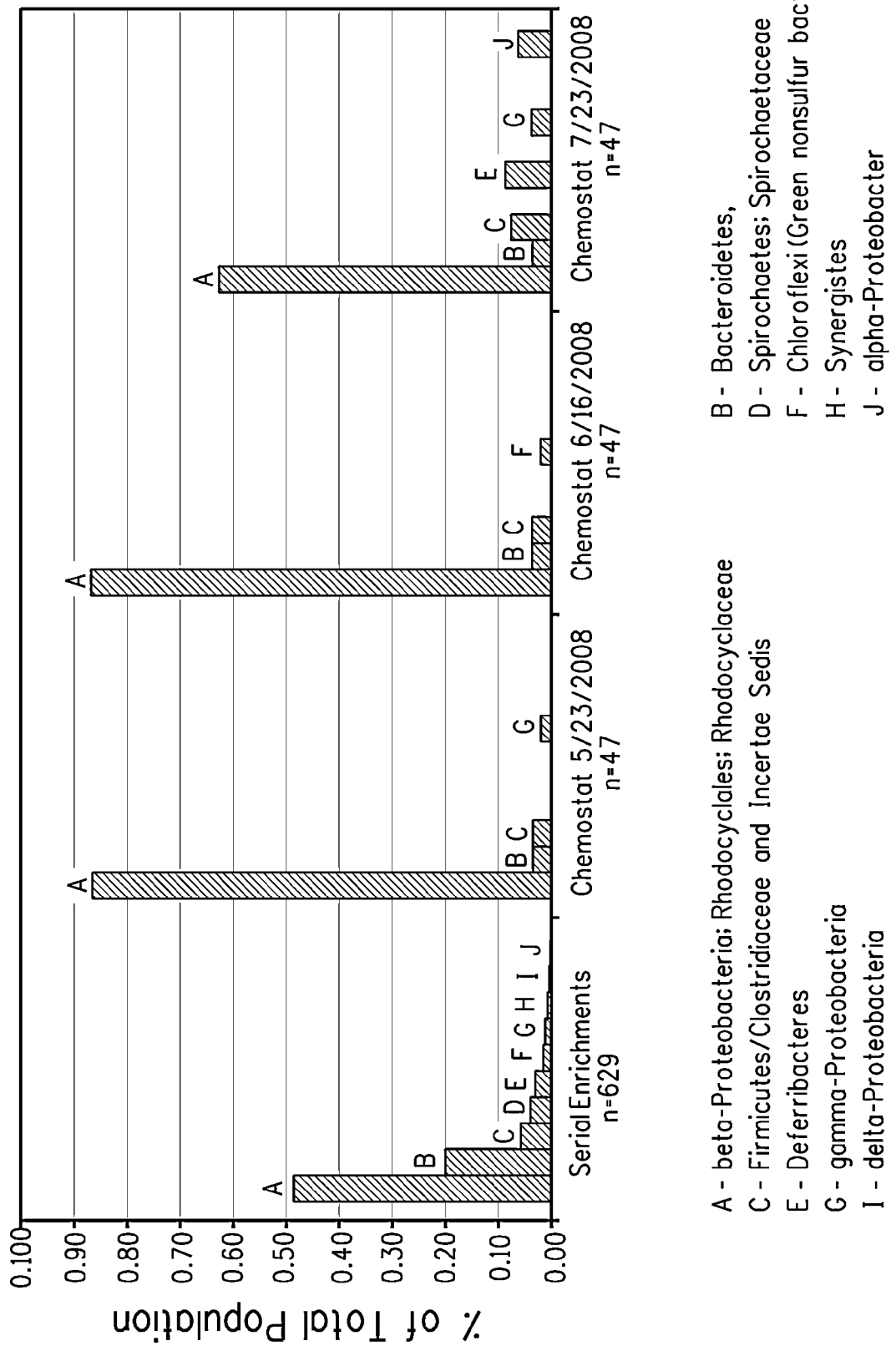

FIG. 4: Distribution of microorganisms in the steady state POG1 as determined by 16S rDNA identities. Consortium constituents at 0, 28 and 52 day, were compared to the parent populations.

Figure 5:
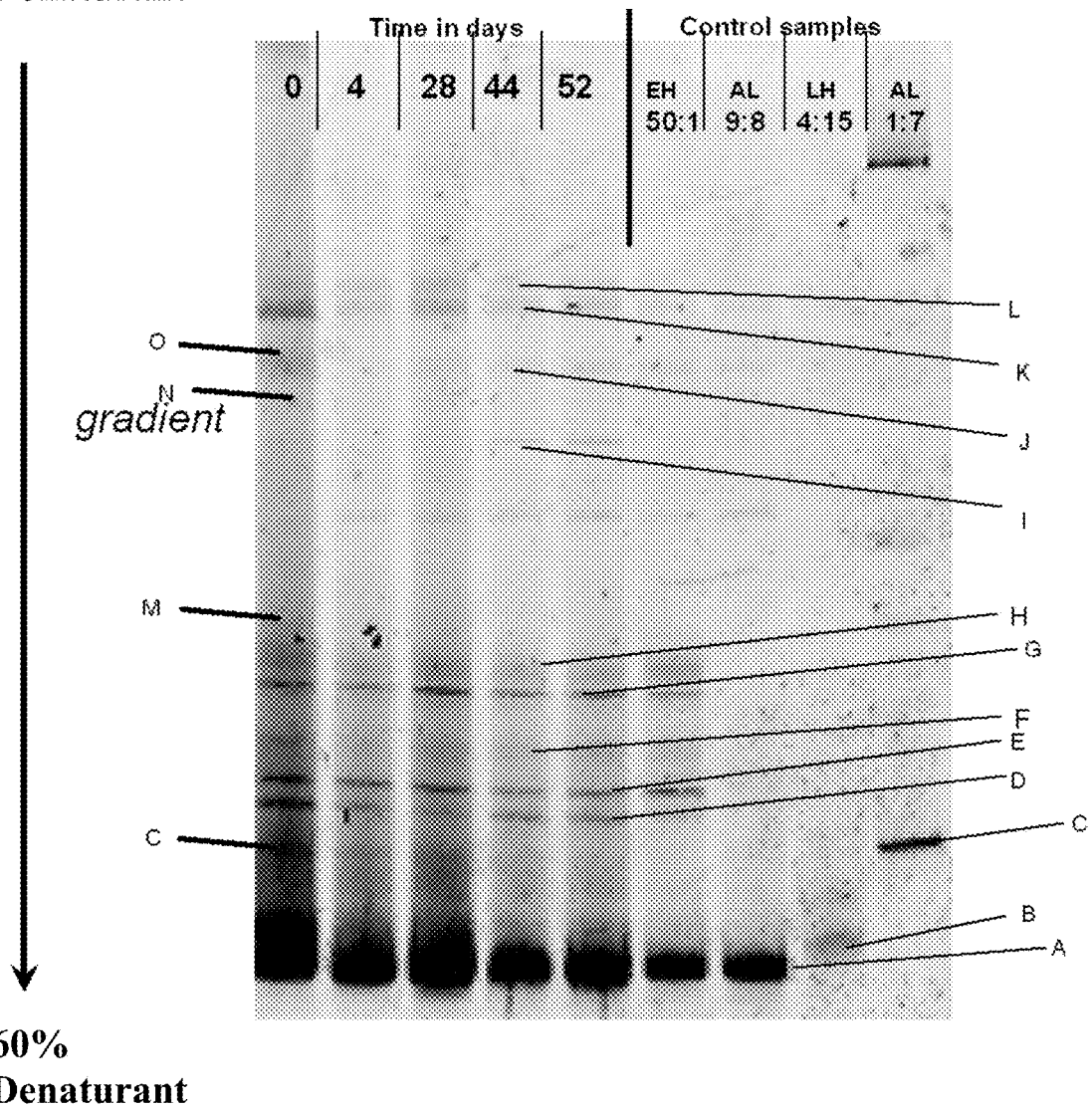

FIG. 5: Denaturing gradient gel electrophoresis fingerprint profile of the bacterial 16S rRNA gene fragments derived from community DNA extracted from the steady state POG1 chemostat bioreactor using primers SEQ ID NO: 12 and SEQ ID NO: 14 for region V4-5. (A) *Thauera* AL9:8 is a prominent species of a consortium as described herein. (B) *Pseudomonas stutzeri* LH4:15 is also a represented species of the consortium. (C) *Ochrobactrum oryzae* AL1:7 are a minor species. Minor bacterial species (D through L) are present in all samples. Bacterial species (C & M through O) are less important members of population and are selected against.

Figure 6:
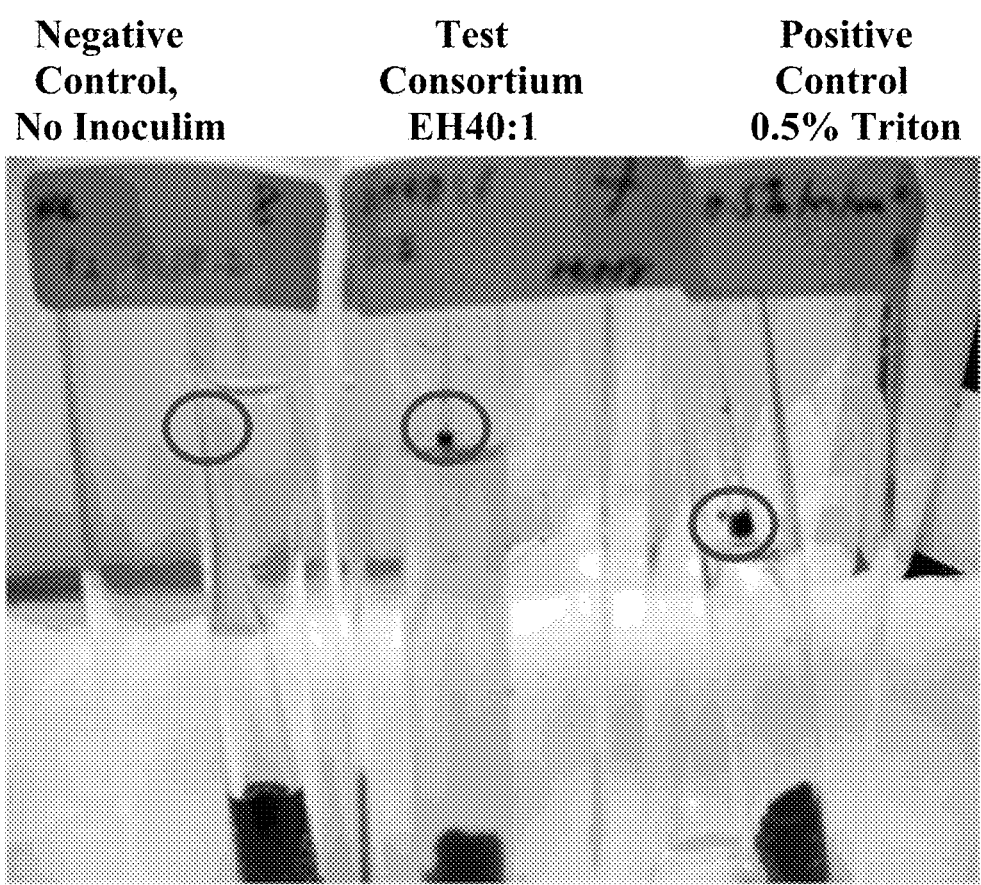

FIG. 6: Microsand column oil release—Using oil on North Slope sand, the 3$^{rd}$ generation parent POG1 consortium culture EH40:1 (2400 ppm Nitrate).

The following sequences conform to 37 C.F.R. §1.821-1.825 ("Requirements for Patent Applications Containing Nucleotide Sequences and/or Amino Acid Sequence Disclosures—the Sequence Rules") and are consistent with the World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions. The symbols and format used for nucleotide and amino acid sequence data comply with the rules set forth in 37 C.F.R. §1.822.

TABLE 1

PRIMER SEQUENCES USED IN THIS INVENTION

| Description | SEQ ID NO: Nucleic acid |
|---|---|
| 8F Bacterial 16S rDNA forward universal primer | 1 |
| 1492 R Bacterial 16S rDNA reverse universal primer | 2 |
| 1407 R Bacterial 16rDNA reverse universal primer | 3 |
| U518R, 16S rDNA universal reverse primer | 4 |

TABLE 1-continued

PRIMER SEQUENCES USED IN THIS INVENTION

| Description | SEQ ID NO: Nucleic acid |
|---|---|
| UB 357F Bacterial 16S rDNA forward universal primer | 5 |
| dG·UB 357F DGGE Bacterial 16S rDNA universal forward primer with 5' 40-bp GC-rich clamp | 6 |
| UA 341F1 Archaeal 16S rDNA universal forward primer | 7 |
| dG·UA 341F1 DGGE Archaeal 16S rDNA universal forward primer with 5' 40-bp GC-rich clamp | 8 |
| UA 341F2 Archaeal 16S rDNA universal forward primer | 9 |
| dG·UA 341F2 DGGE Archaeal rDNA universal forward 16S primer with 5' 40-bp GC-rich clamp | 10 |
| U 519F Universal 16S rDNA forward primer | 11 |
| dG·U 519F DGGE Universal 16S rDNA forward primer with 5' 40-bp GC-rich clamp | 12 |
| UA958R, Archaeal universal 16S rDNA reverse primer | 13 |
| UB 939R, Bacterial 16S rRNA universal reverse primer | 14 |

The following DNA sequences were consensus sequences of unique cloned PCR sequences, which were generated using universal 16S primers with DNA isolated from whole POG1 community:

SEQ ID NO: 15 is the consensus DNA sequence, clones ID: 1A: *Thauera* sp AL9:8

SEQ ID NO: 16 is the consensus DNA sequence, clones ID: 1B: *Thauera* sp R26885

SEQ ID NO: 17 is the consensus DNA sequence, clones ID: 1C: *Azoarcus* sp mXyN1

SEQ ID NO: 18 is the consensus DNA sequence, clones IDI: *Azoarcus* sp mXyN1

SEQ ID NO: 19 is the consensus DNA sequence, clones ID: 1E: *Thauera* sp R26885

SEQ ID NO: 20 is the consensus DNA sequence, clones ID: 1F: *Azotobacter beijerinckii*

SEQ ID NO: 21 is the consensus DNA sequence, clones ID: 1G: *Thauera* sp R26885

SEQ ID NO: 22 is the consensus DNA sequence, clones ID: 1H: *Azoarcus* sp mXyN1

SEQ ID NO: 23 is the consensus DNA sequence, clones ID: 1I: *Thauera aromatica*

SEQ ID NO: 24 is the consensus DNA sequence, clones ID: 1J: *Thauera aromatica*

SEQ ID NO: 25 is the consensus DNA sequence, clones ID: 1: *Thauera aromatica*

SEQ ID NO: 26 is the consensus DNA sequence, clones ID: 1 L: *Thauera aromatica*

SEQ ID NO: 27 is the consensus DNA sequence, clones ID: 1M: *Thauera aromatica*

SEQ ID NO: 28 is the consensus DNA sequence, clones ID: 1N: *Thauera aromatica*

SEQ ID NO: 29 is the consensus DNA sequence, clones ID: 1O: *Azoarcus* sp. EH10

SEQ ID NO: 30 is the consensus DNA sequence, clones ID: 1P: *Thauera* sp R26885
SEQ ID NO: 31 is the consensus DNA sequence, clones ID: 1Q: *Thauera aromatica*
SEQ ID NO: 32 is the consensus DNA sequence, clones ID: 1R: *Thauera aromatica*
SEQ ID NO: 33 is the consensus DNA sequence, clones ID: 1S: *Thauera aromatica*
SEQ ID NO: 34 is the consensus DNA sequence, clones ID: 1T: *Thauera aromatica*
SEQ ID NO: 35 is the consensus DNA sequence, clones ID: 1U: *Thauera aromatica*
SEQ ID NO: 36 is the consensus DNA sequence, clones ID: 1V: *Thauera aromatica*
SEQ ID NO: 37 is the consensus DNA sequence, clones ID: 1W: *Thauera aromatica*
SEQ ID NO: 38 is the consensus DNA sequence, clones ID: 1X: *Thauera aromatica*
SEQ ID NO: 39 is the consensus DNA sequence, clones ID: 1Y: *Thauera aromatica*
SEQ ID NO: 40 is the consensus DNA sequence, clones ID: 1Z: *Thauera aromatica*
SEQ ID NO: 41 is the consensus DNA sequence, clones ID: 1AZ: *Thauera aromatica*
SEQ ID NO: 42 is the consensus DNA sequence, clones ID: 2: *Finegoldia magna*
SEQ ID NO: 43 is the consensus DNA sequence, clones ID: 3 *Spirochaeta* sp MET-E
SEQ ID NO: 44 is the consensus DNA sequence, clones ID: 4: *Azotobacter beijerinckii*
SEQ ID NO: 45 is the consensus DNA sequence, clones ID: *Finegoldia magna*
SEQ ID NO: 46 is the consensus DNA sequence, clones ID: 6: *Azotobacter beijerinckii*
SEQ ID NO: 47 is the consensus DNA sequence, clones ID: 7: *Ochrobactrum* sp mp-5
SEQ ID NO: 48 is the consensus DNA sequence, clones ID: 8A: Anaerovorax sp. EH8A
SEQ ID NO: 49 is the consensus DNA sequence, clones ID: 8B: Anaerovorax sp. EH8B
SEQ ID NO: 50 is the consensus DNA sequence, clones ID: 9A: *Finegoldia magna*
SEQ ID NO: 51 is the consensus DNA sequence, clones ID: 9B: *Finegoldia magna*
SEQ ID NO: 52 is the consensus DNA sequence, clones ID: 9C: *Finegoldia magna*
SEQ ID NO: 53 is the consensus DNA sequence, clones ID: 10: *Flexistipes* sp vp180
SEQ ID NO: 54 is the consensus DNA sequence, clones ID: 11: *Azoarcus* sp._EH11
SEQ ID NO: 55 is the consensus DNA sequence, clones ID: 12: *Clostridium chartatabidium* SEQ ID NO: 56 is the consensus DNA sequence, clones ID: 13: *Deferribacter desulfuricans*
SEQ ID NO: 57 is the consensus DNA sequence, clones ID: 14A: *Azotobacter beijerinckii*
SEQ ID NO: 58 is the consensus DNA sequence, clones ID: 14B: *Flexistipes* sp vp180
SEQ ID NO: 59 is the consensus DNA sequence, clones ID: 15: *Ochrobactrum lupini*
SEQ ID NO: 60 is the consensus DNA sequence, clones ID: 16A: *Pseudomonas pseudoalcligenes*
SEQ ID NO: 61 is the consensus DNA sequence, clones ID: 16B: *Pseudomonas putidau*
SEQ ID NO: 62 is the consensus DNA sequence, clones ID: 17A: *Pseudomonas pseudoalcligenes*
SEQ ID NO: 63 is the consensus DNA sequence, clones ID: 17B: *Clostridium chartatabidium*
SEQ ID NO: 64 is the consensus DNA sequence, clones ID: 18A: *Finegoldia magna*
SEQ ID NO: 65 is the consensus DNA sequence, clones ID: 18B: *Finegoldia magna*
SEQ ID NO: 66 is the consensus DNA sequence, clones ID: 18C: *Finegoldia magna*
SEQ ID NO: 67 is the consensus DNA sequence, clones ID: 19: *Thauera aromatica*
SEQ ID NO: 68 is the consensus DNA sequence, clones ID: 20: *Thauera aromatica*
SEQ ID NO: 69 is the consensus DNA sequence, clones ID: 21: *Azoarcus* sp. EH21
SEQ ID NO: 70 is the consensus DNA sequence, clones ID: 22: *Azotobacter beijerinckii*
SEQ ID NO: 71 is the consensus DNA sequence, clones ID: 23: *Azotobacter beijerinckii*
SEQ ID NO: 72 is the consensus DNA sequence, clones ID: 24: *Azotobacter beijerinckii*
SEQ ID NO: 73 is the consensus DNA sequence, clones ID: 25: *Azotobacter beijerinckii*
SEQ ID NO: 74 is the consensus DNA sequence, clones ID: 26: *Azotobacter beijerinckii*
SEQ ID NO: 75 is the consensus DNA sequence, clones ID: 27: *Clostridium* chartatabidium
SEQ ID NO: 76 is the consensus DNA sequence, clones ID: 28: *Clostridium aceticum*
SEQ ID NO: 77 is the consensus DNA sequence, clones ID: 29: *Deferribacter desulfuricans*
SEQ ID NO: 78 is the consensus DNA sequence, clones ID: 30: *Bacteroides* sp. EH30
SEQ ID NO: 79 is the consensus DNA sequence, clones ID: 31: *Finegoldia magna*
SEQ ID NO: 80 is the consensus DNA sequence, clones ID: 32: *Pseudomonas putida*
SEQ ID NO: 81 is the consensus DNA sequence, clones ID: 33: *Clostridium aceticum*
SEQ ID NO: 82 is the consensus DNA sequence, clones ID: 34: Anaerovorax sp. EH34
SEQ ID NO: 83 is the consensus DNA sequence, clones ID: 35: *Pseudomonas putida*
SEQ ID NO: 84 is the consensus DNA sequence, clones ID: 36: *Azotobacter beijerinckii*
SEQ ID NO: 85 is the consensus DNA sequence, clones ID: 37: *Azotobacter beijerinckii*
SEQ ID NO: 86 is the consensus DNA sequence, clones ID: 38: *Azoarcus* sp. EH36
SEQ ID NO: 87 is the consensus DNA sequence, clones ID: 39: *Flexistipes* sp vp180

DETAILED DESCRIPTION OF THE INVENTION

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

It is not intended that the scope of the invention be limited to the specific values recited when defining a range.

The means, methods and procedures for providing an enriched steady state consortium having one or more relevant functionality to enhance the release and recovery of oil from a petroleum reservoir are disclosed.

The following definitions are provided for the terms and abbreviations used in this application:

The term "environmental sample" means any substance exposed to hydrocarbons, including a mixture of water and oil comprising microorganisms. As used herein, environmental samples include water and oil samples that comprise indigenous microorganisms and/or populations of microorganisms of varying genus and species that may be characterized by 16S rDNA profiling or DNA fingerprinting techniques as described in detail below. The environmental samples may comprise a microbial consortium unique to a geographic region or target reservoir, or, alternatively the microbial consortium may be adaptable to other environment sites, geographies and reservoirs.

The term "enriching for one or more steady state consortium" as used herein means that an environmental sample may be enriched in accordance with the invention by culturing the sample in a chemostat bioreactor under desired conditions such as anaerobic denitrifying conditions using a basic minimal medium, such as SL-10 as described in Table 2 and a sample of the target oil or its components as a carbon source.

The term "core flood assay" refers to water-flooding the core of an oil reservoir after application of an oil recovery technique, i.e. a MEOR technology, to the reservoir. An increase in oil release represents the ability of applied microbes to aid in the release of oil from the core matrix.

The term "indigenous microbial populations" means native populations of microorganisms present in an oil reservoir (rock or soil matrices, oil, water or oil-water samples).

The term "components of the POG1 consortium" refers to members or microbial constituents (both major and minor) of the POG1 consortium. These may be indigenous to the consortium or may be added strains. Additional components such as electron acceptors and combination of electron acceptors could be present too.

The terms "steady state consortium" and "enriched steady state microbial consortium" refers to a mixed culture of microorganisms and/or microbial populations grown in a chemostat bioreactor and in a medium under specific growth conditions to enrich for growth of particular populations of microorganisms, and once enriched, to reach a stable condition such that the consortium does significantly change over time under a given set of conditions. The steady state is controlled by a limiting nutrient. In an embodiment the steady state consortium is provided by enriching the microorganisms in a defined minimal, denitrifying medium, under anaerobic denitrifying conditions, using crude oil as the carbon source, until the population has reached its steady state. In the present case, electron acceptor, nitrate, is limiting and is fed at a constant flow. The consortium may comprise microbial populations from environmental samples or from pure or mixed non-indigenous cultures.

The term "POG1 consortium" as used herein refers to a consortium derived from an environmental enrichment that was obtained from a soil sample contaminated with polycyclic aromatic hydrocarbons.

The term "crude oil" refers to a naturally occurring, flammable liquid found in rock formations and comprises a complex mixture of hydrocarbons of various molecular weights, plus other organic compounds. The crude oil may contain, for example, a mixture of paraffins, aromatics, asphaltenes, aliphatic, aromatic, cyclic, polycyclic and polyaromatic hydrocarbons. The crude oil may be generic or may be from a reservoir targeted for enhanced oil recovery.

The term "electron acceptor" refers to a molecule or compound that receives or accepts an electron during cellular respiration.

The terms "denitrifying" and "denitrification" mean reducing nitrate for use as an electron acceptor in respiratory energy generation. The term "nitrates" and "nitrites" refers to any salt of nitrate ($NO_3$) or nitrite ($NO_2$).

The term "relevant functionalities" means that the consortium has the ability to function in ways that promotes oil recovery. Certain such functionalities include:

(a) alteration of the permeability of the subterranean formation for improved water sweep efficiency;

(b) production of biosurfactants to decrease surface and interfacial tensions;

(c) change in wettability;

(d) production of polymers other than surfactants that facilitate mobility of petroleum;

(e) production of low molecular weight acids which cause rock dissolution;

(f) generation of gases to increase formation pressure; and (g) reduction in oil viscosity.

The ability to demonstrate such functionalities in the present invention is dependent upon the consortium's ability to (1) grow under anaerobic conditions while reducing nitrates or nitrites; (2) use at least one component available in the oil well as a carbon source; (3) use at least one component in the injected or produced water; (4) grow in the presence of oil; (5) grow optimally in an oil well environment; and (6) achieve combinations of the above.

The term "modifying the environment of oil reservoir" includes the ability of the enriched steady state microbial consortium to affect an oil bearing formation in the following ways (per the relevant functionalities) 1) alter the permeability of the subterranean formation (sweep efficiency), (2) produce biosurfactants which decrease surface and interfacial tensions, (3) mediate changes in wettability, (4) produce polymers, which facilitate mobility of petroleum; and (5) generate gases (predominantly $CO_2$) that increase formation pressure; and (6) reduce oil viscosity.

The terms "well" and "reservoir" may be used herein interchangeably and refer to a subterranean or seabed formation from which oil may be recovered. The terms well and reservoir include the physical/chemical composition of the soil-rock-sediment structure of the reservoir below the surface.

The terms "target oil reservoir" and "target reservoir" may be used herein interchangeably and refer to a subterranean or seabed formation from which enhanced oil recovery is desired and to which the enriched steady state microbial consortium may be applied.

The term "growing on oil" means the microbial species capable of metabolizing aliphatic, aromatic and polycyclic aromatic hydrocarbons or any other organic components of the crude petroleum as a nutrient to support growth. The ability to grow on oil according to an embodiment of the invention eliminates the need for supplying certain nutrients, such as additional carbon sources, for using the microbial consortium for improved oil recovery.

The term "chemostat bioreactor" refers to a bioreactor used for a continuous flow culture to maintain microbial populations or a consortium of microorganism in a steady state growth phase. This is accomplished by regulating a continuous supply of medium to the microbes, which maintains the electron donor or electron receptor in limited quantities in order to control the growth rate of the culture.

The term "fingerprint profile" refers to the process of generating a specific pattern of DNA bands on a denaturing gradient electrophoresis gel that are defined by their length and sequence and is used to identify and describe the predominant microbial population of a culture assessing microbial diversity and population stability at any particular metabolic state.

The term "reservoir inoculation" means inoculation of the oil reservoir with one or more microbes for microbially-enhanced oil recovery.

The term "concentration sufficient for reservoir inoculation" means growing the microbial population to a density that would be suitable for inoculating the oil reservoir. For the purposes of this invention, a concentration of $10^7$ cells per milliliter of the sample may be employed.

The term "promotes increased oil recovery" as used herein means growing the microbial consortium in the oil reservoir under anaerobic conditions to provide for modification of the oil in the reservoir or well as defined above by a relevant functionality which may result in a change in the oil well or reservoir or the environment of the oil well or reservoir. Such change supports release of oil from sand or some of modification that enhances the recovery of oil.

The term "corrosion of oil recovery and processing hardware" as used herein refers to the chemical, physical and microbial processes that damage the oil pipeline and or the oil recovery hardware.

The term "rDNA typing" or "rDNA profiling" means the process of comparing the 16S rDNA gene sequences found in the experimental samples to rDNA sequences maintained in several international databases to identify, by sequence homology, the "closest relative" of microbial species.

The term "signature sequences" herein will refer to unique sequences of nucleotides in the 16S rRNA gene sequence that can be used specifically to phylogenetically define an organism or group of organisms. These sequences are used to distinguish the origin of the sequence from an organism at the kingdom, domain, phylum, class, order, genus, family, species and even an isolate at the phylogenic level of classification.

The term "structural domain" herein refers to specific sequence regions in the 16S rRNA gene sequence that when aligned reveal a pattern in which relatively conserved stretches of primary sequence and a secondary sequence alternate with variable regions that differ remarkably in sequence length, base composition and potential secondary structure. These structural domains of 16S rRNA gene sequence are divided into three categories: the universally conserved or "U" regions, semi conserved or "S" regions and the variable or "V" regions. All of the structural domains contain signature sequence regions that phylogenetically define a microorganism. (Neefs, J-M et al. Nucleic acids Res., 18: 2237, 1990, Botter, E. C., ASM News 1996).

The term "phylogenetics" refers to the study of evolutionary relatedness among various groups of organisms (e.g., bacterial or archaeal species or populations).

The term "phylogenetic typing", "phylogenetic mapping" or "phylogenetic classification" may be used interchangeably herein and refer to a form of classification in which microorganisms are grouped according to their ancestral lineage. The methods herein are specifically directed to phylogenetic typing on environmental samples based on 16S ribosomal DNA (rDNA) sequencing. In this context, approximately 1400 base pair (bp) length of the 16S rDNA gene sequence is generated using 16S rDNA universal primers identified herein and compared by sequence homology to a database of microbial rDNA sequences. This comparison is then used to help taxonomically classify pure cultures for use in enhanced oil recovery.

The abbreviation "DNA" refers to deoxyribonucleic acid.

"Gene" is a specific unit on a DNA molecule that is composed of a nucleotide sequence that encodes a distinct genetic message for regulatory regions, transcribed structural regions or functional regions.

The abbreviation "rDNA" refers to ribosomal operon or gene sequences encoding ribosomal RNA on the genomic DNA sequence.

The abbreviation "NTPs" refers to ribonucleotide triphosphates, which are the chemical building blocks or "genetic letters" for RNA.

The abbreviation "dNTPs" refers to deoxyribonucleotide triphosphates, which are the chemical building blocks or "genetic letters" for DNA.

The term "rRNA" refers to ribosomal structural RNA, which includes the 5S, 16 S and 23S rRNA molecules. The term "rRNA operon" refers to an operon that produces structural RNA, which includes the 5S, 16 S and 23S ribosomal structural RNA molecules.

The term "mRNA" refers to an RNA molecule that has been transcribed from a gene coded on a DNA template and carries the genetic information for a protein to the ribosomes to be translated and synthesized into the protein.

The term "hybridize" is used to describe the formation base pairs between complementary regions of two strands of DNA that were not originally paired.

The term "complementary" is used to describe the relationship between nucleotide bases that are capable of hybridizing to one another. For example, with respect to DNA, adenosine is complementary to thymine and cytosine is complementary to guanine.

The abbreviation "cDNA" refers to DNA that is complementary to and is derived from either messenger RNA or rRNA.

The abbreviation "NCBI" refers to the National Center for Biotechnology Information.

The term "GenBank" refers to the National Institute of Health's genetic sequence database.

The term "nutrient supplementation" refers to the addition of nutrients that benefit the growth of microorganisms that are capable of using crude oil as their main carbon source but grow optimally with other non-hydrocarbon nutrients, i.e., yeast extract, peptone, succinate, lactate, formate, acetate, propionate, glutamate, glycine, lysine, citrate, glucose, and vitamin solutions.

The abbreviation "NIC" refers to non-inoculum, negative controls in microbial culture experiments.

The abbreviation "ACO" (autoclaved crude oil) refers to crude oil that has been steam sterilized using an autoclave, and is assumed to be devoid of living microbes.

The term "bacterial" means belonging to the bacteria— Bacteria are an evolutionary domain or kingdom of microbial species separate from other prokaryotes based on their physiology, morphology and 16S rDNA sequence homologies.

The term "microbial species" means distinct microorganisms identified based on their physiology, morphology and phylogenetic characteristics using 16S rDNA sequences.

The term "archaeal" means belongings to the Archaea— Archaea are an evolutionary domain or kingdom of microbial species separate from other prokaryotes based on their physiology, morphology and 16S rDNA sequence homologies.

The term "sweep efficiency" means the ability of injected water employed in water flooding oil recovery techniques to 'push' oil through a geological formation toward a producer well.

The term "biofilm" means a film made up of a matrix of a compact mass of microorganisms consisting of structural heterogeneity, genetic diversity, complex community interactions, and an extracellular matrix of polymeric substances.

The term "irreducible water saturation" is the minimal water saturation that can be achieved in a porous core plug when flooding with oil to saturation. It represents the interstitial water content of the matrix where the water is never completely displaced by the oil because a minimal amount of water must be retained to satisfy capillary forces.

The term "ribotyping" or "riboprint" refers to fingerprinting of genomic DNA restriction fragments that contain all or part of the rRNA operon encoding for the 5S, 16S and 23S rRNA genes. Ribotyping, as described herein, is where restriction fragments, produced from microbial chromosomal DNA, are separated by electrophoresis, transferred to a filter membrane and probed with labeled rDNA operon probes. Restriction fragments that hybridize to the label probe produce a distinct labeled pattern or fingerprint/barcode that is unique to a specific microbial strain. The ribotyping procedure can be entirely performed on the Riboprinter® instrument (DuPont Qualicon, Wilmington, Del.).

The term "percent identity", as known in the art, is a relationship between two or more polypeptide sequences or two or more polynucleotide sequences, as determined by sequence comparisons. In the art, "identity" also means the degree of sequence relatedness or homology between polynucleotide sequences, as determined by the match between strings of such sequences and their degree of invariance. The term "similarity" refers to how related one nucleotide or protein sequence is to another. The extent of similarity between two sequences is based on the percent of sequence identity and/or conservation. "Identity" and "similarity" can be readily calculated by known methods, including but not limited to those described in "Computational Molecular Biology, Lesk, A. M., ed. Oxford University Press, NY, 1988"; and "Biocomputing: Informatics and Genome Projects, Smith, D. W., ed., Academic Press, NY, 1993"; and "Computer Analysis of Sequence Data, Part I, Griffin, A. M., and Griffin, H. G., eds., Humana Press, NJ, 1994"; and "Sequence Analysis in Molecular Biology, von Heinje, G., ed., Academic Press, 1987"; and "Sequence Analysis Primer, Gribskov, M. and Devereux, J., eds., Stockton Press, NY, 1991". Preferred methods to determine identity are designed to give the best match between the sequences tested. Methods to determine identity and similarity are codified in publicly available computer programs.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: the GCG suite of programs (Wisconsin Package Version 9.0, Genetics Computer Group (GCG), Madison, Wis.), BLASTP, BLASTN, BLASTX (Altschul, S. F. et al., J. Mol. Biol. 215: 403-410, 1990), DNASTAR (DNASTAR, Inc., Madison, Wis.), and the FASTA program incorporating the Smith-Waterman algorithm (Pearson, W. R., Comput. Methods Genome Res., [Proc. Int. Symp., Meeting Date 1992, 111-120. eds.: Suhai, Sandor. Publisher: Plenum, New York, N.Y., 1994). Within the context of this application, it will be understood that where sequence analysis software is used for analysis, the results of the analysis will be based on the "default values" of the program referenced, unless otherwise specified. As used herein "default values" will mean any set of values or parameters that load with the software when first initialized.

The term "denaturing gradient gel electrophoresis" or "DGGE" refers to a molecular fingerprinting method that separates polymerase chain reaction-generated (PCR-generated) DNA products based on their length and sequence. The separation of the PCR product fragment of the same size, but with a different sequence reflects differential denaturing characteristics of the DNA due to their sequence variation. During DGGE, PCR products encounter increasingly higher concentrations of chemical denaturant as they migrate through a polyacrylamide gel. The rDNA PCR products are generated from the mixed microbial population being characterized. The weaker melting domains of certain double-stranded PCR sequences will begin to denature, slowing the electrophoretic migration dramatically. The different sequences of DNA (that are generated from different bacteria) will denature at different denaturant concentrations resulting in a pattern of bands that can be collectively referred to as the "community fingerprint profile". In theory, each band in a given DGGE fingerprint profile represents an individual bacterial species present in the community. Once generated, the data represents a fingerprint profile of the population at a given point in time and under certain growth conditions. The DGGE fingerprint profile can be uploaded into database to compare profiles of the consortium under prescribed growth conditions. Thus DGGE is used to generate the finger prints of a microbial community and to resolve the genetic diversity of complex microbial populations.

The present method provides for microbially enhanced oil recovery from an oil reservoir using an enriched steady state microbial consortium comprising the following steps: 1) obtaining an environmental samples comprising indigenous microbial populations; 2) developing an enriched steady state microbial consortium wherein said consortium is enriched under anaerobic denitrifying conditions, using crude oil as the carbon source, until the population has reached its steady state; 3) developing fingerprint profiles of samples of the steady state consortium using 16S rDNA profiling methods of said samples; 4) selecting samples of the consortium comprising various microbial genera, for example, one or more Thauera species and other additional species selected from the group consisting of Rhodocyclaceae, Pseudomonadales., Bacteroidaceae, Clostridiaceae, Incertae Sedis., Spirochete, Spirochaetaceaes., Deferribacterales, Brucellaceae and Chloroflexaceae; 5) identifying at least one relevant functionality of the selected enriched steady state consortium for use in improving oil recovery; 6) growing the selected enriched steady state consortium having at least one relevant functionality to a concentration sufficient for reservoir inoculation; 7) inoculating a subsurface reservoir matrix with said sufficient concentration of the steady state consortium and injection water comprising one or more electron acceptors wherein the consortium grows in the subsurface reservoir matrix and wherein the activity or growth of the said consortium promotes increased oil recovery.

Environmental Samples for Development of a Microbial Consortium

The sample source used for enrichment cultures and development of a consortium for use in MEOR may be: (1) the oil well itself in the form of: a water sample (injection, power or production water), soil from a reservoir core or from a sample of the targeted oil; (2) an environmental sample that has been exposed to crude oil or any one or combination of its components, such as paraffins, aromatics, asphaltenes, etc.; or (3) a preexisting consortium that meet the criteria for growth in the presence of the targeted oil. The sample must be in contact with or near the oil formation since sample constituents are specific to an area. Sampling near an intended location is preferred. The sample volume and the number of microbial cells per milliliter may vary from 1 mL to 5 L and from $10^5$ to $10^{10}$ cells/mL, depending upon the specific requirements of the intended application. For the purposes of this invention, the cell density in the sample may be $10^7$ cells per milliliter. To these samples, a basic mineral salt medium, which is required for microbial growth, vitamins and electron acceptors, may be added in addition to the sample of the crude oil from the desired location and the mixture may be incubated at a suitable temperature to allow development of the desired consortium with specific functionalities.

In an embodiment, a steady state microbial consortium may be provided by an environmental sample obtained from Milne Pont reservoir, North Slope of Alaska.

In another embodiment an environmental sample may be provided from an oil well or reservoir environment located in the oil fields of Texas, Oklahoma, California, the Gulf of Mexico, West Africa, the Middle East, India, China, North and Eastern South America, North Sea and the Old Soviet Union.

Microbial Chemostat Bioreactor

The environmental samples comprising microbial populations may be grown in a chemostat bioreactor using enrichment techniques. The enrichment conditions may include growing an environmental sample under anaerobic denitrifying conditions in bottles while limiting the concentration of electron acceptor provided during anaerobic respiration since the rate of manual feed is often too slow to keep up with reduction of nitrate. In addition, if too high a concentration of nitrate (e.g., >2500 ppm) were to be applied, it may either inhibit growth of some microbes or be toxic and kill some other species. Conversely, denitrifying bacteria stop growing when nitrate is completely reduced, hence allowing other microbial populations to dominate the composition of the consortium through reducing other trace metals, minerals and unsaturated hydrocarbons or organic molecules. Fluctuations in nitrate levels may affect changes in the microbial composition of the consortium and unduly influence the definition of the composition of the population in it. The non-limiting examples provided herein describe how to manipulate these conditions to enrich for and identify desired constituents of a steady state microbial consortium.

Chemostat bioreactors are systems for the cultivation of microbial communities or single microbial species and provide for maintaining conditions for microbial growth and populations at a steady state by controlling the volumetric feed rate of a growth dependant factor. The chemostat setup consists of a sterile fresh nutrient reservoir connected to a growth reactor. Fresh medium containing nutrients essential for cell growth is continuously pumped to the chamber from the medium reservoir. The medium contains a specific concentration of one or more growth-limiting nutrient that allows for growth of the consortium in a controlled physiological steady state. Varying the concentration of the growth-limiting nutrients will, in turn, change the steady state concentration of cells. The effluent, consisting of unused nutrients, metabolic wastes and cells, is continuously removed from the vessel, pumped from the chemostat bioreactor to the effluent reservoir and monitored for complete reduction of nitrate. To maintain constant volume, the flow of nutrients and the removal of effluent are maintained at the same rate and are controlled by synchronized syringe pumps.

Enrichment Conditions

As stated above an environmental sample may be enriched in accordance with the invention herein by culturing the sample in a chemostat bioreactor under desired conditions such as anaerobic denitrifying conditions. Additional enrichment conditions include use of a basic minimal medium, such as SL-10 as described in Table 2.

The chemostat bioreactor may be held at a room temperature that may fluctuate from about 15° C. to about 35° C.

The steady state consortium may be enriched under anaerobic, denitrifying conditions using a nitrate salt as the electron acceptor. The enrichment culture thus may include nitrate concentrations from 25 ppm to 10,000 ppm. More specifically, the nitrate concentration may be from 25 ppm to 5000 ppm. Most specifically, the nitrate concentration may be from 100 ppm to 2000 ppm.

In one embodiment an enriched steady state microbial consortium designated POG1 was developed under denitrifying conditions with a nitrate salt as the electron acceptor. Other suitable anaerobic reducing conditions would use selective electron acceptors that include, electron acceptors that could be used to develop similar consortia include, but are not limited to: iron (III), manganese (IV), sulfate, carbon dioxide, nitrite, ferric ion, sulfur, sulfate, selenate, arsenate, carbon dioxide and organic electron acceptors that include, but not limited the chloroethenes, fumarate, malate, pyruvate, acetylaldehyde oxaloacetate and similar unsaturated hydrocarbon compounds may also be used.

The enrichment of the consortium may include a minimal growth medium supplemented with additional required nutritional supplements, e.g., vitamins and trace metals, and crude oil as the carbon source as described in details below.

This consortium may be grown at a pH from 5.0 to 10. More specifically the pH could be from 6.0 to about 9.0. Most specifically the pH could be from 6.5 to 8.5. In addition, the steady state consortium should have an $OD_{550}$ from about 0.8 to about 1.2 and should actively reduce the electron acceptor.

Characterization of Microbial Populations in the Enriched Steady State Microbial Consortium Constituents or the microbial populations of the enriched steady state consortium may be identified by molecular phylogenetic typing techniques. Identification of microbial populations in a consortium provides for selection of a consortium with certain microbial genera and species described to have relevant functionalities for enhancing oil recovery.

In an embodiment of the invention, an enriched steady state consortium (referred to as "POG1") was developed from a parent mixed culture, enriched from an environmental sample, using crude oil from the targeted reservoir as the energy source. Various constituents of the consortium were characterized using fingerprint profiles of their 16S rDNA as described below, using signature regions within the variable sequence regions found in the 16S rRNA gene of microorganisms (see Gerard Muyzer, et al., Appl. Environ. Microbiol., 59: 695, 1993). DNA sequences of the V3 region of 16S rRNA genes in a mix population were targeted and PCR amplified as described in detail below. Using this method a consortium comprising members from Thauera, Rhodocyclaceae, Pseudomonadales, Bacteroidaceae, Clostridiaceae, Incertae Sedis, Spirochete, Spirochaetaceaes, Deferribacterales, Brucellaceae and Chloroflexaceae were characterized (FIG. 1). The *Thauera* strain AL9:8 was the predominant microorganism in the consortium. It represented between 35 to 70% of the constituents during sampling processes. There were 73 unique sequences (SEQ ID NOs: 15-87), which were grouped into eight phylum of bacteria, which included alpha-Proteobacteria, beta-Proteobacteria, gamma-Proteobacteria, Deferribacteraceae, Spirochaetes, Bacteroidetes, Chloroflexi (Green sulfur bacteria) and Firmicutes/Clostridiales. The primary genera continued to be the beta-Proteobacteria, Thauera and *Thauera* strain AL9:8 was the dominant constituent. There was a large diversity among the members of Thauera/Azoarcus group (Rhodocyclaceae), where there were 31 unique 16S rDNA sequences whose sequence differences occurred in the primary signature regions of the variable regions. Also the Firmicutes/Clostridiales group were diverse with 16 unique sequences that include constituents from the Clostridia (Clostridiaceae), and the Anaerovorax and Finegoldia group (Incertae Sedis). Further analyses using fingerprint profiling may allow assigning the DNA bands in the DGGE DNA fingerprint to some of these sequences.

Based on these characterizations of samples of an enriched steady state microbial consortium, an embodiment of the invention includes an enriched steady state consortium comprising species from: beta-Proteobacteria (Rhodocyclaceae, specifically *Thauera*), alpha-Proteobacteria, gamma-Proteobacteria, Deferribacteraceae, Bacteroidetes, Chloroflexi and Firmicutes/Clostridiales phyla.

Certain microbial genera and species are known to have the ability to enhance oil recovery. See, co-pending U.S. application Ser. No. 12/194,749, describing specifically, the one or more microbial cultures may be selected from the group consisting of *Marinobacterium georgiense* (ATCC#33635), *Thauera aromatica* T1 (ATCC#700265), *Thauera chlorobenzoica* (ATCC#700723), *Petrotoga miotherma* (ATCC#51224), *Shewanella putrefaciens* (ATCC#51753), *Thauera aromatica* S100 (ATCC#700265), *Comamonas terrigena* (ATCC#14635), *Microbulbifer hydrolyticus* (ATCC#700072), and mixtures thereof, having relevant functionalities for improving oil recovery. Accordingly it is within the scope of the methods of the invention to provide a method wherein said one or more non-indigenous microorganisms is:
a) selected from the group consisting of *Marinobacterium georgiense Thauera aromatica* T1, *Thauera chlorobenzoica Petrotoga miotherma Shewanella putrefaciens, Thauera aromatica* S100), *Comamonas terrigena* (*Microbulbifer hydrolyticus*, and mixtures thereof; and
b) comprises a 16s rDNA sequence having at least 95% identity to a 16s rDNA sequence isolated from the microorganisms of (a).

Comparing the components of an enriched steady state consortium to the phylogeny of known microorganisms having the ability to enhance oil recovery provides a mechanism for selecting a consortium useful for enhancing oil recovery. Further, such known microorganisms may be added to a steady state consortium to further enhance oil recovery.

Phylogenetic Typing

The following description provides mechanisms for characterizing the constituents of the enriched steady state microbial consortium.

Methods for generating oligonucleotide probes and microarrays for performing phylogenetic analysis are known to those of ordinary skill in the art (Loy, A., et al., Appl. Environ. Microbiol., 70: 6998-700, 2004) and (Loy A., et al., Appl. Environ. Microbiol., 68: 5064-5081, 2002) and (Liebich, J., et al., Appl. Environ. Microbiol., 72: 1688-1691, 2006). These methods are applied herein for the purpose of identifying microorganisms present in an environmental sample.

Specifically, conserved sequences of the 16S ribosomal RNA coding region of the genomic DNA were used herein. However there are other useful methodologies for phylogenetic typing noted in the literature. These include: 23S rDNA or gyrate A genes or any other highly conserved gene sequences. 16S rDNA is commonly used because it is the largest database of comparative known phylogenetic genotypes and has proven to provide a robust description of major evolutionary linkages (Ludwig, W., et al., Antonie Van Leewenhoek, 64: 285, 1993 and Brown, J. R. et al., Nature Genet., 28: 631, 2001).

The primers described herein were chosen as relevant to environmental samples from an oil reservoir (Grabowski, A., et al., FEMS Micro. Eco., 544: 427-443, 2005) and by comparisons to other primer sets used for other environmental studies. A review of primers available for use herein can be found in Baker et al (G. C. Baker, G. C. et al., Review and re-analysis of domain-specific primers, J. Microbiol. Meth., 55: 541-555, 2003). Any primers which generate a part or whole of the 16S rDNA sequence would be suitable for the claimed method.

DNA extraction by phenol/chloroform technique is known in the art and utilized herein as appropriate for extracting DNA from oil contaminated environmental samples. However, there are other methodologies for DNA extraction in the literature that may be used in accordance with the present invention.

DNA sequencing methodologies that generate >700 bases of high quality sequence may be used for the type of plasmid based sequencing in accordance with the present invention in conjunction with other sequence quality analysis programs. The comparisons by homology using the BLAST algorithms to any comprehensive database of 16S rDNAs would achieve an acceptable result for identifying the genera of microorganisms present in the environmental sample. The most widely used databases are ARB (Ludwig, W., et al., ARB: a software environment for sequence data. Nucleic Acid Res., 32: 1363-1371, 2004) and NCBI.

Fingerprint Profiling

Fingerprint profiling is a process of generating a specific pattern of DNA bands on an electrophoresis gel that are defined by their length and sequence. This profile is used to identify and describe the predominant microbial population of a culture assessing microbial diversity and population stability at particular metabolic state. For example, each band and its intensity in a given DGGE fingerprint profile represent an individual bacterial species present in the community and its relative representation in the population. Once generated, the data represents a fingerprint profile of the population at a given point in time and under certain growth conditions. The DGGE fingerprint profile can be compared to profiles of the consortium under prescribed growth conditions.

Denaturing Gradient Gel Electrophoresis

This technique has been adopted to analyze PCR amplification products by targeting variable sequence regions in conserved genes such as one of the nine variable regions found in the 16S rRNA gene of microorganisms (Gerard Muyzer et al., supra and Neefs, J-M et al., supra, and Botter, E. C., ASM News 1996). DGGE provides a genetic fingerprint profile for any given population.

Denaturing gradient gel electrophoresis (DGGE) and temperature gradient gel electrophoresis (TGGE) are electrophoresis-gel separation methods that detect differences in the denaturing behavior of small DNA fragments (50-600 bp), separating DNA fragments of the same size based on their denaturing or "melting" profiles related to differences in their base sequence. This is in contrast to non-denaturing gel electrophoresis where DNA fragments are separated only by size.

The DNA fragments are electrophoresed through a parallel DGGE gel, so called because the linear gradient of denaturant ~30-60% (urea/formamide) is parallel to the gel's electric field. Using DGGE, two strands of a DNA molecule separate or melt, when a chemical denaturant gradient is applied at constant temperature between 55°-65° C. The denaturation of a DNA duplex is influenced by two factors: 1) the hydrogen bonds formed between complimentary base pairs (since GC rich regions melt at higher denaturing conditions than regions that are AT rich); and 2) the attraction between neighboring bases of the same strand, or "stacking". Consequently, a DNA molecule may have several melting domains, depending upon the denaturing conditions, which are characteristic of and determined by their nucleotide sequence. DGGE exploits the fact that virtually identical DNA molecules that have the same length and similar DNA sequence, which may differ by only one nucleotide within a specific denaturing domain, will denature at different conditions. Thus, when the double-stranded (ds) DNA fragment moves (by electrophoresis) through a gradient of increasing chemical denaturant, urea, formamide or both, it begins to denature and undergoes both conformational and mobility changes. At some point the two strands of the DNA to will come completely apart (also called "melting"). However, at some intermediate denaturant concentrations, as the denaturing environment increases, the two strands will become partially separated, with some segments of the molecules still being double-stranded and others being single-stranded, specifically at the particular low denaturing domains; thus, forming variable and intermediate denatured structures, which begin to retard the movement of the fragments through the gel denaturant gradients. The dsDNA fragment will travel faster than a denatured single-stranded (ss) DNA fragment. The more denatured fragment will travel slower through the gel matrix. The DGGE gel electrophoresis method offers a "sequence dependent, size independent method" for separating DNA molecules.

In practice, the DGGE electrophoresis is conducted at a constant temperature (60° C.) and chemical denaturants are used at concentrations that will result in 100% of the DNA molecules being denatured (i.e., 40% formamide and 7M urea). This variable denaturing gradient is created using a gradient maker, such that the composition of denaturants in the gel gradually decreases from the bottom of the gel to the top, where the fragments are loaded, e.g., 60% to 30%.

The principle used in DGGE profiling can also be applied to a second method, Temperature Gradient Gel Electrophoresis (TGGE), which uses a temperature gradient instead of a chemical denaturant gradient. This method makes use of a temperature gradient to induce the conformational change of dsDNA to ssDNA to separate fragments of equal size with different sequences. As in DGGE, DNA fragments will become immobile at different positions in the gel depending upon their different nucleotide sequences.

For characterizing microbial communities, DGGE fingerprint profiling has been applied to identify and characterize the genetic diversity of complex microbial populations much as, riboprinting has been applied to identify new environmental isolates by their rRNA fingerprint profile as being the same or different from previously described strains.

In practicing DGGE profiling, the variable sequence regions found in the 16S rRNA gene of microorganisms are targeted in PCR amplification of whole DNA isolated from a mix population (Gerard Muyzer et al (supra)). The variable or "V" regional segment not only differs in nucleotide sequence, but in length and secondary structure in the sequence. It is only recognizable as similar sequence in only closely related microorganisms. There are nine variable regions in the bacterial/archaeal 16S gene. These variable regions are designated by the letter V plus the number 1 through 9. Two V regions are most useful in using DGGE profile analysis, the V3 region and the V4/V5 region. Both V regions are flanked by universally conserved U regions.

The V3 region is flanked by two U sequences. The first at base coordinates 341 to 357 where bacteria and archaeal signature sequences exist. Bacterial universal primer, UB357F (SEQ NO: 5) and Archaeal universal primers 341F1 and 341F2, (SEQ NOs: 7, 9 respectively) are designed from this region. The other U region, which is universally conserved in all phylogenetic domains is found at base coordinates, 518 to 534. The domain universal reverse primer, UB518R (SEQ NO: 5) is designed from this region.

The V4/V5 region is also flanked by two universal conserved sequences. The first as above is the domain universal region at base coordinates, 518 to 534. The domain universal forward, U519F (SEQ NO: 11) was designed from this region. The other region at base coordinates 918 to 960, where additional universal bacterial and archaeal signature sequences exist. The bacterial universal reverse primer, UB939R (SEQ NO: 14) and Archaeal universal primer UA958R (SEQ NO: 13) in this application were designed from this region.

A 40-bp GC-rich clamp in the 5' end of one of the PCR primers makes the method robust for genetic fingerprint profiling analysis of microbial populations. For profile analysis of region V3, the GC-clamp was designed into the bacterial universal primer, designated dG•UB357F (SEQ NO: 6) and archaeal universal primers designated dG•341F1 and dG•341F2, (SEQ NOs: 8, 10 respectively) and for the V4/V5 region, the domain universal forward, designated dG•U 519F (SEQ NO: 12) was designed from this region. Using this method, PCR amplification of the total DNA from a diverse microbial population produces amplified fragments consisting of heterogeneous sequences of approximately 193 bp in length. These 16S rDNA fragments, when analyzed by DGGE analysis, demonstrate the presence of multiple distinguishable bands in the separation pattern, which are derived from the many different species constituting the population. Each band thereby, represents a distinct member of the population. Intensity of each band is most likely representative of the relative abundance of a particular species in the population, after the intensity is corrected for rRNA gene copies in one microbe versus the copies in others. The banding pattern also represents a DGGE profile or fingerprint of the populations. Using this method, it is possible to identify constituents, which represent only 1% of the total population. Changes in the DGGE fingerprint profile of the population can signal changes in the parameters, e.g., the electron donors and electron acceptors that determine the growth and metabolism of the community as a whole.

Relevant Functionalities of Characterized, Enriched Steady State Microbial Consortium Once an enriched steady state microbial consortium has been characterized, or in certain embodiments prior to genetic characterization of the constituent genetic characterization, the consortium may be assayed for one or more relevant functionality related to enhancing oil recovery, including ability to degrade crude oil under the conditions of interest. Assays for the relevant functionalities include micro-sand column release assay and the LOOS (Liberation of Oil Off Sand) test (see Example 8,) and the "sand packed slim tube or core flood test.

Inoculation of an Oil Well for Enhanced Oil Recovery

The following steps are taken to inoculate an oil well/reservoir:

a) Inoculating the microbial consortium in a bioreactor containing a anaerobic minimal salts medium, the target crude oil and an appropriate electron acceptor (e.g., nitrate herein).

b) Incubating the microbial consortium of step (a) at a temperature similar to the target well to obtain a seed population of the microbial consortium (e.g., 30° C., or in the range of room temperature, +/−5° C. in this disclosure).

c) Inoculating the seed microbial consortium of step (b) under anaerobic condition into anaerobic reservoir injection water.

d) Injecting the biological mixture of step (c) in to the reservoir, followed by injection water with dissolved electron acceptor to push the consortium mixture into the reservoir subterranean matrix, allowing the microbial consortium to grow and propagate resulting in dissociation and release of the crude oil from the reservoir matrix.

Benefits of Enhancing Oil Recovery Using Enriched Steady State Microbial Consortium In this application, methods are disclosed to provide an enriched steady state consortium of microbial population, under denitrifying conditions (using an anaerobic electron acceptor), using a chemostat bioreactor. The enriched steady state consortium population anaerobically degrades crude oil components under reservoir conditions to modify the physiochemical properties of the crude oil and/or the reservoir environment, resulting in enhanced recovery of the crude oil. The ideal consortium would be developed and enriched from an indigenous microbial population.

An additional benefit of the application of the present microbial consortium may be in the prevention of the damage to the oil pipeline and oil recovery hardware. Corrosion of the oil pipeline and other oil recovery hardware may be defined as the destructive attack on metals by some microbial, chemical or electrochemical mechanisms. Microbially induced corrosion in oil pipelines is known (EP3543361 B and U.S. Pat. No. 4,879,240A) and is caused by a variety of microorganisms including, but not limited to, aerobic bacteria, anaerobic bacteria, acid forming bacteria, slime formers, and sulfate reducing bacteria (SRB). In an anaerobic environment, corrosion is most commonly attributed to the growth of dissimilatory SRB. This group of bacteria is responsible for possibly 50% of all instances of corrosion. The control of microbial corrosion in oil recovery operations generally incorporates both physical or mechanical and chemical treatments.

The use of nitrate as a means of controlling the activity of SRB and removing hydrogen sulfide from oil pipeline and other oil recovery hardware is well documented (The stimulation of nitrate-reducing bacteria (nrb) in oilfield systems to control sulfate-reducing bacteria (srb), microbiologically influenced corrosion (mic) and reservoir souring an introductory review, published by the Energy Institute, London, 2003). Application of denitrifying microorganisms for enhancing oil recovery, therefore, may provide a cost effective, efficient and environmentally acceptable means of controlling SRB and remediating hydrogen sulfide contaminated systems, avoiding the use of expensive and environmentally unacceptable organic biocides. It is therefore proposed that the use of the consortium of denitrifying anaerobic microbial consortium POG1 would not only be beneficial to oil recovery, it would also prevent costly damage to the oil pipeline and other oil recovery hardware.

General Methods

Growth of Microorganisms

Techniques for growth and maintenance of anaerobic cultures are described in "Isolation of Biotechnological Organisms from Nature", (Labeda, D. P. ed. p 117-140, McGraw-Hill Publishers, 1990). Anaerobic growth was measured by nitrate depletion from the growth medium over time. Nitrate was utilized as the primary electron acceptor under the growth conditions used in this invention. The reduction of nitrate to nitrogen has been previously described (Moreno-Vivian, C., et al., J. Bacteriol., 181: 6573-6584, 1999). In some cases, nitrate reduction processes lead to nitrite accumulation, which is subsequently, further reduced to nitrogen. Accumulation of nitrite is therefore also considered evidence for active growth and metabolism by these microorganisms.

Description of the Chemostat Bioreactor Used in this Invention

Figure 3:
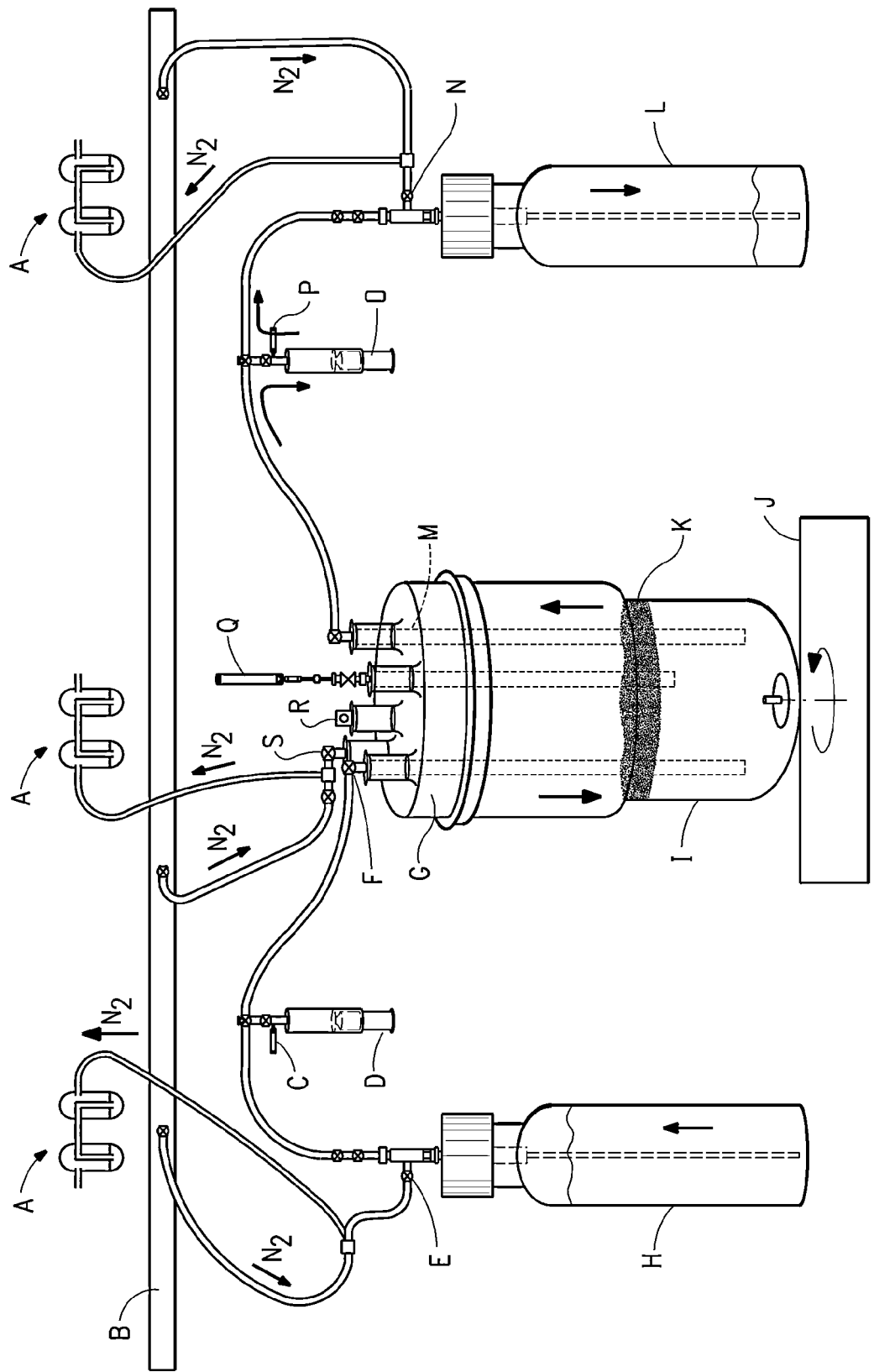

In this disclosure, a chemostat bioreactor was used as a bioreactor to maintain the consortium population in a steady state, using crude oil in excess as the sole energy source and a limiting nitrate supply, as the electron acceptor. FIG. 3 shows a diagram of the chemostat bioreactor used in this invention. The chemostat bioreactor was designed and used as a continuous-cultivation system, using a constant feed of medium and nitrate to develop a steady state population designated "POG1 consortium". The chemostat bioreactor was operated under anaerobic conditions, at room temperature, pH 7.4 and one atmosphere pressure, using the targeted crude oil (Milne Pont reservoir, North Slop of Alaska) as the carbon source (primary source of electron donors), and supplying a minimal salts medium (Table 2) containing minimal essential minerals, salts, vitamins and nitrate, as the primary electron acceptor, for growth.

The chemostat bioreactor was set up in a chemical hood at room temperature (20 to 25° C.). All headspaces were anaerobic, using a blanket of nitrogen and an open-ended nitrogen flow (<1 psi) system, with a reverse double bubbler system, containing 5 mL mineral oil closing off the system from the atmosphere. Both the initial SL10 medium (Table 2) in the bioreactor and in the medium feed reservoir were degassed with an anaerobic mix of carbon dioxide and nitrogen (20/80 on a % basis) for 10 min, the pH checked and then titrated with either $CO_2/N_2$ mix or just $N_2$ until it was pH7.4. The SL10 minimal salts medium (1 L), in the bioreactor, was initially supplemented with 800 ppm nitrate and 400 mL of the targeted crude oil. The bioreactor was inoculated with 50 mL of the $3^{rd}$ generation ($3^{rd}$ gen) parent POG1 from enrichment culture (designated EH50:1) grown on the target crude oil and 1600 ppm nitrate for 1 week and incubated at room temperature while shaking at 100 rpm. A magnetic stirrer at the bottom of the reactor was stirring the culture at 40 to 50 rpm.

TABLE 2

Composition of the SL10 minimal salts medium - The pH of the medium was adjusted to between 7.4-7.8

| Growth component | Final Concentration | Chemical Source |
|---|---|---|
| Nitrogen | 18.7 µM | $NH_4Cl$ |
| Phosphorus | 3.7 µM | $KH_2PO_4$ |
| Magnesium | 984 µM | $MgCl_2 \cdot 6H_2O$ |
| Calcium | 680 µM | $CaCL_2 \cdot 2H_2O$ |
| Sodium chloride | 172 mM | NaCl |
| Trace metals | 670 µM | nitrilotriacetic acid |
| | 15.1 µM | $FeCl_2 \cdot 4H_2O$ |
| | 1.2 µM | $CuCl_2 \cdot 2H_2O$ |
| | 5.1 µM | $MnCL_2 \cdot 4H_2O$ |
| | 12.6 µM | $CoCl_2 \cdot 6H_2O$ |
| | 7.3 µM | $ZnCl_2$ |
| | 1.6 µM | $, H_3BO_3$ |
| | 0.4 µM | $Na_2MoO_4 \cdot 2H_2O$ |
| | 7.6 µM | $NiCl_2 \cdot 6H_2O$ |
| Selenium-tungstate | 22.8 nM | $Na_2SeO_3 \cdot 5H_2O$ |
| | 24.3 nM | $Na_2WO_4 \cdot 2H_2O$ |

TABLE 2-continued

Composition of the SL10 minimal salts medium - The pH of the medium was adjusted to between 7.4-7.8

| Growth component | Final Concentration | Chemical Source |
|---|---|---|
| PH buffer/Bicarbonate | 23.8 nM | NaHCO$_3$ |
| vitamins | 100 µg/L | vitamin B12 |
|  | 80 µg/L | p-amino-benzoic acid |
|  | 20 µg/L | nicotinic acid |
|  | 100 µg/L | calcium pantothenate |
|  | 300 µg/L | pyridoxine hydrochloride |
|  | 200 µg/L | thiamine-HCL•2H$_2$O |
|  | 50 µg/L | alpha-lipoic acid |
| Electron acceptor | 0.4 g/L | NaNO$_3$ |

The SL10 medium, supplemented with 3800 ppm nitrate, was pumped from the medium reservoir (FIG. 3: G) into the chemostat bioreactor by means of the feed syringe pump (KDS230 Syringe Pump, KD Scientific, Holliston, Mass.) (FIG. 3: D). A sampling port was attached to and inline with the feed syringe pump. A 5 mL Becton-Dickinson (BD) sterile plastic polypropylene syringe (FIG. 3: C) (Becton-Dickinson, Franklin Lakes, N.J.) was attached to the sampling port and had a double function: 1) as a sampling syringe for the input feed and 2) as a 5 psi pressure release valve for the feed syringe pump. The effluent from the chemostat bioreactor was pumped into an effluent reservoir (FIG. 3: L) by means of the effluent syringe pump (supra) (FIG. 3: O). A second sampling port was attached to and inline with the effluent syringe pump. The effluent sampling port also had a 5 mL BD sterile plastic polypropylene syringe (supra) attached (FIG. 3: P). Again, it functioned both as a sampling syringe for effluent and as a 5 psi pressure release valve for the effluent syringe pump.

Obtaining the Environmental Sample

In this disclosure, soil or water samples obtained from anaerobic and microaerophilic (aerobic microorganisms that requires lower levels of oxygen to survive) locations on an industrial site, which had been exposed to tar, creosol and polycyclic aromatic hydrocarbons (PAHs) were used for developing the microbial consortium. Soil samples were taken from locations where PAHs had been shown to be at elevated levels. Soil samples were placed in 500 mL brown bottles, filled to the top, sealed with no air space and, then shipped back to the lab on ice in a cooler. Once in the lab, the samples were placed in a Coy Type B anaerobic chamber (Coy Laboratories, Grass Lake, Mich.), filled with a specific anaerobic gas mixture (oxygen free anaerobic mix of hydrogen, carbon dioxide and nitrogen, 5%, 10% and 85%, respectively) for further processing.

Ion Chromatography

An ICS2000 chromatography unit (Dionex, Banockburn, Ill.) was used to quantitate nitrate and nitrite ions in the growth medium. Ion exchange was accomplished on an AS15 anion exchange column using a gradient of 2 to 50 mM potassium hydroxide. Standard curves were generated and used for calibrating nitrate and nitrite concentrations.

Genomic DNA Extractions from Bacterial Cultures

To extract genomic DNA from liquid bacterial cultures, cells were harvested and concentrated by filtration onto a 0.2 micron Supor® Filter (Pall Corp, Ann Arbor, Mich.) or by centrifugation. An aliquot (2-5 mL) of a bacterial culture was passed through a 0.2 micron, 25 mm filter disk in a removable cartridge holder using either vacuum or syringe pressure. The filters were removed and placed in the following lysis buffer (100 mM Tris-HCL, 50 mM NaCl, 50 mM EDTA, pH8.0) followed by agitation using a Vortex mixer. The following reagents were then added to a final concentration of 2.0 mg/mL lysozyme, 10 mg/mL SDS, and 10 mg/mL Sarkosyl to lyse the cells. After further mixing with a Vortex mixer, 0.1 mg/mL RNase and 0.1 mg/mL Proteinase K were added to remove the RNA and protein contaminants and the mixture was incubated at 37° C. for 1.0-2.0 hr. Post incubation, the filters were removed and samples were extracted twice with an equal volume of a phenol: chloroform: isoamyl:alcohol (25:24:1, v/v/v) and once with chloroform: isoamyl alcohol (24:1, v/v). One-tenth volume of 5.0M NaCl and two volumes of 100% ethanol were added to the aqueous layer and mixed. The tubes were frozen at −20° C. overnight and then centrifuged at 15,000×g for 30 min at room temperature to pellet chromosomal DNA. The pellets were washed once with 70% ethanol, centrifuged at 15,000×g for 10 min, dried, resuspended in 100 µL of de-ionized water and stored at −20° C. An aliquot of the extracted DNA was analyzed on an agarose gel to ascertain the quantity and quality of the extracted DNA.

Population Analysis of the Microorganisms of the Steady State Consortium and Parent Enrichment Cultures Using Cloned 16S rDNA Libraries Primer sets were chosen from Grabowski et al. (FEMS Microbiol. Ecol., 54: 427-443, 2005) to generate 16S rDNA of microbial species in DNA samples prepared from the consortium. The combination of forward primer (SEQ ID NO: 1) and reverse primers (SEQ ID NOs: 2 or 3) were chosen to specifically amplify the bacterial 16S rDNA sequences.

The PCR amplification mix included: 1.0× GoTaq PCR buffer (Promega), 0.25 mM dNTPs, 25 pmol of each primer, in a 50 µL reaction volume. 0.5 µL of GoTaq polymerase (Promega) and 1.0 µL (20 ng) of sample DNA were added. The PCR reaction thermal cycling protocol used was 5.0 min at 95° C. followed by 30 cycles of: 1.5 min at 95° C., 1.5 min at 53° C., 2.5 min at 72° C. and final extension for 8 min at 72° C. in a Perkin Elmer 9600 thermal-cycler (Waltham, Mass.). This protocol was also used with cells from either purified colonies or mixed species from enrichment cultures.

The 1400 base pair amplification products for a given DNA pool were visualized on 0.8% agarose gels. The PCR reaction mix was used directly for cloning into pPCR-TOPO4 vector using the TOPO TA cloning system (Invitrogen) as recommended by the manufacturer. DNA was transformed into TOP10 chemically competent cells selecting for ampicillin resistance. Individual colonies (~48-96 colonies) were selected and grown in microtiter plates for sequence analysis.

Plasmid Template Preparation

Large-scale automated template purification systems used Solid Phase Reversible Immobilization (SPRI, Agencourt, Beverly, Mass.) (DeAngelis, M. M., et al., Nucleic Acid Res., 23: 4742-4743, 1995). The SPRI® technology uses carboxylate-coated, iron-core, paramagnetic particles to capture DNA of a desired fragment length based on tuned buffering conditions. Once the desired DNA is captured on the particles, they can be magnetically concentrated and separated so that contaminants can be washed away.

The plasmid templates were purified using a streamlined SprintPrep™ SPRI protocol (Agencourt). This procedure harvests plasmid DNA directly from lysed bacterial cultures by trapping both plasmid and genomic DNA to the functionalized bead particles and selectively eluting only the plasmid DNA. Briefly, the purification procedure involves addition of alkaline lysis buffer (containing RNase A) to the bacterial culture, addition of alcohol based precipitation reagent including paramagnetic particles, separation of the magnetic particles using custom ring based magnetic separator plates, 5× washing of beads with 70% ETOH and elution of the plasmid DNA with water.

rDNA Sequencing, Clone Assembly and Phylogenetic DNA Analysis

DNA templates were sequenced in a 384-well format using BigDye® Version 3.1 reactions on ABI3730 instruments (Applied Biosystems, Foster City, Calif.). Thermal cycling was performed using a 384-well thermal-cycler. Sequencing reactions were purified using Agencourt's CleanSeq® dye-terminator removal kit as recommended by the manufacturer. The reactions were analyzed with a model ABI3730XL capillary sequencer using an extended run module developed at Agencourt. All sequence analyses and calls were processed using Phred base calling software (Ewing et al., Genome Res., 8: 175-185, 1998) and constantly monitored against quality metrics.

Assembly of rDNA Clones

A file for each rDNA clone was generated. The assembly of the sequence data generated for the rDNA clones was performed by the PHRAP assembly program (Ewing, et al., supra). Proprietary scripts generate consensus sequence and consensus quality files for greater than one overlapping sequence read.

Analysis of rDNA Sequences

Each assembled sequence was compared to the NCBI (rDNA database; ~260,000 rDNA sequences) using the BLAST algorithm program (Altschul, supra). The BLAST hits were used to group the sequences into homology clusters with ≧90% identity to the same NCBI rDNA fragment. The homology clusters were used to calculate proportions of particular species in any sample. Because amplification and cloning protocols were identical for analysis of each sample, the proportions could be compared from sample to sample. This allowed comparisons of population differences in samples taken for different enrichment selections and or at different sampling times for the same enrichment consortium culture.

Using Fingerprint Profiles to Characterize the Genetic Diversity of Complex Microbial Populations For characterizing microbial communities, DGGE fingerprint profiling (as described above) has been applied to identify and characterize the genetic diversity of complex microbial communities.

Targeting the variable sequence regions found in the 16S rRNA gene of microorganisms, Gerard Muyzer et al (supra) PCR amplified DNA sequence of the V3 region of 16S rRNA genes in a mixed population. As stated above, the region is flanked by two universal conserved primer regions one at 341 to 357 and the other at 518 to 534. A 40-bp GC-rich clamp in the 5' end of one of the forward PCR primers, which included: universal bacterial primer 357, universal archaeal primers, 341F1, 341F2, (SEQ NOs: 5, 7, and 9) were designed as dG•UB 357, dG•UA 341F1 and dG•UA 341F2, respectively (SEQ NOs: 6, 8, 10). As described above, the rDNA PCR products were electrophoresed on a linear gradient of denaturant ~30-60% (urea/formamide) which is parallel to the gel's electric field. DGGE gels were cast and electrophoresed using a D Gene™: Denaturing Electrophoresis System from BIORAD (Hercules, Calif.) following manufacturer's suggested protocols. rDNA samples were electrophoresed at a constant temperature of 60° C. for 8-24 hr at an appropriate voltage depending upon the 16S rDNA fragment population being analyzed. The electrophoresis buffer (1×TAE) was preheated to the target temperature in the D GENE chamber prior to electrophoresis. DGGE gels were stained with SYBR® GOLD nucleic acid stain (Invitrogen, Carlsbad, Calif.) for visualization and imaged on a Kodak imaging station 440. Multiple distinguishable bands, which were visualized in the separation pattern, were derived from the different species which constituted the POG1 population. Each band thereby, represented a distinct member of the population. Intensity of each band was most likely representative of the relative abundance of a particular species in the population, after the intensity was corrected for rRNA gene copies in one microbe versus the copies in others. The banding pattern also represented a DGGE profile or fingerprint of the populations. It is possible to identify constituents, which represent only 1% of the total population. Changes in the DGGE fingerprint profile of the population can signal changes in the parameters, e.g., the electron donors and electron acceptors that determine the growth and metabolism of the community as a whole. Thus the method described above provided a unique and powerful tool for conclusive identification of various microbial species within a mixed population.

Micro-Sand Column Oil Release Test

Isolated bacterial strains were examined for their ability to release oil from sand using a micro-sand column assay to visualize oil release. The micro-sand column consisted of an inverted glass Pasteur pipette containing the sand (10 to 100 microns) from the Alaskan North Slope oil reservoirs, which had been coated with crude oil and allowed to age for at least one week. Specifically, oil and sand were autoclaved separately to sterilize. Autoclaved sand samples are then transferred to a vacuum oven and dried at 180° C. for a minimum of one week. Sterilized dried sand and oil were then combined ~1:1 v/v in an anaerobic environment. The mixtures were stirred and allowed to age for a minimum of seven days in an anaerobic environment. The barrels of glass Pasteur pipette (5¾ inches) were cut to approximately half height (3 inches) and autoclaved. The cut end of the pipette was plunged into the sand/oil mix and the core filled to about 0.5 inches in height from the bottom of the pipette barrel. Next, the cut-end of the pipette, which contained the oil/sand mixture, was then placed (with the tapered end of the pipette pointing upward) into the 13 mm glass test tube. A test inoculum in four milliliters of minimal salts medium was added to the 13 mm glass tube. The apparatus was sealed inside 23×95 mm glass vials in an anaerobic environment. Oil released from the sand collects in the narrow neck of the Pasteur pipettes or as droplets on the surface of the sand layer. Cultures that enhanced release of oil over background (sterile medium) were presumed to have altered the interaction of the oil with the sand surface, demonstrating the potential to contribute to enhancing oil recovery in a petroleum reservoir.

Gas Chromatography

A flame ionization detector gas chromatography (GC FID) method was developed to analyze the wet sand from the sacrificed slim tubes for residual oil. An empirical relationship was determined based on North Slope sand and the intrinsic pore volume of packed sand, e.g., for 240 g of packed sand there was a pore volume of 64 mL. Weights of the individual sand samples were obtained and the oil on the sand was extracted with a known amount of toluene. A sample of this toluene with extracted oil was then analyzed by GC. The samples were analyzed using an Agilent Model 5890 Gas Chromatograph (Agilent, Wilmington, Del.) fitted with equipped with a flame photoionization detector, a split/splitless injector and capillary column, DB5 column (length 30 m×thickness 0.32 mm, film thickness 0.25 µm). An aliquot of 2 µL was injected with an analysis of 42 min. The injector temperature was at 300° C. and the detector temperature kept at 300° C. The carrier gas was helium, flowing at 2 mL/min. The FID detector gases were air and hydrogen flowing at 300 mL/min and 30 mL/min, respectively. A calibration curve was generated and used to determine the amount of oil in toluene on a weight percent basis. The calibration curve used 0.01, 0.1, 1, 5, and 10 wt % dissolved crude oil in toluene.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

In the present disclosure, it was intended to develop a steady state consortium of microorganisms, under anaerobic denitrifying conditions, using crude oil as the carbon source would maintain the relative abundance of various microbial species of the consortium hence allowing the consortium's optimal operation in modification of oil as compared to the ability of a single major species on the consortium as shown below.

Additional abbreviations used in the Examples below are as follows: "hr" means hour(s), "min" means minute(s), "L" means liter(s), "mL" means milliliters, "µL" means microliters, "g" means gram, "mg/mL" means milligram per milliliter, "M" means molar, "mM" means millimolar, "mmoles" means millimoles, "µmoles" means micromoles, pmoles means picomole(s), "° C." means degrees Centigrade, "bp" means base pair(s), "rpm" refers to revolutions per minute, "ppm" means part per million, "v/v" means volume for volume, "v/v/v" means volume for volume for volume, "w/v" means weight for volume, "mL/hr" means milliliter per hour, "mL/min" means milliliter per minute, "%" means percent, "g" means gravitational force, "nm" means nano meter, "psi" means per square inch, "sec" means second, "LB" means Luria Broth culture medium, "R2A" means Reasoner's 2A culture medium, "PCR" means polymerase chain reaction and "SDS" means sodium dodecyl sulfate.

Example 1

Enrichment of a Microbial Consortium on Targeted Oil, as the Carbon Source, Under Denitrifying Anaerobic Conditions Development of the Parent POG1 Consortium For the present Example, parent enrichment cultures and a screening protocol were developed to identify microbes capable of growth under anoxic conditions on either crude oil or its components as the sole source of carbon. Nitrate was used as the primary electron acceptor as described herein. Soil samples were diluted at a 1 to 10 w/v ratio (10 g in 100 mL medium) and incubated in the SL10 medium and 250 ppm sodium nitrate as the electron acceptor for 72 hr as described below. These soil suspensions were used as an inoculum into 60 mL serum vials that contained 2:1 v/v of the minimal salts medium (20 mL) and the autoclaved crude oil (10 mL). Inoculations for the enrichment cultures were performed in the Coy anaerobic glove bag as described above. All crude oil used in the present examples was from Milne Point, Prudhoe Bay on the Alaskan North Slop. The enrichment cultures were maintained anaerobically in the gas tight, septa sealed vials. These cultures were grown with moderate shaking (100 rpm) at ambient temperatures for weeks to months and sampled regularly for nitrate depletion and nitrite accumulation, visible turbidity and visible altered oil viscosity or oil adherence to glass. Cultures were occasionally sampled for analysis of their structure of microbial populations by rDNA sequence typing.

After 10 to 15 days, a biomass had developed in the original enrichment cultures that used crude oil for as the carbon source. Using these enrichments as an inoculum, a new series of enrichment parent subcultures were prepared. These second set of enrichment subcultures were designated "$1^{st}$ generation parent cultures" ($1^{st}$ gen) and were inoculated, capped and sealed in the anaerobic chamber. The 60 mL sub-culture serum vials contained 30 mL of the SL10 minimal salts medium (Table 2) with 250 ppm sodium nitrate and 15 mL autoclaved crude oil. The $1^{st}$ gen subcultures were grown with moderate shaking (100 rpm) at ambient temperatures for several weeks to three months and sampled regularly for nitrate depletion and nitrite accumulation, or in some cases, nitrite depletion. Changes observed included: visible turbidity, biofilms observed on the glass bottles or on the oil aqueous interface, oil-water emulsion, and visible altered oil viscosity or oil adherence to glass. Cultures were intermittently sampled for 16S rDNA phylogenetic typing.

When all available nitrates and produced-nitrites were reduced, the cultures were anaerobically subcultured into fresh medium supplemented with additional 250 ppm of sodium nitrate. Culture sampling was performed as before. After three months of growth and one to three subcultures, the resulting subculture populations were characterized using 16S rDNA typing (see above). The enrichment populations consisted of both facultative and strict anaerobes. These included various species of beta-Proteobacteria, primarily *Thauera* species and other species from: beta-Proteobacteria (Rhodocyclaceae), alpha-Proteobacteria, gamma-Proteobacteria, Deferribacteraceae, Bacteroidetes, Chloroflexi and Firmicutes/Clostridiales phyla (FIG. 1).

Since the individual enrichment populations were similar to each other, they were anaerobically pooled and inoculated into one liter of SL10 medium with 250 ppm sodium nitrate. The inoculated medium was then divided into 250 mL portions and each aliquot was inoculated into one of four 500 mL-serum bottles containing 125 mL of sterile crude oil. All bottles were anaerobically sealed. The cultures were referred to as "second-generation parent cultures" ($2^{nd}$ gen). Enrichments samples (designated EH36:1 A, EH36:1 B, EH36:1 C, EH36:1 D) (see Table 5) of the $2^{nd}$ gen cultures, were grown with moderate shaking (100 rpm) at ambient temperatures for several weeks and sampled regularly for nitrate and nitrite depletion. Nitrate was replenished to 250 ppm on four separate occasions. After the fourth depletion of nitrate, a 10 mL aliquot from one of the cultures was anaerobically inoculated and sealed into a 500 mL serum bottle containing 200 mL of SL10 medium with 2400 ppm sodium nitrate and 100 mL sterile crude oil, and designated as "third-generation parent" ($3^{rd}$ gen) (designated EH40:1 and EH44:1). The $2^{nd}$ gen cultures were continued on 250 ppm sodium nitrate, by removing 150 mL of culture and adding back 150 mL of sterile SL 10 minimal salts medium plus nitrate. All consortium cultures were incubated as described above for several weeks and regularly sampled for nitrate and nitrite depletion. After the $3^{rd}$ gen parent cultures had depleted the 2400 ppm sodium nitrate and all of the produced nitrite, all enrichment cultures were replenished with 2400 ppm sodium nitrate. After 190 days, all $2^{nd}$ and $3^{rd}$ gen enrichments, had reduced 6600 ppm nitrate. Cultures were then sampled for 16S rDNA phylogenetic typing to characterize their populations (FIG. 2). The members of population profiles of the enrichments were similar to what had been detected in previous enrichments.

Example 2

Monitoring Denitrification and Growth of a Steady State Consortium in a Chemostat Bioreactor Growth of the steady state POG1 consortium in the chemostat was monitored by optical density ($OD_{550}$) and nitrate reduction through taking daily samples for six weeks and then every second to third day for the next nine weeks. The nitrate and nitrite concentrations were determined by ion chromatography as described above. For the first two weeks, nitrate was fed at 14 ppm/day and thereafter at 69 ppm/day. Table 3 shows that equilibrium for nitrate reduction was reached after 9 days, where all of the nitrate, as well as the produced nitrite, were completely reduced. The culture completely reduced its nitrate supply for the next 97 days. Cell density equilibrium was reached after 32 days, two weeks after the nitrate feed had been increased by approximately five fold. The optical densities remained relatively constant for the next 74 days. At 35 to 43 days, the cells started to aggregate together and form biofilms at the oil-aqueous interface and oil water emulsions were observed. These culture characteristics made it difficult to obtain homogenous samples for growth measurements. Between 30 and 32 days into the experiment, the magnetic stirrer had stopped mixing and nitrate reduction was interrupted due to incomplete mixing of the culture in the bioreactor. Once the stirrer was restarted, nitrate was completely reduced within two days and the chemostat returned to equilibrium.

The steady state POG1 consortium consumed 6662 mg or 107.5 mol of nitrate in 106 days before nitrate reduction began to decrease as indicated by the presence of 27 ppm nitrite in the effluent after 106 days. The decreased rate of nitrate reduction seemed to indicate that the target component of the oil was becoming limiting. The denitrification of nitrate and its reduced nitrite to nitrogen is equivalent to 537.3 mmol of electrons consumed in crude oil oxidation (Rabus, R., et al., Arch Microbiol., 163: 96-103, 1995). It follows that the equivalent of 1.23 g of decane (8.6 mmol) was degraded to carbon dioxide. Therefore since 400 g of crude oil had been added to the chemostat bioreactor, theoretically approximately 0.31% of the oil had been dissimilated.

(Zeiss Axioskop 40, Carl Zeiss Micro Imaging, Inc, Thornwood, N.Y.). Microbes adhered to both the glass slide and the cover slip, demonstrating a positive hydrophobic response. This assay is a modified version of a procedure which indirectly measures hydrophobicity through the attachment of microbes to polystyrene plates (Pruthi, V. and Cameotra, S., Biotechnol. Tech., 11: 671-674, 1997). In addition, tiny, emulsified oil droplets (around 3 to 40 micron in diameter) were seen in the aqueous phase. Bacteria were also seen in a biofilm-like attachments to some of these emulsified oil droplets.

An aliquot (1 µL) of the steady state POG1 consortium with an emulsified oil drop was placed on a microscope slide and covered with a 20 mm-square No. 1 coverslip and examined using a phase imaging microscopy under an oil emersion lens at 1000× magnification. Microbes were also found in the oil phase in irregular "pockets" formed around aggregated bacteria.

Normally water droplets that are trapped in oil will take on a near circular shaped form. The aqueous-oil interface was moving toward the bottom of the slide, the bacteria were being captured at the interface within these aggregated hydrophobic forms, which were eventually "pinched-off" and left in the oil phase.

Microbes were also seen aggregated at the aqueous-oil interface. Bacteria are usually attracted to the interface but not in mass; they often stream quickly along the interface in one direction, one bacterium at a time. In this Example, the microbes were attracted to the interface as a non-motile aggregate of 30 to 50 microns wide. These observations demonstrate formation of a hydrophobic aggregate mass that may contribute to the formation of the biofilm at the aqueous-oil interface or with an oil/aqueous emulsion. This structure allows microbes to interact with oil and use some of its components as their carbon source.

The members of population profiles of the steady state were similar to what had been detected in previous enrichments and are shown in Table 4 below. There were 73 unique sequences (SEQ ID NOs: 15-87), which were grouped into seven classes of bacteria, which included alpha-Proteobacteria, beta-Proteobacteria, gamma-Proteobacteria, Deferribacteraceae, Spirochaetes, Bacteroidetes and Firmicutes/Clostridiales and Incertae sedis. The primary Genera

TABLE 3

Monitoring the optical density, nitrate feed and denitrification of the POG1 consortium in the chemostat bioreactor

| | Time (days) | | | | | | | | | | | |
|---|---|---|---|---|---|---|---|---|---|---|---|---|
| | 0 | 4 | 9 | 11 | 18 | 32 | 42 | 57 | 71 | 85 | 91 | 106 |
| $OD_{550}$ nm | .04 | 0.553 | 0.584 | 0.586 | 0.717 | 1.151 | 1.469 | 0.870 | 0.994 | 0.814 | 0.989 | 0.906 |
| Total Nitrate fed | 583.0 | 631.4 | 699.5 | 763.4 | 1045 | 2002 | 2654 | 3448 | 4337 | 5226 | 5636 | 6662 |
| Nitrate in Effluent ppm | 356.1 | 5.7 | 0 | 0 | 0 | 150 | 0 | 0 | 0 | 0 | 0 | 0 |
| Nitrite in Effluent ppm | 0 | 4.7 | 1.4 | 0 | 1 | 26.6 | 0 | 0 | 0 | 0 | 0 | 27.1 |

After 106 days of incubation, biofilm was seen on the glass of the bioreactor at or near the oil/aqueous fraction. The oil and aqueous fractions showed signs of emulsification. To observe emulsification, samples were examined using dark field and bright field phase microscopy at 400× magnification continued to be the beta-Proteobacteria, *Thauera. Thauera* strain AL9:8 was the dominant constituent. The diversity among the members of *Thauera/Azoarcus* group (Rhodocyclaceae) is significant since there are 31 unique 16S rDNA sequences in this group whose sequence differences occur in the primary signature regions of the variable regions. Also the Firmicutes/Clostridiales group are diverse with 16 unique sequences that include constituents from the Clostridia, Anaerovorax and Finegoldia genera.

into TOP10 chemically competent cells (Invitrogen) selecting for ampicillin resistance. Individual colonies (~48-96 colonies) were selected, grown in microtiter plates, prepared and submitted for sequence analysis as described above.

TABLE 4

Unique strains in consortium population based on 16S rDNA sequences

| Class | Genus | Highest Identity species | GenBank Accession No. | SEQ ID NO. |
|---|---|---|---|---|
| Beta-Proteobacteria | *Thauera* | *Thauera* strain AL9:8 | AJ315680 | 15 |
| | *Thauera* | *Thauera aromatica* | U95176 | 23, 24, 25, 26, 27, 28, 31, 32, 33, 34, 35, 36, 37, 38, 39, 40, 41, 67, 68 |
| | | *Thauera* sp. R26885 | AM084104 | 16, 19, 21, 30 |
| | *Azoarcus* | *Azoarcus* sp mXyN2 | X83533 | 17, 18, 22 |
| | | *Azoarcus* sp | AY570623 | 29, 54, 69, 86 |
| Gamma-Proteobacteria | *Azotobacter* | *Azotobacter beijerinckii* | AJ30831 | 20, 44, 46, 57, 70, 71, 72, 73, 74, 84, 85 |
| | *Pseudomonas* | *Pseudomonas putida* | EU930815 | 61, 80, 83 |
| | | *Pseudomonas pseudoalcligenes* | AB109012 | 60, 62 |
| Deferribacteraceae | *Deferribacter* | *Deferribacter desulfuricans* | AB086060 | 56, 77 |
| | *Flexistipes* | *Flexistipes* sp vp180 | AF220344 | 53, 58, 87 |
| Alpha-Proteobacteria | *Ochrobactrum* | *Ochrobactrum* sp mp-57 | AY331579 | 47 |
| | | *Ochrobactrum lupini* | AY457038 | 59 |
| Spirochaetes | *Spirochaeta* | *Spirochaeta* sp MET-_E | AY800103 | 43 |
| Bacteroidetes/Chloroflexi group | *Bacteroides* | Uncultured *Bacteroides/Cytophaga* | DQ238269 | 78 |
| Firmicutes Clostridiales | *Clostridia* | *Clostridium aceticum* | Y181183 | 76, 81 |
| | | *Clostridium chartatabidium* | X71850 | 55, 63, 75 |
| | *Anaerovorax* | *Anaerovorax* sp | EU498382 | 48, 49, 82, |
| | *Finegoldia* | *Finegoldia magna* | NC010376 | 42, 45, 50, 51, 52, 64, 65, 66, 79 |

Example 3

Population Analysis of the Steady State POG1 Consortium and Parent POG1 Cultures Using Cloned 16S rDNA Libraries DNA was extracted as described above from the $3^{rd}$ gen POG1 parent enrichment cultures and from the steady state POG1 chemostat culture samples and used to make cloned 16S rDNA libraries. Briefly, the 1400 base pair 16S rDNA amplification products for a given DNA pool were visualized on 0.8% agarose gels. The PCR reaction mix was used directly for cloning into pPCR-TOPO4 vector using the TOPO TA cloning system (Invitrogen) following the manufacturer's recommended protocol. DNA was transformed Results of 16S rDNA Sequence Analysis An overall 16S profile was compiled for $1^{st}$ gen, $2^{nd}$ gen and $3^{rd}$ gen parent POG1 cultures described herein. 16S rDNA profiles were also prepared from samples taken at several different time points from the ongoing steady state POG1 chemostat culture. A minimum of 48 16S rDNA clones for each enrichment and/or steady state time sample were sent to Agencourt for sequencing. The 16S rDNA sequence obtained was subsequently blasted (BLASTn) against the NCBI database. Sequences were grouped into homology clusters with at 90% identity to the same NCBI rDNA fragment. The homology clusters obtained for all parent POG1 cultures and steady state culture were used to calculate the proportions of particular bacteria in any sample. The populations' results obtained from selected parent enrichment cultures verses steady state is shown FIG. 4.

Analysis indicated that 50-90% of the total 16S rDNAs sequenced belonged to the taxonomic class of beta-Proteobacteria, family Rhodocyclaceae. Members of the beta-Proteobacteria phylum subclass, *Thauera* in particular, were the most abundant microorganism in the steady state POG1 consortium at any given time. Strains of Thauera have been shown to grow on oil and or oil constituents under anaerobic conditions without the need for additional nutrient supplementation (Anders et. al. Int. J. Syst. Evol. Microbiol., 45: 327-333, 1995).

Sequences belonging to the phyla *Bacteroides*, Firmicutes/Clostridiales (low G+C gram-positive bacteria), Deferribacteres and Spirochaetes represented between 4-23% of the microbial population and were consistently represented in the POG1 consortium steady state samples and its parent enrichments. The sample size of cloned 16S rDNAs (n=47) for steady state POG1 samples most likely under report the incidences of these organisms in the microbial population. Sequences affiliated with members of the gamma-Proteobacteria, Pseudomonadales, were also represented at a consistently low level in steady state POG1 time samples. This is in contrast to 16S rDNA profiles obtained for several of the initial parent enrichments of this consortium, which did not contain Pseudomonadales 16S rDNA sequences indicating that members of this phylotype may not be critical to steady state POG1 function in MEOR.

Lastly, a low level of sequences 3%) associated with phylotypes representing the Chloroflexi, Synergistes, delta-Proteobacteria, and alpha-Proteobacteria were frequently detected in the POG1 parent enrichment cultures.

In summary, the distribution of 16S rDNA sequences described for the steady state POG1 culture as well as the POG1 parent enrichment cultures describes the composition of organisms that define the steady state POG1 consortium. This selected composition of microorganisms presumably enhances the oil recovery.

Example 4

Partially Prophetic

Analysis of Microbial Community by DGGE

The distribution of individual microbial populations in the steady state POG1 consortium's community was analyzed using the 16S rDNA variable region analysis by DGGE. DNA for DGGE community fingerprinting was isolated from samples taken from the steady state POG1 consortium crude oil chemostat over the course of two months. PCR amplified fragments were generated using primers dG.UB357 and U518R for bacteria (SEQ ID NOs: 6 and 4) and dG.UA341 F1 and F2 with U518R for Archaea (SEQ ID NOs: 8, 10 and 4). This produced an approximately 200 bp sequence from the V3 region of the bacterial and archaeal 16S rDNA which were then analyzed by DGGE. In addition, PCR amplified fragments for the V4/V5 region of the bacterial and archaeal 16S rDNA sequences were also generated producing fragments of approximately 400 bp generated using primers dG.U519F and UB 936R for bacteria (SEQ ID NOs: 12 and 14) and dG.U519F and UA 9958R for Archaea (SEQ ID NOs: 12 and 15). These PCR fragments were separated by length and nucleotide sequence using DGGE.

Denaturing gradient gel electrophoresis for fingerprint profiling was performed using a Bio-Rad DGGE DCode System (Bio-Rad Laboratories, Hercules, Calif.). Fingerprint profiles of the amplified rRNA gene fragments were resolved by electrophoresis at 60° C. at 35 V for 16 hr on 8% (w/v) denaturing polyacrylamide gels containing from 30% to 60% denaturant concentration gradient (w/v, 7M urea and 40% formamide in 1×TAE (50×TAE: 2M Tris-Acetate, 50 mM EDTA, pH 8.0)). FIG. 5 is an example of a community DGGE profile of the V4/V5 region from time zero to 52 days. The profiles of the steady state POG1 consortium test samples (days, 0, 4, 28, 44, 52) on the left side appear to have stabilized after 28 days. The controls, on the right half of the gel, include the parent POG1 startup inoculum EHSO:1, and a strain *Thauera* strain AL9:8. Also included as controls were two strains isolated from the Alaskan North Slop production oil, strain LH4:15 (*Pseudomonas stutzeri*) and strain AL1:7 (Ochrobactrum sp., from the Brucellaceae family), respectively. The last two strains were chosen as controls to see if the steady state POG1 population included microorganisms that have been seen as major constituents of an oil field population. The major band in all consortium profiles (A) correlated with the band observed for strain *Thauera* AL9:8.

The second band, (B), which correlates with strain LH4:15, appears to decrease as a major constituent of the population in profiles from day 4 through day 52. The third band (C), which correlates with strain AL1:7, is less dense and is a constituent of the population in profiles for zero through 28 days. However, this band disappears in the later stages of denitrification. Bands D through L are also detectable as minor constituent bands of the population in all samples.

The Following Steps are Prophetic:

To identify these steady state POG1 profile bands, previously identified 16S rDNA clones representing constituents from the steady state POG1 consortium, may be applied to DGGE analysis to identify individual DGGE bands as was done to identify to bands A through C in FIG. 5. The V4/V5 region from cloned constituent 16S rDNAs may be used to analyze and identify the remaining bands D through L of the steady state POG1 DGGE profile. The results should closely correlate with the profile bands with major constituents of the consortium identified in the earlier 16S rDNA profile in FIG. 5. Table 4 in Example 2 lists the isolated 16S rDNA clones, obtained from POG1 16S rDNA population profile studies. The clones used to obtain these sequences may be used to generate PCR produces using the DGGE PCR products to identify and correlate the individual bands (A-L) of the DGGE 16S V4/V5 rDNA. Table 4 also includes the associated NCBI rDNA database Accession number ID obtained for these reference clones. These clones represent the major groups of bacteria comprising the POG1 consortium, which include beta-Proteobacteria, primarily *Thauera aromatica* species (Rhodocyclaceae), and from Pseudomonadales, Bacteroidaceae, Clostridiaceae, Incertae Sedis., Spirochete, Spirochaetaceaes., Deferribacterales Brucellaceae and Chloroflexaceae. PCR amplified fragments for the V4/V5 region of the microbial 16S rDNA may then be generated from both the cloned rDNA (plasmid DNA) that were identified as POG1 constituents and genomic DNA from correlated POG1 samplings as well as POG1 cultures started form frozen culture stocks. Miniprep DNA from POG1 16S rDNA clones may be prepared using a Qiagen Miniprep Kit (Valencia, Calif.) following the manufacturer's protocol. PCR amplified fragments from the V4/V5 region of approximately 400 bp may be generated using primers dG.U519F and UB 936R for bacteria (SEQ ID NOs: 12 and 14). Amplified fragments may be separated by length and nucleotide sequence using DGGE as described above.

Example 5

Prophetic

Long-Term Storage and Recovery of the Consortium for Field Inoculations

An important criterion for the application of any consortium is its viability and function following its long term storage. An aliquot (20 mL) of the steady state POG1 consortium was taken during the steady state growth in the chemostat. The 16S rDNA community sequence and a DGGE fingerprint profiles were performed to define the composition of the community at the sampling time point. The anaerobic sample was placed in a 15-20% glycerol mix (e.g., 150 μL of sterile degassed glycerol into 650 μL of the sample) in the Coy anaerobic chamber, dispensed into sterile 2.0 mL cryogenic polypropylene tubes and treated as described above. The tubes were quickly frozen on dry ice and stored in a −70° C. freezer until needed.

To test the viability of the steady state POG1 freezer culture or to use it as an inoculum, a cryogenic tube was removed from a −70° C. freezer and thawed on wet ice in an anaerobic chamber. An aliquot (50 μL) of the sample was used to start a seed culture for a larger inoculum for the chemostat bioreactor. The seed culture was inoculated into 20 mL of SL10 minimal medium supplemented with 300 ppm nitrate and 10 mL of the autoclaved-targeted crude oil in a 60 mL sterile serum bottle. The anaerobic bottle was sealed with a septum, incubated outside the anaerobic chamber at room temperature (20° C. to 25° C.) while shaking at 100 rpm on an orbital shaker. Culture turbidity, which is indicative of growth of the constituents of the consortium, was visually observed.

The Following Steps are Prophetic:

In addition, with a revived consortium, reduction of nitrate to nitrite is expected to occur after three days. When nitrate concentration reaches about 50 ppm or less, a sample may be taken for isolating the microbial community's DNA for 16S rDNA typing and DGGE fingerprint profiling. It would be expected that the DGGE profile and the 16S rDNA typing of the freezer seed culture would be similar to the profiles obtained for the steady state POG1 consortium. If the freezer culture were stable as expected, a seed culture may be prepared as an anaerobic inoculum for the chemostat bioreactor for nitrate assimilation analysis. The revived frozen consortium may also be used in an oil release sandpack or core flood assay. Furthermore, the revived frozen consortium may be used as a seed culture for a reservoir growth-injection tank, which is a vessel next to the oil well for holding the culture prior to injection or it can be used for growth of the culture prior to injecting the culture it the oil well.

Example 6

Oil Release Sandpack or Core Flood Assay

The application of the steady state POG1 consortium to a sandpack saturated with oil to evaluate its use in MEOR was done using the sandpack technique in an in-house developed Teflon® shrink-wrapped sandpack apparatus that simulates packed sand of sandstone. The process described herein was used for making two column sets, a "control" set and a "test" set, which was inoculated with the steady state POG1 consortium to test its efficacy to release oil from the sand column. Using a 1.1 inches thick, and 7 inches long Teflon heat shrink tube, an aluminum inlet fitting with Viton® O-ring was attached to one end of the tube using a heat gun. North Slope sand was added to the column which was vibrated with an engraver to pack down the sand and release trapped air. A second aluminum inlet fitting with Viton® O-ring was attached to the other end of the tube and sealed with heat a gun. The sandpack was then put in an oven at 275° C. for 7 min to evenly heat and shrink the wrap. The sandpack was removed and allowed to cool to room temperature. A second Teflon® heat shrink tube was installed over the original pack and heated in the oven as described above. After the column had cooled, a hose clamp was attached on the pack on the outer wrap over the O-ring and then tightened.

Both column sets (two columns in each set) were then flooded horizontally (at 60 mL/hr) with four pore volumes of "Brine" (sterile, anaerobic SL 10 medium, supplemented with 250 ppm nitrate and 3 mM phosphate buffer, pH 7.4) by means of a syringe pump and a 60 mL sterile plastic polypropylene syringe. Both sets of sandpacks were then flooded with anaerobic autoclaved crude oil to irreducible water saturation, which was predetermined to be two pore volumes. The oil was flooded, at a rate of 0.4 mL/hr, using a 10 mL sterile syringe and a syringe pump. The crude oil was aged on the sand by shutting-in the columns for seven days. One column set was anaerobically inoculated with one half of a pore volume at 0.4 mL/hr with a sample of the consortium removed anaerobically from the chemostat. Simultaneously a control inoculation using anaerobic "Brine" was also loaded on the control column set using the same procedure. The inocula were shut-in for incubation with the oil for seven days and the columns were then flooded with four pore volumes of anaerobic sterile "Brine" at 0.4 mL/hr.

At the conclusion of the production flood, the 7 inches long slim tubes were sacrificed into 5× one-inch sections labeled A-E. One inch was skipped at the beginning and at the exit of the slim tube to avoid edge effects during analysis. Section "A" came from the front end of the column. Sections A, C, and E were analyzed for residual oil saturation on the sand. The amount of oil on the wet sand from the sacrificed slim tubes for residual oil was measured by GC as described above. This value was multiplied by the total amount of toluene used to extract the oil resulting in the total amount of oil on the sand. The value obtained was then divided by the total sample weight to yield the percent of oil with respect to the total sample weight. The weight percent of oil of the sample was then multiplied by the ratio of the empirically derived characteristic of packed North Slope sand (total weight of sample after being flooded with brine divided by total sand weight, 1.27). This relationship is equal to the amount of oil on dry sand. This value was then multiplied by the ratio of the weight of the North Slope sand to the weight of the fluid trapped in the pore space of the sand, 3.75. The resulting value reflected the residual oil left on the sand in units of g of oil/g of total fluid in the pore space. As shown in Table 5, residual oil left on the column, in fractions A and C of the test column, were less than the controls confirming that the columns inoculated with the POG1 consortium released more oil than those that were not inoculated.

TABLE 5

Residual oil left on sand along the tube length after flooding with anaerobic sterile "Brine"

| Column Fraction | Average Percent Residual Oil on Sand | | |
|---|---|---|---|
| Assay Column | A | C | E |
| Test columns | 23.2% | 22.2% | 18.5% |
| Control columns | 27.3% | 22.3% | 18.2% |

Example 7

Ability of the Parent POG1 Consortium to Enhance Oil Release

The parent POG1 consortium cultures were examined for their ability to release oil from sand in a visual oil release assay using the microsand column described above. Inocula from early parallel enrichment cultures of the $2^{nd}$ gen parent POG1 consortium e.g., EH36:1 A, EH36:1 B, EH36:1 C, EH36:1 D each with ~250 ppm nitrate and one $3^{rd}$ gen culture (EH40:1) with high nitrate concentration (~1600 ppm) were tested in this assay. All enrichment cultures were grown anaerobically in the SL10 minimal salts medium (Table 2) using ACO oil as the carbon source and nitrate as the electron acceptor until turbidity was observed. All operations for preparation of the microsand columns, inoculation and growth were done in an anaerobic chamber using sterile techniques. A 4.0 mL aliquot of each inoculum was added to the 13 mm glass tubes either directly or diluted 1:2 with the minimal salts medium. The microsand columns (filled with oil-saturated sand as described above) were placed in each glass tube, immersed in the medium/cell inoculum with the tapered neck of the Pasteur pipettes pointing up. The outer vials were sealed in the anaerobic Coy chamber and allowed to incubate at ambient temperatures for the next several weeks. Each column was periodically checked for oil release. Cultures that enhanced release of oil over background (sterile medium) were presumed to have altered the interaction of the oil with the sand surface.

Oil released from the sand was visualized by the released oil collecting in the tapered neck of the Pasteur pipettes or forming droplets on the surface of the sand layer (FIG. 6). Oil release was observed for some of the POG1 parent enrichment cultures as rapidly as only 3 hr after inoculation. Oil release was also observed with the pure *Thauera* strain AL9:8, isolated from the $1^{st}$ gen POG1 parent enrichment cultures. Microsand columns were then observed over the course of several weeks. An increase in the initial amount of oil released was observed after 3 months of incubation. Uninoculated controls did not show visual release of oil over the course of the experiment. Triton® X-100 (Rohm & Haas Co), a non-ionic surfactant was used as a positive assay for the release of oil from sand. Table 6 lists the enrichment cultures tested and the observations of oil release after 7 days and 3 months incubation at ambient temperatures. These results indicated that the parent POG1 consortium interacted with oil-wet sands at the water/oil/sand interface and induced oil release from the sand's surface.

TABLE 6

Release of oil from microsand columns by enrichment cultures the steady state POG1 consortium

| Inoculum ID | dilution | Oil release T = 7 days | Oil release T = 3 months |
|---|---|---|---|
| Controls | | | |
| 1.0% Triton | no | +++ | ++++ |
| 1.0% Triton | ½ | ++ | +++ |
| NIC (medium) | no | – | – |
| Parent Environmental Enrichment Cultures | | | |
| EH36:1A | no | – | + |
| EH36:1B | no | + | ++ |
| EH36:1C | no | – | – |
| EH36:1C | ½ | + | + |
| EH36:1D | no | + | + |
| EH40:1 | no | – | +/– |

TABLE 6-continued

Release of oil from microsand columns by enrichment cultures the steady state POG1 consortium

| Inoculum ID | dilution | Oil release T = 7 days | Oil release T = 3 months |
|---|---|---|---|
| EH40:1 | ½ | + | + |
| *Thauera* strain AL9:8 | no | + | ++ |

1. Microsand columns were scored for oil release on a scale of 1 to 5 (+) in order of increased oil release;
(–) = no release of oil,
5 = complete release of oil from oil coated sand, as judged visually.

Example 8

The Ability of the Steady State Consortium to Release Oil from Sand Particles In order to screen the enrichment cultures for the ability to release oil from the nonporous silica medium, a microtiter plate assay was developed to measure the ability of the microbes to release oil/sand from oil-saturated North Slope sand. The assay is referred to as the LOOS test (Liberation of Oil Off Sand)

A microtiter plate assay was developed to measure the ability of the enrichment cultures and the consortium to release oil/sand from the oil-saturated Alaskan North Slope sand. North Slope sand was autoclaved and then dried under vacuum at 160° C. for 48 hr and 20 g of this dried sand was then mixed with 5 mL of autoclaved, degassed crude oil obtained from Milne point, North Slope. The oil-coated sand was then allowed to adsorb to the sand and age anaerobically at room temperature for at least a week. Microtiter plate assays were set up in the Coy anaerobic chamber. An aliquot of the undiluted steady state POG1 consortium (20 mL) was added into the wells of a 12-well microtiter plate. The POG1 was grown anaerobically in SL10 minimal medium with 2000 ppm sodium nitrate and North Slope crude oil. The control wells contained 2 mL of the SL10/2000 ppm $NaNO_3$ medium alone. Approximately 40 mg of oil-coated sand was then added to the center of each well. Samples were then monitored over time for the release and accumulation of "free" sand collecting in the bottom of the wells. Approximate diameters (in millimeters) of the accumulated total sand released were measured daily. A score of 3 mm and above indicated the microbes' potential to release oil from a nonporous silica medium such as sand.

Table 7 shows the relative sand release by the steady state POG1 consortium over a period of four weeks. After about 15 days, a 4 mm zone of released sand was observed in the bottom of the wells containing the steady state POG1 consortium. No release was observed for the medium alone. The results indicate that the steady state POG1 consortium has the potential to release oil from nonporous silicate substrates.

TABLE 7

Relative sand release by the steady state POG1 consortium over a period of four weeks (Values 2 or greater represent significant oil release)

| Sample | Day 1 | Day 6 | Day 16 | Day 24 |
|---|---|---|---|---|
| Steady state POG1 Consortium in SL10 medium | 0 | 2 | 4 | 4 |
| SL10 medium alone (control) | 0 | 0 | 0 | 0 |

Example 9

Emulsification of Crude Oil by the 3$^{Rd}$ Generation Parent Consortium

Microorganisms isolated from the crude oil reservoir sample, refinery environmental samples or environmental samples, containing crude oil or its components, have been shown to form a stable emulsion when grown on crude oil or at least low molecular weight organic acids (LMWOA), e.g., succinate, propionate, lactate, acetate and formate, as a carbon source. The purpose of this Example was to demonstrate the ability of microorganisms, either as isolated species or as a consortium, to form a stable emulsion in the crude oil organic phase.

To test the ability of the 3$^{rd}$ gen POG1 consortium to develop an oil-water phase emulsion, a test system was developed using pure strains isolated from sample exposed to crude oil or its organic components. The 3$^{rd}$ gen POG1 consortium was anaerobically grown in 32 mL SL10 medium with 1600 ppm NaNO$_3$ and 16 mL autoclaved crude oil (ACO). One sample contained only ACO as the carbon source. The other test samples contained 0.2% of one of the following LMWOAs e.g., succinate, propionate, lactate or acetate. Each emulsion test set contained one vial that had been inoculated with the parent consortium and the second vial that was the control. These were all sealed anaerobically and incubated for two weeks at room temperature. All inoculated samples had completely reduced the nitrate to nitrite after two weeks. An aliquot (2 mL) was removed from each vial and centrifuged at 14,000 rpm for 5 min in a Thermo 5519 microcentrifuge (Thermo Fisher Scientific Inc., Waltham, Mass.). The supernatant was added to a 4 mL Wheaton 225142 sample vial (Wheaton Science Products, Millville, N.J.) containing 1 mL of 2,2,4,4,6,8,8-heptamethyl-nonane (HMN) (Sigma-Aldrich, St Louis, Mo.) and a straight chain liquid organic solvent as the organic phase. The vials were securely fastened in a test tube-rack. The test tube-rack was placed on the lab bench, twelve inches away from the front of a Canon Powershot A530 digital camera, which was set to its macro picture function. A control picture was taken of the 10 vials to record their two liquid-phases in their initial state containing 2 mL of aqueous phase and 1 mL of organic phase. The vials and their contents were shaken by rapidly turning the rack head-over-tail 12 times. They were then placed down on the lab bench, at the same position where the control picture had been taken. A picture was taken immediately to record the initial emulsion state of each vial at time zero. To record the dissipation or stability over time of the emulsion formed by mixing the solutions, a picture was taken at 15 sec intervals until 300 sec had elapsed. The digital frames were studied to measure the dissipation of the emulsion. An emulsion was formed in the organic phase in all vials, including those that had not been inoculated with the consortium. The results are scored on a scale of 1 to 5 and shown in Table 8. The emulsion was scored on a scale of zero to five to indicate the thickness of the emulsion phase at the organic-water interface, where five was the finest and thickest emulsion. The emulsion became more coarse and thinner at the interface as the number decreased to one. A completely dissipated emulsion was scored zero. The non-inoculated controls dissipated either completely or almost completely within the first 15 seconds. An exception was observed with the control sample containing 0.2% acetate which remained somewhat stable for 75 sec before it completely dissipated. Cultures that had only ACO, crude oil plus acetate and ACO plus lactate were stable beyond 5 min and were actually stable for one hour. The inoculated sample containing lactate formed the most stable emulsion in thickness and fineness in comparison with all other samples. Succinate fed cultures did not form a stable emulsion, and propionate fed cultures formed a stable emulsion that was short lived, less than three minutes. These results indicate that several microorganisms within the consortium could emulsify crude oil and that this ability could be enhanced using low molecular weight organic acids supplements such as lactate and acetate.

TABLE 8

Modification of the autoclaved crude oil by the 3$^{rd}$ gen microorganisms in the presence of various low molecular weight organic acids (Values 2 or greater represent significant oil release and reflects the stability of the emulsion formed as described (5 > 4 > 3 > 2 > 1))

| Carbon source | Time (Min) | | | | | | | | | | | | | |
|---|---|---|---|---|---|---|---|---|---|---|---|---|---|---|
| | 0 | 15 | 30 | 45 | 60 | 75 | 90 | 105 | 120 | 150 | 180 | 210 | 240 | 300 |
| ACO + Inoculum | 5 | 3 | 2 | 2 | 2 | 2 | 2 | 2 | 2 | 1 | 1 | 1 | 1 | 1 |
| ACO only | 5 | 1 | 1 | 0 | 0 | 0 | 0 | 0 | 0 | 0 | 0 | 0 | 0 | 0 |
| ACO + Acetate + Inoculum | 5 | 5 | 3 | 3 | 3 | 3 | 3 | 3 | 3 | 1 | 1 | 1 | 1 | 1 |
| ACO + Acetate only | 5 | 5 | 3 | 2 | 2 | 2 | 0 | 0 | 0 | 0 | 0 | 0 | 0 | 0 |
| ACO + Propionate + Inoculum | 5 | 5 | 4 | 3 | 3 | 3 | 2 | 2 | 2 | 1 | 0 | 0 | 0 | 0 |
| ACO + Propionate only | 5 | 1 | 1 | 1 | 1 | 1 | 1 | 1 | 1 | 1 | 0 | 0 | 0 | 0 |
| ACO + Lactate + Inoculum | 5 | 4 | 4 | 4 | 4 | 3 | 3 | 3 | 3 | 3 | 3 | 3 | 3 | 3 |
| ACO + Lactate only | 5 | 0 | 0 | 0 | 0 | 0 | 0 | 0 | 0 | 0 | 0 | 0 | 0 | 0 |
| ACO + Succinate + Inoculum | 5 | 0 | 0 | 0 | 0 | 0 | 0 | 0 | 0 | 0 | 0 | 0 | 0 | 0 |
| ACO + Succinate only | 5 | 0 | 0 | 0 | 0 | 0 | 0 | 0 | 0 | 0 | 0 | 0 | 0 | 0 |

Example 10

Comparison of Growth of the POG1 Consortium and the Pure Strain *Thauera* AL9:8 on Targeted Oil Under Anaerobic Denitrifying Conditions Growth rates of the POG1 consortium and *Thauera* strain AL9:8 in oil enrichments under anaerobic denitrifying conditions were compared. *Thauera* strain AL9:8 represents the major microbial constituent of the POG1 consortium. Equivalent inocula of about $10^6$ cells of the consortium and the purified strain were used to inoculate 60 mL serum vials containing a 1:2 ratio of minimal salts medium to autoclaved crude oil under anaerobic conditions. SL10 medium (20 mL) (Table 2) with added nitrate (final concentration of 1100 to 1200 ppm) and 10.0 mL of autoclaved crude oil was used. The medium and crude oil had been deoxygenated by sparging with a mixture of nitrogen and carbon dioxide followed by autoclaving. All manipulations of bacteria were done in an anaerobic chamber. Samples were inoculated in triplicates, were incubated at ambient temperatures for several days and monitored for nitrate and nitrite levels for visible turbidity and gross visible changes to the integrity of the oil phase. POG1 inoculated vials consistently reduced nitrate at a faster rate than did pure cultures of *Thauera* strain AL9:8. Table 9 summarizes the results of the average nitrate reduction for the triplicate cultures of POG1 consortium verses pure cultures of Thauera strain AL9:8.

The POG1 consortium consistently developed biofilms under anaerobic denitrifying conditions in oil enrichments, a phenomenon not observed consistently in oil enrichments of *Thauera* strain AL9:8. Table 10 summarizes the results obtained for a set of oil enrichments cultured anaerobically as above in the SL10 medium and autoclaved crude oil (2:1) ratio. These cultures were initially incubated with ~300 ppm nitrate and then further supplemented with nitrate to a final concentration of 1100-1200 ppm for 6 days. Formation of a stable biofilm was observed on the surface of the glass vial [after 3-5 days]. These results underline the synergistic effect of various components of the POG1 consortium, whose major constituent is *Thauera* strain AL 9:8, on forming a biofilm compared to that formed by *Thauera* strain AL9:8 alone.

TABLE 9

Anaerobic growth in oil enrichments

| Microbial inoculum | Average[1] ppm Nitrate Day 0 | Average[1] ppm Nitrate Day 5 | Average[1] % of Nitrate reduced after 6 days |
|---|---|---|---|
| POG1 consortium | 971 | 117 | 95% |
| Strain AL9:8 | 1323 | 789 | 43% |

[1]Nitrate values are the average of three replicates per microbial test inoculum

TABLE 10

Biofilm formation of microbes in oil enrichments

| Microbial Oil Enrichments | Biofilm Formation |
|---|---|
| POG1 consortium | + |
| POG1 consortium | + |
| POG1 consortium | + |
| POG1 consortium | + |
| POG1 consortium | + |
| Strain AL9:8 | − |
| Strain AL9:8 | − |
| Strain AL9:8 | − |
| Strain AL9:8 | − |
| Strain AL9:8 | − |

We claim:

1. A method for enhancing oil recovery from a target oil reservoir using an enriched steady state microbial consortium comprising:
   (a) providing environmental samples comprising indigenous microbial populations of said target oil reservoir;
   (b) enriching for one or more steady state microbial consortium present in said samples wherein said enriching results in a consortium that utilizes crude oil as a carbon source under anaerobic, denitrifying conditions;
   (c) characterizing the enriched steady state consortium of (b) using 16S rDNA profiling;
   (d) assembling a consortium using the characterization of (c) comprising microbial genera comprising one or more *Thauera* species and any two additional species that are members of genera selected from the group consisting of Rhodocyclaceae, Pseudomonadales, Bacteroidaceae, Clostridiaceae, Incertae Sedis, Spirochaetaceaes, Deferribacterales, Brucellaceae and Chloroflexaceae;
   (e) identifying at least one relevant functionality of the consortium of (d);
   (f) storing said consortium at −70° C. without loss of said relevant functionality for oil recovery;
   (g) growing the enriched steady state consortium of (e) having at least one relevant functionality to a concentration sufficient for reservoir inoculation; and
   (h) inoculating the target reservoir with said sufficient concentration of the consortium of (f) and injection water comprising one or more electron acceptors wherein the consortium grows in the reservoir and wherein said growth promotes increased oil recovery.

2. The method of claim 1, wherein the indigenous microbial populations are environmental samples selected from the group consisting of:
   (a) sample from a target oil well in the form of injection water, waste water, production water; and
   (b) sample of soil that has been exposed to crude oil or any one or combination oil components including paraffins, aromatics, and asphaltenes.

3. The method of claim 1, wherein said enriching includes conditions comprising:

i) anaerobic and denitrifying conditions;
ii) a temperature of from about 15° C.-45° C.;
iii) a pH of from about 6 to about 9; and
iv) a nitrate concentration from about 25 ppm to about 7000 ppm.

4. The method of claim 1, wherein the electron acceptor in (g) is selected from the group consisting of oxygen, nitrate, iron (III), manganese (IV), sulfate, carbon dioxide, fumarate, malate, pyruvate and oxaloacetate, nitrite, ferric ion, sulfur, selenate, arsenate, and chloroethenes.

5. The method of claim 1, wherein the one or more *Thauera* species in (d) is one or more species selected from the group consisting of *Thauera* stain AL9:8, *Thauera aromatica, Thauera chlorobenzoica, Thauera vanillica* and *Thauera selenatis*.

6. The method of claim 1, wherein the microbial consortium of (f) is a consortium comprising at least one species from each of Firmicutes, Clostridiales, Deferribacterale, Spirochaetaceaes, Bacteroidaceae, Rhodocyclacea, Pseudomonadales, Brucellaceae and Chloroflexaceae.

7. The method of claim 1, wherein said relevant functionality of (e) is the ability of the consortium to cause any one or more of the following:
   (i) alternation of the permeability of the subterranean formation for improved water sweep efficiency;
   (ii) production of biosurfactants to decrease surface and interfacial tensions;
   (iii) change in wettability;
   (iv) production of polymers other than surfactants that facilitate mobility of petroleum;
   (v) production of low molecular weight acids which cause rock dissolution;
   (vi) generation of gases to increase formation pressure; and
   (vii) reduction in oil viscosity.

8. The method of claim 1, wherein the improved oil recovery occurs by a reduction in crude oil viscosity by growth of the enriched steady state consortium in the target reservoir, wherein said growth results in the production of any one or more of biosurfactants, carbon dioxide, or cell mass, or selective degradation of high molecular weight components in the oil well, or combinations thereof.

9. The method of claim 1, wherein said increased oil recovery occurs by growth of the enriched steady state consortium in a target reservoir without corrosion of oil recovery and processing hardware.

10. The method of claim 1, further comprising adding to the steady state microbial consortium of (d) one or more non-indigenous microorganisms having a relevant functionality for improving oil recovery.

11. The method of claim 10, wherein said one or more non-indigenous microorganisms is:
   a) selected from the group consisting of *Marinobacterium georgiense Thauera aromatica* T1, *Thauera chlorobenzoica Petrotoga miotherma Shewanella putrefaciens, Thauera aromatica* S100), *Comamonas terrigena* (*Microbulbifer hydrolyticus*, and mixtures thereof; and
   b) comprises a 16s rDNA sequence having at least 95% identity to a 16s rDNA sequence isolated from the microorganisms of (a).

\* \* \* \* \*

SEQUENCE LISTING

```
<160> NUMBER OF SEQ ID NOS: 87

<210> SEQ ID NO 1
<211> LENGTH: 20
<212> TYPE: DNA
<213> ORGANISM: artificial sequence
<220> FEATURE:
<223> OTHER INFORMATION: primer - 8F

<400> SEQUENCE: 1
agagtttgat ymtggctcag                                          20

<210> SEQ ID NO 2
<211> LENGTH: 19
<212> TYPE: DNA
<213> ORGANISM: artificial sequence
<220> FEATURE:
<223> OTHER INFORMATION: primer 1492R

<400> SEQUENCE: 2
ggwtaccttg ttacgactt                                           19
```

```
<210> SEQ ID NO 3
<211> LENGTH: 17
<212> TYPE: DNA
<213> ORGANISM: artificial sequence
<220> FEATURE:
<223> OTHER INFORMATION: primer 1407R

<400> SEQUENCE: 3 gacggggtg wgtrcaa                                                         17

<210> SEQ ID NO 4
<211> LENGTH: 17
<212> TYPE: DNA
<213> ORGANISM: artificial sequence
<220> FEATURE:
<223> OTHER INFORMATION: primer U518R

<400> SEQUENCE: 4
attaccgcgg ctgctgg                                                        17

<210> SEQ ID NO 5
<211> LENGTH: 17
<212> TYPE: DNA
<213> ORGANISM: artificial sequence
<220> FEATURE:
<223> OTHER INFORMATION: primer UB357F

<400> SEQUENCE: 5
cctacgggag gcagcag                                                        17

<210> SEQ ID NO 6
<211> LENGTH: 57
<212> TYPE: DNA
<213> ORGANISM: artificial sequence
<220> FEATURE:
<223> OTHER INFORMATION: primer dG UB 357F

<400> SEQUENCE: 6
cgcccgccgc gccccgcgcc cgtcccgccg ccccgcccg cctacgggag gcagcag             57

<210> SEQ ID NO 7
<211> LENGTH: 16
<212> TYPE: DNA
<213> ORGANISM: artificial sequence
<220> FEATURE:
<223> OTHER INFORMATION: primer UA 341F1

<400> SEQUENCE: 7 taygggcgc agcagg                                                          16

<210> SEQ ID NO 8
<211> LENGTH: 58
<212> TYPE: DNA
<213> ORGANISM: artificial sequence
<220> FEATURE:
<223> OTHER INFORMATION: primer dG UA341F1

<400> SEQUENCE: 8
cgcccgccgc gccccgcgcc cgtcccgccg ccccgcccg cctaygggc gcagcagg             58

<210> SEQ ID NO 9
<211> LENGTH: 18
<212> TYPE: DNA
<213> ORGANISM: artificial sequence
<220> FEATURE:
<223> OTHER INFORMATION: primer UA 341F2
```

```
<400> SEQUENCE: 9
cctacggggc gcagaggg                                                         18

<210> SEQ ID NO 10
<211> LENGTH: 58
<212> TYPE: DNA
<213> ORGANISM: artificial sequence
<220> FEATURE:
<223> OTHER INFORMATION: primer dG UA341F2

<400> SEQUENCE: 10
cgcccgccgc gccccgcgcc cgtcccgccg ccccgcccg cctacggggc gcagaggg             58

<210> SEQ ID NO 11
<211> LENGTH: 18
<212> TYPE: DNA
<213> ORGANISM: artificial sequence
<220> FEATURE:
<223> OTHER INFORMATION: primer U519F

<400> SEQUENCE: 11
cagcmgccgc ggtaatwc                                                         18

<210> SEQ ID NO 12
<211> LENGTH: 58
<212> TYPE: DNA
<213> ORGANISM: artificial sequence
<220> FEATURE:
<223> OTHER INFORMATION: primer U519F with 40 bp

<400> SEQUENCE: 12
cgcccgccgc gccccgcgcc cgtcccgccg ccccgcccg cagcmgccgc ggtaatwc             58

<210> SEQ ID NO 13
<211> LENGTH: 19
<212> TYPE: DNA
<213> ORGANISM: artificial sequence
<220> FEATURE:
<223> OTHER INFORMATION: primer UA958R

<400> SEQUENCE: 13
yccggcgttg amtccaatt                                                        19

<210> SEQ ID NO 14
<211> LENGTH: 23
<212> TYPE: DNA
<213> ORGANISM: artificial sequence
<220> FEATURE:
<223> OTHER INFORMATION: primer UB 939R

<400> SEQUENCE: 14
cttgtgcggg ccccgtcat ttc                                                   23

<210> SEQ ID NO 15
<211> LENGTH: 1510
<212> TYPE: DNA
<213> ORGANISM: unknown
<220> FEATURE:
<223> OTHER INFORMATION: Unknown clone from enriched environmental
      sample that by rDNA sequence analysis has highest identity to the
      genus Thauera

<400> SEQUENCE: 15
tggctcagat tgaacgctgg cggcatgctt tacacatgca agtcgaacgg cagcggggc           60 ttcggcctgc cggcgagtgg cgaacgggtg agtaatgcat cggaacgtgc ccatgtcgtg         120
```

-continued

```
ggggataacg tatcgaaagg tacgctaata ccgcatacgt cctgagggag aaagcggggg      180
atcttcggac ctcgcgcgat tggagcggcc gatgtcggat tagctagtag gtgaggtaaa      240
ggctcaccta ggcgacgatc cgtagcgggt ctgagaggat gatccgccac actgggactg      300
agacacggcc cagactccta cgggaggcag cagtggggaa ttttggacaa tgggcgcaag      360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacggcag agggggtgg  aattcctggt      660 gtagcagtga aatgcgtaga gatcaggagg aacaccgatg gcgaaggcag ccccctgggc      720
ctgtactgac gctcatgcac gaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aaggaattga      900
cggggacccg cacaagcggt ggatgatgtg gattaattcg atgcaacgcg aaaaacctta      960
cctacccttg acatgccagg aaccttgccg agaggcgagg gtgccttcgg gagcctggac     1020
acaggtgctg catggctgtc gtcagctcgt gtcgtgagat gttgggttaa gtcccgcaac     1080
gagcgcaacc cttgtcacta gttgccatca tttggttggg cactctagtg agactgccgg     1140
tgacaaaccg gaggaaggtg gggatgacgt caagtcctca tggcccttat gggtagggct     1200
tcacacgtca tacaatggtc ggtacagagg gttgccaagc cgcgaggtgg agccaatccc     1260
ttaaagccga tcgtagtccg gatcgtagtc tgcaactcga ctacgtgaag tcggaatcgc     1320
tagtaatcgc agatcagcat gctgcggtga atacgttccc gggtcttgta cacaccgccc     1380
gtcacaccat gggagtgggt ttcaccagaa gtaggtagct taaccttcgg gagggcgctt     1440 accacgtga  gattcatgac tggggtgaag tcgtaacaag gtaaccgaag gcgaattcg      1500 cggccgctaa                                                            1510
```

<210> SEQ ID NO 16
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      tThauera sp.R26885

<400> SEQUENCE: 16

```
tggctcagat tgaacgctgg cggcatgctt tacacatgca agtcgaacgg cagcgggggc       60
ttcggcctgc cggcgagtgg cgaacgggtg agtaatgcat cggaacgtgc ccatgtcgtg      120
ggggataacg tatcgaaagg tacgctaata ccgcatacgc cctgaggggg aaagcggggg      180
attcttcgga acctcgcgcg attggagcgg ccgatgtcgg attagctagt aggtgaggta      240
aaggctcacc taggcgacga tccgtagcgg gtctgagagg atgatccgcc acactgggac      300
tgagacacgg cccagactcc tacgggaggc agcagtgggg aattttggac aatgggcgca      360
agcctgatcc agccatgccg cgtgagtgaa gaaggccttc gggttgtaaa gctctttcgg      420
ccgggaagaa atcgcattct ctaatatagg atgtggatga cggtaccgga ctaagaagca      480
ccggctaact acgtgccagc agccgcggta atacgtaggg tgcgagcgtt aatctgaatt      540
actgggcgta aagcgtgcgc aggcggtttt gtaagacaga tgtgaaatcc ccgggcttaa      600
```

```
cctgggaact gcgtttgtga ctgcaaggct agagtacggc agagggggt ggaattcctg      660 gtgtagcagt gaaatgcgta gatatcggga ggatcaccta tggcgagggc agcccctgg      720 gcttgtactg acgctcatgc acgaaagcgt ggggagcaaa caggattaga taccctggta     780
gtccacgccc taaacgatgt cgactagtcg ttcggagcag caatgcactg agtgacgcag     840
ctaacgcgtg aagtcgaccg cctggggagt acggccgcaa ggttaaaact caaaggaatt     900
gacggggacc cgcacaagcg gtggatgatg tggattaatt cgatgcaacg cgaaaaacct     960
tacctaccct tgacatgtct ggaaccttgg tgagagccga gggtgccttc gggagccaga    1020
acacaggtgc tgcatggctg tcgtcagctc gtgtcgtgag atgttgggtt aagtcccgca    1080
acgagcgcaa cccttgtcat tagttgccat catttagttg ggcactctaa tgagactgcc    1140
ggtgacaaac cggaggaagg tggggatgac gtcaagtcct catggccctt atgggtaggg    1200
cttcacacgt catacaatgg tcggtacaga gggttgccaa gccgcgaggt ggagccaatc    1260
ccttaaagcc gatcgtagtc cggatcgtag tctgcaactc gactacgtga agtcggaatc    1320
gctagtaatc gcagatcagc atgctgcggt gaatacgttc ccgggtcttg tacacaccgc    1380
ccgtcacacc atgggagtgg gtttcaccag aagtaggtag cttaaccttc gggagggcgc    1440
ttaccacggt gagattcatg actggggtga agtcgtaaca aggtaaccg                1489

<210> SEQ ID NO 17
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus sp. mXyN1
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t

<400> SEQUENCE: 17
tggctcagat taaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgc cctgaggggg aaagcggggg     180
attcttcgga acctcgcgcg attggagcgg ccgatgtcgg attagctagt aggtgaggta     240
aaggctcacc taggcgacga tccgtagcgg gtctgagagg atgatccgcc acactgggac     300
tgagacacgc cccagactcc tacggagggc agcagtgggg aattttggac aatgggcgca     360
agcctgatcc agccatgccg cgtgagtgaa gaaggccttc gggttgtaaa gctctttcgg     420
ccgggaagaa atcgcattct ctaatatagg atgtggatga cggtaccgga ctaagaagca     480
ccggctaact acgtgccagc agccgcggta atacgtaggg tgcgagcgtt aatcggaatt     540
actgggcgta aagcgtgcgc aggcggtttt gtaagacaga tgtgaaatcc ccgggcttaa     600
cctgggaact gcgtttgtga ctgcaaggct agagtacggc agagggggt ggaattcctg      660 gtgtancant gaaatgcgta aatatcagga ggaacaccga tggcgaaggc agcccctgg      720 gcctgtactg acgctcatgc acgaaagggt ggggagcaaa caggattaga taccctggta     780
gtccacgccc taaacgatgt cgactagtcg ttcggagcag caatgcactg agtgacgcag     840
ctaacgcgtg aagtcgaccg cctggggagt acggccgcaa ggttaaaact caaaggaatt     900
```

-continued

| | |
|---|---|
| gacggggacc cgcacaagcg gtggatgatg tggattaatt cgatgcaacg cgaaaaacct | 960 |
| tacctacccct tgacatgcca ggaaccttgc cgagaggcga gggtgccttc gggagcctgg | 1020 |
| acacaggtgc tgcatggctg tcgtcagctc gtgtcgtgag atgttgggtt aagtcccgca | 1080 |
| acgagcgcaa cccttgtcac tagttgccat catttggttg ggcactctag tgagactgcc | 1140 |
| ggtgacaaac cggaggaagg tggggatgac gtcaagtcct catggcccctt atgggtaggg | 1200 |
| cttcacacgt catacaatgg tcggtacaga ggttgccaa gccgcgaggt ggagccaatc | 1260 |
| ccttaaagcc gatcgtagtc cggatcgtag tctgcaactc gactacgtga agtcggaatc | 1320 |
| gctagtaatc gcagatcagc atgctgcggt gaatacgttc ccgggtcttg tacacaccgc | 1380 |
| ccgtcacacc atgggagtgg gtttcaccag aagtaggtag cttaaccttc gggagggcgc | 1440 |
| ttaccacggt gagattcatg actggggtga agtcgtaaca aggtaaccg | 1489 |

```
<210> SEQ ID NO 18
<211> LENGTH: 1487
<212> TYPE: DNA
<213> ORGANISM: unknown
<220> FEATURE:
<223> OTHER INFORMATION: unkown clone
<220> FEATURE:
<221> NAME/KEY: misc_feature
<222> LOCATION: (939)..(939)
<223> OTHER INFORMATION: n is a, c, g, or t

<400> SEQUENCE: 18
```

| | |
|---|---|
| tggctcagat tgaacgctgg cggcatgctt tacacatgca agtcgaacgg cagcgggggc | 60 |
| ttcggcctgc cggcgagtgg cgaacgggtg agtaatgcat cggaacgtgc ccatgtcgtg | 120 |
| ggggataacg tatcgaaagg tacgctaata ccgcatacgt cctgagggag aaagcggggg | 180 |
| atcttcggac ctcgcgcgat tggagcggcc gatgtcggat tagctagtag gtgaggtaaa | 240 |
| ggctcaccta gcgcgacgat ccgtagcggg ctgagaggat gatccgccac actgggactg | 300 |
| agacacggcc cagactccta cgggaggcag cagtggggaa ttttggacaa tgggcgcaag | 360 |
| cctgatccag ccatgccgcg tgagtgaaga aggccttcgg gttgtaaagc tctttcggcc | 420 |
| gggaagaaat cgcattctct aatataggat gtggatgacg gtaccggact aagaagcacc | 480 |
| ggctaactac gtgccagcag ccgcggtaat acgtagggtg cgagcgttaa tcggaattac | 540 |
| tgggcgtaaa gcgtgcgcag gcggttttgt aagacagatg tgaaatcccc gggcttaacc | 600 |
| tgggaactgc gtttgtgact gcaaggctag agtacggcag aggggggtgg aattcctggt | 660 |
| gtaccagtga aatgcgtaaa gatcaagacg aacaccgatg gcgaaggcag cccccctgggc | 720 |
| ctgtactgac gctcatgcac aaaagcgtgg ggagcaaaca ggattagata ccctggtagt | 780 |
| ccacgcccta aacgatttcg actagtcgtt tggagcagca atgcactgag tgacgcagct | 840 |
| aacgcgtgaa gtcgaccgcc tggggagtac ggccgcaagg ttaaaactca aggaattga | 900 |
| cggggacccg cacaagcggt ggatgatgtg gattaattng atgcaacgcg aaaaacctta | 960 |
| cctacccttg acatgccagg aaccttgccg agaggcgagg gtgccttcgg agcctggac | 1020 |
| acaggtgctg catggctgtc gtcagctcgt gtcgtgagat gttgggttaa gtcccgcaac | 1080 |
| gagcgcaacc cttgtcatta gttgccatca tttagtttgg cactctaatg agactgccgg | 1140 |
| tgacaaaccg gaggaaggtg gggatgacgt caagtcatca tggcccttac ggcctgggct | 1200 |
| tcacacgtca tacaatggtc ggtacagagg gttgccaagc cgcgaggtgg agccaatccc | 1260 |
| ttaaagccga tcgtagtccg gatcgtagtc tgcaactcga ctacgtgaag tcggaatcgc | 1320 |
| tagtaatcgc agatcagcat gctgcggtga atacgttccc gggtcttgta cacaccgccc | 1380 |

| | |
|---|---|
| gtcacaccat gggagtgggt ttcaccagaa gtaggtagct taaccttcgg gagggcgctt | 1440 |
| accacggtga gattcatgac tggggtgaag tcgtaacaag gtaaccg | 1487 |

<210> SEQ ID NO 19
<211> LENGTH: 1489
<212> TYPE: DNA
<213> ORGANISM: unknown
<220> FEATURE:
<223> OTHER INFORMATION: Unknown clone from enriched environmental sample that by rDNA sequence analysis has highest identity to Thauera sp. R26885

<400> SEQUENCE: 19

| | |
|---|---|
| tggctcagat tgaacgctgg cggcatgctt tacacatgca agtcgaacgg cagcgggggc | 60 |
| ttcggcctgc cggcgagtgg cgaacgggtg agtaatgcat cggaacgtgc ccatgtcgtg | 120 |
| ggggataacg tatcgaaagg tacgctaata ccgcatacgt cctgagggag aaagcggggg | 180 |
| attcttcgga acctcgcgcg attggagcgg ccgatgtcgg attagctagt aggtgaggta | 240 |
| aaggctcacc taggcgacga tccgtagcgg gtctgagagg atgatccgcc acactgggac | 300 |
| tgagacacgg cccagactcc tacgggaggc agcagtgggg aattttggac aatgggggca | 360 |
| accctgatcc agccatgccg cgtgagtgaa gaaggccttc gggttgtaaa gctctttcgg | 420 |
| ccggaagaa atcgcgcact ctaacatagt gtgtggatga cggtaccgga ctaagaagca | 480 |
| ccggctaact acgtgccagc agccgcggta atacgtaggg tgcgagcgtt aatcggaatt | 540 |
| actgggcgta aagcgtgcgc aggcggtttt gtaagacgga tgtgaaatcc ccgggctcaa | 600 |
| cctgggaact gcgtttgtga ctgcaaggct agagtacggc agagggggt ggaattcctg | 660 |
| gtgtagcagt gaaatgcgta gatatcagga ggaacaccga tggcgaaggc agccccctgg | 720 |
| gcctgtactg acgctcatgc acgaaagcgt ggggagcaaa caggattaga taccctggta | 780 |
| gtccacgccc taaacgatgt cgactagtcg ttcggagcag caatgcactg agtgacgcag | 840 |
| ctaacgcgtg aagtcgaccg cctggggagt acggccgcaa ggttaaaact caaaggaatt | 900 |
| gacggggacc cgcacaagcg gtggatgatg tggattaatt cgatgcaacg cgaaaaacct | 960 |
| tacctaccct tgacatgtct ggaaccttgg tgagagccga gggtgccttc gggagccaga | 1020 |
| acacaggtgc tgcatggctg tcgtcagctc gtgtcgtgag atgttgggtt aagtcccgca | 1080 |
| acgagcgcaa cccttgtcac tagttgccat catttggttg gcactctag tgagactgcc | 1140 |
| ggtgacaaac cggaggaagg tggggatgac gtcaagtcct catggcccct atgggtaggg | 1200 |
| cttcacacgt catacaatgg tcggtacaga gggttgccaa gccgcgaggt ggagccaatc | 1260 |
| ccttaaagcc gatcgtagtc cggatcgtag tctgcaactc gactacgtga agtcggaatc | 1320 |
| gctagtaatc gcagatcagc atgctgcggt gaatacgttc ccgggtcttg tacacaccgc | 1380 |
| ccgtcacacc atgggagtgg gtttcaccag aagtaggtag cttaaccttc gggagggcgc | 1440 |
| ttaccacggt gagattcatg actggggtga agtcgtaaca aggtaaccg | 1489 |

<210> SEQ ID NO 20
<211> LENGTH: 894
<212> TYPE: DNA
<213> ORGANISM: unknown
<220> FEATURE:
<223> OTHER INFORMATION: Unknown clone from enriched environmental sample that by rDNA sequence analysis has highest identity to Azotobacter beijerinckii

<400> SEQUENCE: 20

| | |
|---|---|
| cttaacctgg gaactgcgtt tgtgactgca aggctagagt acggcagagg ggggtggaat | 60 |

| | |
|---|---|
| tccacgtgta acagtgaaat gcgtagagat gtggaggaac accgatggcg aaggcagccc | 120 |
| cctgggcctg tactgacgct catgcacgaa agcgtgggga gcaaacagga ttagataccc | 180 |
| tggtagtcca cgccctaaac gatgtcgact agtcgttcgg agcagcaatg cactgagtga | 240 |
| cgcagctaac gcgtgaagtc gaccgcctgg ggagtacggc cgcaaggtta aaactcaaag | 300 |
| gaattgacgg ggacccgcac aagcggtgga tgatgtggat taattcgatg caacgcgaaa | 360 |
| aaccttacct acccttgaca tgtctggaac cttggtgaga gccagggtg ccttcgggag | 420 |
| ccagaacaca ggtgctgcat ggctgtcgtc agctcgtgtc gtgagatgtt gggttaagtc | 480 |
| ccgcaacgag cgcaacccctt gtcactagtt gccatcattt ggttgggcac tctagtgaga | 540 |
| ctgccggtga caaaccggag gaaggtgggg atgacgtcaa gtcctcatgg cccttatggg | 600 |
| tagggcttca cacgtcatac aatggtcggt acagagggtt gccaagccgc gaggtggagc | 660 |
| caatcccta aagccgatcg tagtccggat cgtagtctgc aactcgacta cgtgaagtcg | 720 |
| gaatcgctag taatcgcaga tcagcatgct gcggtgaata cgttcccggg tcttgtacac | 780 |
| accgcccgtc acaccatggg agtgggtttc accagaagta ggtagcttaa ccttcgggag | 840 |
| ggcgcttacc acggtgagat tcatgactgg ggtgaagtcg taacaaggta accg | 894 |

<210> SEQ ID NO 21
<211> LENGTH: 1486
<212> TYPE: DNA
<213> ORGANISM: unknown
<220> FEATURE:
<223> OTHER INFORMATION: Unknown clone from enriched environmental
sample that by rDNA sequence analysis has highest identity to
Thauera sp. R26885

<400> SEQUENCE: 21

| | |
|---|---|
| tggctcagat tgaacgctgg cggcatgctt tacacatgca agtcgaacgg cagcggggc | 60 |
| ttcggcctgc cggcgagtgg cgaacggtg agtaatgcat cggaacgtgc ccatgtcgtg | 120 |
| ggggataacg tatcgaaagg tacgctaata ccgcatacgt cctgagggag aaagcggggg | 180 |
| atcttcggac ctcgcgcgat tggagcggcc gatgtcggat tagctagtag gtgaggtaaa | 240 |
| ggctcaccta ggcgacgatc cgtagcgggt ctgagaggat gatccgccac actgggactg | 300 |
| agacacggcc cagactccta cgggaggcag cagtggggaa ttttggacaa tgggcgcaag | 360 |
| cctgatccag ccatgccgcg tgagtgaaga aggccttcgg gttgtaaagc tctttcggcc | 420 |
| gggaagaaat cgtggtctct aacatgggcc atggatgacg gtaccggact aagaagcacc | 480 |
| ggctaactac gtgccagcag ccgcggtaat acgtagggtg cgagcgttaa tcggaattac | 540 |
| tgggcgtaaa gcgtgcgcag gcggttttgt aagacagatg tgaaatcccc gggctcaacc | 600 |
| tgggaactgc gtttgtgact gcaaggctag agtacgcag aggggggtgg aattcctggt | 660 |
| gtagcagtga aatgcgtaaa gatcaggagg aacaccgagg ggaaggcagc cccctgggcc | 720 |
| tgtatgaagg ctcaggcagg aaagcgtggg gagcaaacag gaatagatac cctggtagtc | 780 |
| cacgccctaa acgatgtcga ctagtcgttc ggagcagcaa tgcactgagt gacgcagcta | 840 |
| acgcgtgaag tcgaccgcct ggggagtacg gccgcaaggt taaaactcaa aggaattgac | 900 |
| ggggacccgc acaagcggtg gatgatgtgg attaattcga tgcaacgcga aaaaccttac | 960 |
| ctacccttga catgtctgga accttggtga gagccgaggg tgccttcggg agccagaaca | 1020 |
| caggtgctgc atggctgtcg tcagctcgtg tcgtgagatg ttgggttaag tcccgcaacg | 1080 |
| agcgcaaccc ttgtcactag ttgccatcat ttggttgggc actctagtga gactgccggt | 1140 |
| gacaaaccgg aggaaggtgg ggatgacgtc aagtcctcat ggcccttatg ggtagggctt | 1200 |

| cacacgtcat acaatggtcg gtacagaggg ttgccaagcc gcgaggtgga gccaatccca | 1260 |
| aaaagccgat cgtagtccgg atcgtagtct gcaactcgac tacgtgaagt cggaatcgct | 1320 |
| agtaatcgca gatcagcatg ctgcggtgaa tacgttcccg ggtcttgtac acaccgcccg | 1380 |
| tcacaccatg ggagtgggtt tcaccagaag taggtagctt aaccttcggg agggcgctta | 1440 |
| ccacggtgag attcatgact ggggtgaagt cgtaacaagg taaccg | 1486 |

<210> SEQ ID NO 22
<211> LENGTH: 1489
<212> TYPE: DNA
<213> ORGANISM: unknown
<220> FEATURE:
<223> OTHER INFORMATION: Unknown clone from enriched environmental
sample that by rDNA sequence analysis has highest identity to
Azoarcus sp. mXyN1

<400> SEQUENCE: 22

| tggctcagat tgaacgctgg cggcatgctt tacacatgca agtcgaacgg cagcgggggc | 60 |
| ttcggcctgc cggcgagtgg cgaacgggtg agtaatgcat cggaacgtgc ccatgtcgtg | 120 |
| ggggataacg tatcgaaagg tacgctaata ccgcatacgt cctgagggag aaagcggggg | 180 |
| attcttcgga acctcgcgcg attggagcgg ccgatgtcgg attagctagt aggtgaggta | 240 |
| aaggctcacc taggcgacga tccgtagcgg gtctgagagg atgatccgcc acactgggac | 300 |
| tgaggcacgg cccagactcc tacgggaggc agcagtgggg aattttggac aatgggggca | 360 |
| accctgatcc agccatgccg cgtgagtgaa gaaggccttc gggttgtaaa gctctttcgg | 420 |
| ccgggaagaa atcgcgcact ctaacatagt gtgtggatga cggtaccgga ctaagaagca | 480 |
| ccggctaact acgtgccagc agccgcggta atacgtaggg tgcgagcgtt aatcggaatt | 540 |
| actgggcgta aagcgtgcgc aggcggtttt gtaagacaga tgtgaaatcc ccgggctcaa | 600 |
| cctgggaact gcgtttgtga ctgcaaggct agagtacggc agaggggggt ggaattcctg | 660 |
| gtgtagcagt gaaatgcgta gatatcagga ggaacaccga tggcgaaggc agccccctgg | 720 |
| gcctgtactg acgctcatgc acgaaagcgt ggggagcaaa caggattaga taccctggta | 780 |
| gtccacgccc taaacgatgt cgactagtcg ttcggagcag caatgcactg agtgacgcag | 840 |
| ctaacgcgtg aagtcgaccg cctggggagt acggccgcaa ggttaaaact caaaggaatt | 900 |
| gacgggggacc cgcacaagcg gtggatgatg tggattaatt cgatgcaacg cgaaaaacct | 960 |
| tacctaccct tgacatgcca ggaaccttgc cgagaggcga gggtgccttc gggagcctgg | 1020 |
| acacaggtgc tgcatggctg tcgtcagctc gtgtcgtgag atgttgggtt aagtcccgca | 1080 |
| acgagcgcaa cccttgtcac tagttgccat catttggttg ggcactctag tgagactgcc | 1140 |
| ggtgacaaac cggaggaagg tggggatgac gtcaagtcct catggccttt atgggtaggg | 1200 |
| cttcacacgt catacaatgg tcggtacaga gggttgccaa gccgcgaggt ggagccaatc | 1260 |
| ccttaaagcc gattgtagtc cggatcgtag tctgcaactc gactacgtga agtcggaatc | 1320 |
| gctagtaatc gcagatcagc atgctgcggt gaatacgttc ccgggtcttg cacacaccgc | 1380 |
| ccgtcacacc atgggagtgg gtttcaccag aagtaggtag cttaaccttc ggagggcgc | 1440 |
| ttaccacggt gagattcatg actggggtga agtcgtaaca aggtaaccg | 1489 |

<210> SEQ ID NO 23
<211> LENGTH: 1487
<212> TYPE: DNA
<213> ORGANISM: unknown
<220> FEATURE:
<223> OTHER INFORMATION: Unknown clone from enriched environmental
sample that by rDNA sequence analysis has highest identity to Thauera aromatica

<400> SEQUENCE: 23

```
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg gttataaagc tctttcggcc     420
gggaagaaat cgtggtctct aacataggcc atggatgacg gtaccggact aagaagcacc     480
ggctaactac gtgccagcag ccgcggtaat acgtagggtg cgagcgttaa tcggagttac     540
tgggcgtaaa gcgtgcgcag gcggttttgt aagacagatg tgaaatcccc gggctcaacc     600
tgggaactgc gtttgtgact gcaaggctag agtacggcag agggggtgg aattcctggt     660
gtaacagtga aatgcgtaga gatcaggagg aacaccgatg gcgaaggcag cccctgggc     720
ctgtactgac gctcatgcac gaaagcgtgg ggagcaaaaa ggattaaata ccctggtagt     780
ccacgcccta aacgatgtcg actagtcgtt cggagcagca atgcactgag tgacgcagct     840
aacgcgtgaa gtcgaccgcc tggggagtac ggccgcaagg ttaaaactca aaggaattga     900
cggggacccg cacaagcggt ggatgatgtg gattaattcg atgcaacgcg aaaaacctta     960
cctaccttg acatgccagg aaccttgccg agaggcgagg gtgccttcgg gagcctggac    1020
acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccg                   1487
```

<210> SEQ ID NO 24
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 24

```
tggctcagat tgaacgctgg cggcatgctt tgcacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg gttgtaaagc tctttcggcc     420
```

```
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcagcc      600
tgggaactgc gtttgtgact gcaaggctag agtacggcag aaggggtgg aattcctggt       660 gtagcagtga aatgcgttga gatcaggagg aacaccgatg gcgaaggcag cccctgggc       720 ctgtactgac gctcatgtac aaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aaggaattga      900
cggggacccg cacaagcggt ggatgatgtg gattaattcg atgcaacgcg aaaaacctta      960
cctacccttg acatgccagg aaccttgccg agaggcgagg gtgccttcgg gagcctggac     1020
acaggtgctg catggctgtc gtcagctcgt gtcgtgagat gttgggttaa gtcccgcaac     1080
gagcgcaacc cttgtcacta gttgccatca tttggttggg cactctagtg agactgccgg     1140
tgacaaaccg gaggaaggtg gggatgacgt caagtcctca tggcccttat gggtagggct     1200
tcacacgtca taatggtc ggtacagagg gttgccaagc cgcgaggtgg agccaatccc       1260
ttaaagccga tcgtagtccg gatcgtagtc tgcaactcga ctacgtgaag tcggaatcgc     1320
tagtaatcgc agatcagcat gctgcggtga atacgttccc gggtcttgta cacaccgccc     1380
gtcacaccat gggagtgggt ttcaccagaa gtaggtagct taaccttcgg gagggcgctt     1440
accacggtga gattcatgac tggggtgaag tcgtaacaag gtaaccg                   1487
```

<210> SEQ ID NO 25
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 25

```
tggctcagat tgaacgctgg cggcatgctt tacacatgca agtcgaacgg cagcgggggc       60
ttcggcctgc cggcgagtgg cgaacgggtg agtaatgcat cggaacgtgc ccatgtcgtg      120
ggggataacg tatcgaaagg tacgctaata ccgcatacgt cctgagggag aaagcggggg      180
atcttcggac ctcgcgcgat tggagcggcc gatgtcggat tagctagtag gtgaggtaaa      240
ggctcaccta ggcgacgatc cgtagcgggt ctgagaggat gatccgccac actgggactg      300
agacacggcc cagactccta cgggaggcag cagtggggaa ttttggacaa tgggcgcaag      360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacggcag agggggtgg aattcctggt       660 ttagcagtga aatgcgtaga gatcaggagg aacaccgatg gcgaaggcag cccctgggc       720 ctgtactgac gctcatgcac gaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aaggaattga      900
cggggacccg cacaagcggt ggatgatgtg gattaattcg atgcaacgcg aaaaacctta      960
```

```
cctacccttg acatgccagg aaccttgccg agaggcgagg gtgccttcgg gagcctggac    1020
acaggtgctg catggctgtc gtcagctcgt gtcgtgagat gttgggttaa gtcccgcaac    1080
gagcgcaacc cttgtcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccg                  1487
```

<210> SEQ ID NO 26
<211> LENGTH: 1487
<212> TYPE: DNA
<213> ORGANISM: unknown
<220> FEATURE:
<223> OTHER INFORMATION: unknown clone

<400> SEQUENCE: 26

```
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa     240
ggctcaccta ggcgacgatc cgtagcgggt ctgagaggat gatccgccac actgggactg     300
agacacggcc cagactccta cgggaggcag cagtggggaa ttttggacaa tgggcgcaag     360
cctgatccag ccatgccgcg tgagtgaaga aggccttcgg gttgtaaagc tctttcggcc     420
gggaagaaat cgtggtctct aacataggcc atggatgacg gtaccggact aagaagcacc     480
ggctaactac gtgccagcag ccgcggtaat acgtagggtg cgagcgttaa tcggaattac     540
tgggcgtaaa gcgtgcgcag gcggttttgt aagacagatg tgaaatcccc gggctcaacc     600
tgggaactgc gtttgtgact gcaaggctag agtacgcag aggggggtgg aattcctggt     660
gtagcagtga atgcgtaga gatcaagagg aacaccgatg gcgaaggcag ccccctgggc     720
ctgtactgac gctcatgcac gaaagcgtgg ggagcaaaca ggattagata ccctggtagt     780
ccacgcccta aacgatgtcg actagtcgtt cggagcagca atgcactgag tgacgcagct     840
aacgcgtgaa gtcgaccgcc tggggagtac ggccgcaagg ttaaaactca aggaattga     900 cggggacccg cacaagcggt ggatgatgtg gattaattcg atgcaacgcg aaaaacctta     960
cctacccttg acctgccagg aaccttgccg agaggcgagg gtgccttcgg gagcctggac    1020
acaggtgctg catggctgtc gtcagctcgt gtcgtgagat gttgggttaa gtcccgcaac    1080
gagcgcaacc cttatcacta gttgccatca tttggttggg cactctagtg agactgccgg    1140
tgacaaaccg gaggaaggtg gggatgacgt caagtcctca tggcccttat gggtagggct    1200
tcacacgtca tacaatggtc ggtacagagg gttgccaagc cgcgaggtgg agccaatccc    1260
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgctt    1440
accacggtga gattcatgac tggggtgaag tcgtaacaag gtaaccg                  1487
```

<210> SEQ ID NO 27

<211> LENGTH: 1488
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 27

| | | | | | |
|---|---|---|---|---|---|
| tggctcagat | tgaacgctgg | cggcatgctt | tacacatgca | agtcgaacgg | cagcggggc | 60 |
| ttcggcctgc | cggcgagtgg | cgaacgggtg | agtaatgcat | cggaacgtgc | ccatgtcgtg | 120 |
| ggggataacg | tatcgaaagg | tacgctaata | ccgcatacgt | cctgagggag | aaagcggggg | 180 |
| atcttcggac | ctcgcgcgat | tggagcggcc | gatgtcggat | tagctagtag | gtgaggtaaa | 240 |
| ggctcaccta | ggcgacgatc | cgtagcgggt | ctgagaggat | gatccgccac | actgggactg | 300 |
| agacacggcc | cagactccta | cgggaggcag | cagtgggaa | ttttggacaa | tgggcgcaag | 360 |
| cctgatccag | ccatgccgcg | tgagtgaaga | aggccttcgg | gttgtaaagc | tctttcggcc | 420 |
| gggaagaaat | cgtggtctct | aacataggcc | atggatgacg | gtaccggact | aagaagcacc | 480 |
| ggctaactac | gtgccagcag | ccgcggtaat | acgtagggtg | cgagcgttaa | tcggaattac | 540 |
| tgggcgtaaa | gcgtgcgcag | gcggttttgt | aagacagatg | tgaaatcccc | gggctcaacc | 600 |
| tgggaactgc | gtttgtgact | gcaaggctag | agtacggcag | agggggtgg | aattcctggt | 660 |
| gtagcagtga | aatgcgtaga | gatcaagagg | aacaccgatg | gcggaagcag | cccccctggg | 720 |
| cctgtactga | cgttcatgca | cgaaagcgtg | gggagcaaac | aggattagat | acctggtaag | 780 |
| tccacgccct | aaacgatgtc | gactagtcgt | tcggagcagc | aatgcactga | gtgacgcagc | 840 |
| taacgcgtga | agtcgaccgc | ctggggagta | cggccgcaag | gttaaaactc | aaaggaattg | 900 |
| acggggaccc | gcacaagcgg | tggatgatgt | ggattaattc | gatgcaacgc | gaaaaacctt | 960 |
| acctacccctt | gacatgccag | gaaccttgcc | gagaggcgag | ggtgccttcg | ggagcctgga | 1020 |
| cacaggtgct | gcatggctat | cgtcagctcg | tgtcgtgaga | tgttgggtta | agtcccgcaa | 1080 |
| cgagcgcaac | ccttgtcact | agttgccatc | atttggttgg | gcactctagt | gagactgccg | 1140 |
| gtgacaaacc | ggaggaaggt | ggggatgacg | tcaagtcctc | atggccctta | tgggtagggc | 1200 |
| ttcacacgtc | atacaatggt | cggtacagag | ggttgccaag | ccgcgaggtg | gagccaatcc | 1260 |
| cttaaagccg | atcgtagtcc | ggatcgtagt | ctgcaactcg | actacgtgaa | gtcggaatcg | 1320 |
| ctagtaatcg | cagatcagca | tgctgcggtg | aatacgttcc | cgggtcttgt | acacaccgcc | 1380 |
| cgtcacacca | tgggagtggg | tttcaccaga | agtaggtagc | ttaaccttcg | ggagggcgct | 1440 |
| taccacggtg | agattcatga | ctggggtgaa | gtcgtaacaa | ggtaaccg | | 1488 |

<210> SEQ ID NO 28
<211> LENGTH: 1489
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 28

| | | | | | |
|---|---|---|---|---|---|
| tggctcagat | tgaacgctgg | cggcatgctt | tacacatgca | agtcgaacgg | cagcggggc | 60 |
| ttcggcctgc | cggcgagtgg | cgaacgggtg | agtaatgcat | cggaacgtgc | ccatgtcgtg | 120 |
| ggggataacg | tatcgaaagg | tacgctaata | ccgcatacgt | cctgagggag | aaagcggggg | 180 |
| atcttcggac | ctcgcgcgat | tggagcggcc | gatgtcggat | tagctagtag | gtgaggtaaa | 240 |

```
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag agggggtgg aatttctggt    660 gtagcagtaa aatgcgtaga gatcaagagg aacaccgtat ggcgaagcca gcccctgggg    720
cttgtactga cgttcatgca cgaaagggtg gggagcaaac aggattagat accctggta    780 gtccacgccc taaacgatgt cgactagtcg ttcggagcag caatgcactg agtgacgcag    840
ctaacgcgtg aagtcgaccg cctggggagt acggccgcaa ggttaaaact caaaggaatt    900
gacggggacc cgcacaagcg gtggatgatg tggattaatt cgatgcaacg cgaaaaacct    960
tacctaccct tgacatgcca ggaaccttgc cgagaggcga gggtgccttc gggagcctgg   1020
acacaggtgc tgcatggctg tcgtcagctc gtgtcgtgag atgttgggtt aagtcccgca   1080
acgagcgcaa cccttgtcac tagttgccat catttggttg ggcactctag tgagactgcc   1140
ggtgacaaac cggaggaagg tggggatgac gtcaagtcct catggccctt atgggtaggg   1200
cttcacacgt catacaatgg tcggtacaga gggttgccaa gccgcgaggt ggagccaatc   1260
ccttaaagcc gatcgtagtc cggatcgtag tctgcaactc gactacgtga agtcggaatc   1320
gctagtaatc gcagatcagc atgctgcggt gaatacgttc ccgggtcttg tacacaccgc   1380
ccgtcacacc atgggagtgg gtttcaccag aagtaggtag cttaaccttc gggagggcgc   1440
ttaccacggt gagattcatg actggggtga agtcgtaaca aggtaaccg              1489
```

<210> SEQ ID NO 29
<211> LENGTH: 749
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus ap. EH10

<400> SEQUENCE: 29

```
tggctcagat cgaacgctgg cggcatgctt tacacatgca agtcgaacgg cagcgggggc     60
ttcggcctgc cggcgagtgg cgaacgggtg agtaatgcat cggaacgtgc ccatgtcgtg    120
ggggataacg tatcgaaagg tacgctaata ccgcatacgc cctgagggg aaagcggggg    180 attcttcgga acctcgcgcg attggagcgg ccgatgtcgg attagctagt aggtgaggta    240
aaggctcacc taggcgacga tccgtagcgg gtctgagagg atgatccgcc acactgggac    300
tgagacacgg cccagactcc tacgggaggc agcagtgggg aattttggac aatggggca    360 accctgatcc agccatgccg cgtgagtgaa gaaggccttc gggttgtaaa gctctttcgg    420
ccgggaagaa atcgcgcact ctaacatagt gtgtggatga cggtaccgga ctaagaagca    480
ccggctaact acgtgccagc agccgcggta atacgtaggg tgcgagcgtt aatcggaatt    540
actgggcgta aagcgtgcgc aggcggtttt gtaagacaga tgtgaaatcc ccgggctcaa    600
cctgggaact gcgtttgtga ctgcaaggct agagtacggc agagggggt ggaattcctg    660 gtgtagcagt gaaatgcgta aatatcagga ggaacaccga tggcgaaggc agcccctgg    720 gcctgtactg acgctcatgc acgaaagcg                                      749
```

<210> SEQ ID NO 30
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera sp. R26885

<400> SEQUENCE: 30

| | | | | | | |
|---|---|---|---|---|---|---|
| tggctcagat | tgaacgctgg | cggcatgctt | tacacatgca | agtcgaacgg | cagcggggc | 60 |
| ttcggcctgc | cggcgagtgg | cgaacgggtg | agtaatgcat | cggaacgtgc | ccatgtcgtg | 120 |
| ggggataacg | tatcgaaagg | tacgctaata | ccgcatacgt | cctgagggag | aaagcggggg | 180 |
| atcttcggac | ctcgcgcgat | tggagcggcc | gatgtcggat | tagctagtag | gtgaggtaaa | 240 |
| ggctcaccta | ggcgacgatc | cgtagcgggt | ctgagaggat | gatccgccac | actgggactg | 300 |
| agacacggcc | cagactccta | cgggaggcag | cagtggggaa | ttttggacaa | tgggcgcaag | 360 |
| cctgatccag | ccatgccgcg | tgagtgaaga | aggccttcgg | gttgtaaagc | tctttcggcc | 420 |
| gggaagaaat | cgtggtctct | aacataggcc | atggatgacg | gtaccggact | aagaagcacc | 480 |
| ggctaactac | gtgccagcag | ccgcggtaat | acgtagggtg | cgagcgttaa | tcggaattac | 540 |
| tgggcgtaaa | gcgtgcgcag | gtggttttgt | aagacagatg | tgaaatcccc | gggctcaacc | 600 |
| tgggaactgc | gtttgtgact | gcaaggctag | agtacggcag | agggggtgg | aattcctggt | 660 |
| gtagcagtga | aatgcgtaaa | gatcaagagg | aacaccgatg | gcgaaggcag | ccccctgggc | 720 |
| ctgtactgac | gttcatgcac | gaaagcgtgg | ggagcaaaca | ggattagata | ccctggtagt | 780 |
| ccacgcccta | aacgatgtcg | actagtcgtt | cggagcagca | atgcactgag | tgacgcagct | 840 |
| aacgcgtgaa | gtcgaccgcc | tggggagtac | ggccgcaagg | ttaaaactca | aaggaattga | 900 |
| cggggacccg | cacaagcggt | ggatgatgtg | gattaattcg | atgcaacgcg | aaaaacctta | 960 |
| cctacccttg | acatgtctgg | aaccttggtg | agagccgagg | gtgccttcgg | gagccagaac | 1020 |
| acaggtgctg | catggctgtc | gtcagctcgt | gtcgtgagat | gttgggttaa | gtcccgcaac | 1080 |
| gagcgcaacc | cttgtcatta | gttgccatca | tttagttggg | cactctaatg | agactgccgg | 1140 |
| tgacaaaccg | gaggaaggtg | gggatgacgt | caagtcctca | tggcccttat | gggtagggct | 1200 |
| tcacacgtca | tacaatggtc | ggtacagagg | gttgccaagc | cgcgaggtgg | agccaatccc | 1260 |
| ttaaagccga | tcgtagtccg | gatcgtagtc | tgcaactcga | ctacgtgaag | tcggaatcgc | 1320 |
| tagtaatcgc | agatcagcat | gctgcggtga | atacgttccc | gggtcttgta | cacaccgccc | 1380 |
| gtcacaccat | gggagtgggt | tcaccagaa | gtaggtagct | taaccttcgg | gagggcgctt | 1440 |
| accacggtga | gattcatgac | tggggtgaag | tcgtaacaag | gtaaccg | | 1487 |

<210> SEQ ID NO 31
<211> LENGTH: 1487
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 31

| | | | | | | |
|---|---|---|---|---|---|---|
| tggctcagat | tgaacgctgg | cggcatgctt | tacacatgca | agtcgaacgg | cagcggggc | 60 |
| ttcggcctgc | cggcgagtgg | cgaacgggtg | agtaatgcat | cggaacgtgc | ccatgtcgtg | 120 |
| ggggataacg | tatcgaaagg | tacgctaata | ccgcatacgt | cctgagggag | aaagcggggg | 180 |

| atcttcggac | ctcgcgcgat | tggagcggcc | gatgtcggat | taactagtag | gtgaggtaaa | 240 |
| ggctcaccta | ggcgacgatc | cgtagcgggt | ctgagaggat | gatccgccac | actgggactg | 300 |
| agacacggcc | cagactccta | cgggaggcag | cagtggggaa | ttttggacaa | tgggcgcaag | 360 |
| cctgatccag | ccatgccgcg | tgagtgaaga | aggccttcgg | gttgtaaagc | tctttcggcc | 420 |
| gggaagaaat | cgtggtctct | aacataggcc | atggatgacg | gtaccggact | aagaagcacc | 480 |
| ggctaactac | gtgccagcag | ccgcggtaat | acgtagagtg | cgagcgttaa | tcggaattac | 540 |
| tgggcgtaaa | gcgtgcgcag | gcggttttgt | aagacagatg | tgaaatcccc | gggctcaacc | 600 |
| tgggaactgc | gtttgtgact | gcaaggctag | agtacggcag | agggggggtgg | aattcctggt | 660 |
| gtagcagtga | aatgcgtaaa | gatcaagagg | aacaccgatg | gcgaatgcaa | cccctgggc | 720 |
| ctgtactgac | gctcatgcac | gaaagcgtgg | ggagcaaaca | ggattagata | ccctggtagt | 780 |
| ccacgcccta | aacgatgtcg | actagtcgtt | cggagcagca | atgcactgag | tgacgcagct | 840 |
| aacgcgtgaa | gtcgaccgcc | tggggagtac | ggccgcaagg | ttaaaactca | aaggaattga | 900 |
| cggggacccg | cacaagcggt | ggatgatgtg | gattaattcg | atgcaacgcg | aaaaacctta | 960 |
| cctaccttg | acatgccagg | aaccttgccg | agaggcgagg | gtgccttcgg | gagcctggac | 1020 |
| acaggtgctg | catggctgtc | gtcagctcgt | gtcgtgagat | gttgggttaa | gtcccgcaac | 1080 |
| gagcgcaacc | cttgtcacta | gttgccatca | tttggttggg | cactctagtg | agactgccgg | 1140 |
| tgacaaaccg | gaggaaggtg | gggatgacgt | caagtcctca | tggcccttat | gggtagggct | 1200 |
| tcacacgtca | tacaatggtc | ggtacagagg | gttgccaagc | cgcgaggtgg | agccaatccc | 1260 |
| ttaaagccga | tcgtagtccg | gatcgtagtc | tgcaactcga | ctacgtgaag | tcggaatcgc | 1320 |
| tagtaatcgc | agatcagcat | gctgcggtga | atacgttccc | gggtcttgta | cacaccgccc | 1380 |
| gtcacaccat | gggagtgggt | ttcaccagaa | gtaggtagct | taaccttcgg | gagggcgctt | 1440 |
| accacggtga | gattcatgac | tggggtgaag | tcgtaacaag | gtaaccg | | 1487 |

<210> SEQ ID NO 32
<211> LENGTH: 1499
<212> TYPE: DNA
<213> ORGANISM: unknown
<220> FEATURE:
<223> OTHER INFORMATION: Unknown clone from enriched environmental
sample that by rDNA sequence analysis has highest identity to
Thauera aromatica

<400> SEQUENCE: 32

| cggttacctt | gttacgactt | caccccagtc | atgaatctca | ccgtggtaag | cgccctcccg | 60 |
| aaggttaagc | tacctacttc | tggtgaaacc | caccccatg | gtgtgacggg | cggtgtgtac | 120 |
| aagacccggg | aacgtattca | ccgcagcatg | ctgatctgcg | attactagcg | attccgactt | 180 |
| cacgtagtcg | agttgcagac | tacgatccgg | actacgatcg | gctttaaggg | attggctcca | 240 |
| cctcgcggct | tggcaaccct | ctgtaccgac | cattgtatga | cgtgtgaagc | cctacccata | 300 |
| agggccatga | ggacttgacg | tcatccccac | cttcctccgg | tttgtcaccg | gcagtctcac | 360 |
| tagagtgccc | aaccaaatga | tggcaactag | tgacaagggt | tgcgctcgtt | gcgggactta | 420 |
| acccaacatc | tcacgacacg | agctgacgac | agccatgcag | cacctgtgtc | caggctcccg | 480 |
| aaggcaccct | cgcctctcgg | caaggttcct | ggcatgtcaa | gggtaggtaa | ggttttcgc | 540 |
| gttgcatcga | attaatccac | atcatccacc | gcttgtgcgg | gtccccgtca | attcctttga | 600 |
| gttttaacct | tgcggccgta | ctccccaggc | ggtcgacttc | acgcgttagc | tgcgtcactc | 660 |
| agtgcattgc | tgctccgaac | gactagtcga | catcgtttag | ggcgtggact | accagggtat | 720 |

-continued

```
ctaatcctgt tgctccccca cgctttcgtg catgagcgtc agtacaggcc caggggggctg      780 ccttcgccat cggtgttcct cctgatctct gcgcatttca ctgctacacc aggaattcca      840 ccccctctg ccgtactcta gccttgcagt cacaaacgca gttcccaggt tgagcccggg       900
gatttcacat ctgtcttaca aaaccgcctg cgcacgcttt acgcccagta attccgatta     960
acgctcgcac cctacgtatt accgcggctg ctggcacgta gttagccggt gcttcttagt    1020
ccggtaccgt catccatggc ctatgttaga gaccacgatt tcttcccggc cgaaagagct    1080
ttacaacccg aaggccttct tcactcacgc ggcatggctg atcaggctt gcgcccattg      1140 tccaaaattc cccactgctg cctcccgtag gagtctgggc cgtgtctcag tcccagtgtg    1200
gcggatcatc ctctcagacc cgctacggat cgtcgcctag gtgagccttt acctcaccta    1260
ctagctaatc cgacatcggc cgctccaatc gcgcgaggtc cgaagatccc ccgctttctc    1320
cctcaggacg tatgcggtat tagcgtacct ttcgatacgt tatcccccac gacatgggca    1380
cgttccgatg cattactcac ccgttcgcca ctcgccggca ggccgaagcc cccgctgccg    1440
ttcgacttgc atgtgtaaag catgccgcca gcgttcaatc tgagccatga tcaaactct    1499
```

<210> SEQ ID NO 33
<211> LENGTH: 1429
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 33

```
tgaacgctgg cggcatgctt tacacatgca agtcgaacgg cagcgggggc ttcggcctgc       60
cggcgagtgg cgaacgggtg agtaatgcat cggaacgtgc ccatgtcgtg ggggataacg      120
tatcgaaagg tacgctaata ccgcatacgt cctgagggag aaagcggggg atttcggac      180 ctcgcgcgat tggagcggcc gatgtcggat tagctagtag gtgaggtaaa ggctcaccta     240
ggcgacgatc cgtagcgggt ctgagaggat gatccgccac actgggactg agacacggcc     300
cagactccta cgggaggcag cagtggggaa ttttggacaa tgggcgcaag cctgatccag     360
ccatgccgcg tgagtgaaga aggccttcgg gttgtaaagc tctttcggcc gggaagaaat     420
cgtggtctct aacataggcc atggatgacg gtaccggact aagaagcacc ggctaactac     480
gtgccagcag ccgcggtaat atgtaggggtg cgagcgttaa tcggaattac tgggcgtaaa    540
gcgtgcgcag gcggttttgt aagacagatg tgaaatcccc gggctcaacc tgggaactgc    600
gtttgtgact gcaaggctag agtacggcgg agggggggtgg aattcctggt gtagcagtga    660
aatgcgtaga gatcaggagg aacaccgatg gcgaaggcag ccccctgggc ctgtactgac    720
gctcatgcac gaaagcgtgg ggagcaaaca ggattagata ccctggtagt ccacgcccta    780
aacgatgtcg actagtcgtt cggagcagca atgcactgag tgacgcagct aacgcgtgaa    840
gtcgaccgcc tggggagtac ggccgcaagg ttaaaactca aaggaattga cggggacccg    900
cacaagcggt ggatgatgtg gattaattcg atgcaacgcg aaaaacctta cctacccttg    960
acatgccagg aaccttgccg agaggcgagg gtgccttcgg gagcctggac acaggtgctg    1020
catggctgtc gtcagctcgt gtcgtgagat gttgggttaa gtcccgcaac gagcgcaacc    1080
cttgtcacta gttgccatca tttggttggg cactctagtg agactgccgg tgacaaaccg    1140
gaggaaggtg gggatgacgt caagtcctca tggcccttat gggtagggct tcacacgtca    1200
tacaatggtc ggtacagagg gttgccaagc cgcgaggtgg agccaatccc ttaaagccga    1260
```

```
tcgtagtccg gatcgtagtc tgcaactcga ctacgtgaag tcggaatcgc tagtaatcgc      1320
agatcagcat gctgcggtga atacgttccc gggtcttgta cacaccgccc gtcacaccat      1380
gggagtgggt tcaccagaa gtaggtagct taaccttcgg gagggcgct                   1429
```

<210> SEQ ID NO 34
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 34

```
tggctcagat tgaacgctgg cggcatgctt tacacatgca agtcgaacgg cagcgggggc       60
ttcggcctgc cggcgagtgg cgaacgggtg agtaatgcat cggaacgtgc ccatgtcgtg      120
ggggataacg tatcgaaagg tacgctaata ccgcatacgc cctgagggag aaagcggggg      180
atcttcggac ctcgcgcgat tggagcggcc gatgtcggat tagctagtag gtgaggtaaa      240
ggctcaccta ggcgacgatc cgtagcgggt ctgagaggat gatccgccac actgggactg      300
agacacggcc cagactccta cgggaggcag cagtggggaa ttttggacaa tgggcgcaag      360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacggcag aggggggtgg aattcctggt      660
gtagcagtga aatgcgtaaa gatcaggagg aacaccgatg gcgaaggcag ccccctgggc      720
ctgtactgac gctcatgcac gaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aggaattga      900 cggggacccg cacaagcggt ggatgatgtg gattaatttg atgcaacgcg aaaaacctta      960 cctaccttg acatgccagg aaccttgccg agaggcgagg gtgccttcgg gagcctggac     1020
acaggtgctg catggctgtc gtcagctcgt gtcgtgagat gttgggttaa gtcccgcaac     1080
gagcgcaacc cttgtcacta gttgccatca tttggttggg cactctagtg agactgccgg     1140
tgacaaaccg gaggaaggtg gggatgacgt caagtcctca tggcccttat ggtagggct     1200 tcacacgtca tacaatggtc ggtacagagg gttgccaagc cgcgaggtgg agccaatccc     1260
ttaaagccga tcgtagtccg gatcgtagtc tgcaactcga ctacgtgaag tcggaatcgc     1320
tagtaatcgc agatcagcat gctgcggtga atacgttccc gggtcttgta cacaccgccc     1380
gtcacaccat gggagtgggt ttcaccagaa gtaggtagct taaccttcgg gagggcgct    1439
```

<210> SEQ ID NO 35
<211> LENGTH: 1440
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 35

```
tggctcagat tgaacgctgg cggcatgctt tacacatgca agtcgaacgg cagcgggggc       60
```

```
ttcggcctgc cggcgagtgg cgaacgggtg agtaatgcat cggaacgtgc ccatgtcgtg      120
ggggataacg tatcgaaagg tacgctaata ccgcatacgt cctgagggag aaagcggggg      180
atcttcggac ctcgcgcgat tggagcggcc gatgtcggat tagctagtag gtgaggtaaa      240
ggctcaccta ggcgacgatc cgtagcgggt ctgagaggat gatccgccac actgggactg      300
agacacggcc cagactccta cgggaggcag cagtgggaa ttttggacaa tgggcgcaag       360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacggcag agggggggtgg aattcctggt    660 gtagcagtga aatgcgtaga gatcaggagg aacaccgatg gcgaaggcag ccccctgggc      720
ctgtactgac gctcatgcac gaaagcctgg gggagcaaca ggattagata ccctggtaag     780
tccacgccct aaacgatgtc gactagtcgt tcggagcagc aatgcactga gtgacgcagc      840
taacgcgtga agtcgaccgc ctggggagta cggccgcaag gttaaaactc aaaggaattg      900
acggggaccc gcacaagcgg tggatgatgt ggattaattc gatgcaacgc gaaaaacctt      960 acctacccttt gacatgccag gaaccttgcc gagaggcgag ggtgccttcg ggagcctgga    1020
cacaggtgct gcatggctgt cgtcagctcg tgtcgtgaaa tgttgggtta agtcccgcaa     1080
cgagcgcaac ccttgtcact agttgccatc atttggttgg gcactctagt gagactgccg      1140
gtgacaaacc ggaggaaggt ggggatgacg tcaagtcctc atggccctta tgggtagggc     1200
ttcacacgtc atacaatggt cggtacagag ggttgccaag ccgcgaggtg gagccaatcc     1260
cttaaagccg atcgtagtcc ggatcgtagt ctgcaactcg actacgtgaa gtcggaatcg     1320
ctagtaatcg cagatcagca tgctgcggtg aatacgttcc cgggtcttgt acacaccgcc     1380
cgtcacacca tgggagtggg tttcaccaga agtaggtagc ttaaccttcg ggagggcgct     1440
```

<210> SEQ ID NO 36
<211> LENGTH: 1440
<212> TYPE: DNA
<213> ORGANISM: unknown
<220> FEATURE:
<223> OTHER INFORMATION: Unknown clone from enriched environmental
    sample that by rDNA sequence analysis has highest identity to
    Thauera aromatica

<400> SEQUENCE: 36

```
tggctcagat tgaacgctgg cggcatgctt tacacatgca agtcgaacgg cagcgggggc       60
ttcggcctgc cggcgagtgg cgaacgggtg agtaatgcat cggaacgtgc ccatgtcgtg     120
ggggataacg tatcgaaagg tacgctaata ccgcatacgt cctgagggag aaagcggggg     180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtgggaa ttttggacaa tgggcgcaag     360
cctgatccag ccatgccgcg tgagtgaaga aggccttcgg gttgtaaagt tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag aagggggtgg aattcctggt   660
```

| | |
|---|---|
| gtagcagtga aatgcgtaga gatcaggagg aacaccgatg gcgaaggcag ccccCttggg | 720 |
| cctgtactga cgctcatgca cgaaagcgtg gggagcaaac aggattagat accctggtag | 780 |
| tccacgccct aaacgatgtc gactagtcgt tcggagcagc aatgcactga gtgacgcagc | 840 |
| taacgcgtga agtcgaccgc ctggggagta cggccgcaag gttaaaactc aaaggaattg | 900 |
| acggggaccc gcacaagcgg tggatgatgt ggattaattc gatgcaacgc gaaaaacctt | 960 |
| acctacccTt gacatgccag gaaccttgcc gagaggcgag ggtgccttcg ggagcctgga | 1020 |
| cacaggtgct gcatggctgt cgtcagctcg tgtcgtgaga tgttgggtta agtcccgcaa | 1080 |
| cgagcgcaac ccttgtcact agttgccatc atttggttgg gcactctagt gagactgccg | 1140 |
| gtgacaaacc ggaggaaggt ggggatgacg tcaagtcctc atggccctta tgggtagggc | 1200 |
| ttcacacgtc atacaatggt cggtacagag ggttgccaag ccgcgaggtg gagccaatcc | 1260 |
| cttaaagccg atcgtagtcc ggatcgtagt ctgcaactcg actacgtgaa gtcggaatcg | 1320 |
| ctagtaatcg cagatcagca tgccgcggtg aatacgttcc cgggtcttgt acacaccgcc | 1380 |
| cgtcacacca tgggagtggg tttcaccaga agtaggtagc ttaaccttcg ggagggcgct | 1440 |

<210> SEQ ID NO 37
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 37

| | |
|---|---|
| tggctcagat tgaacgctgg cggcatgctt tacacatgca agtcgaacgg cagcgggggc | 60 |
| ttcggcctgc cggcgagtgg cgaacgggtg agtaatgcat cggaacgtgc ccatgtcgtg | 120 |
| ggggataacg tatcgaaagg tacgctaata ccgcatacgt cctgagggag aaagcggggg | 180 |
| atcttcggac ctcgcgcgat tggagcggcc gatgtcggat tagctagtag gtgaggtaaa | 240 |
| ggctcaccta gccgacgatc cgtagcgggt ctgagaggat gatccgccac actgggactg | 300 |
| agacacggcc cagactccta cgggaggcag cagtggggaa ttttggacaa tgggcgcaag | 360 |
| cctgatccag ccatgccgcg tgagtgaaga aggccttcgg gttgtaaagc tctttcggcc | 420 |
| gggaagaaat cgtggtctct aacataggcc atggatgacg gtaccggact aagaagcacc | 480 |
| ggctaactac gtgccagcag ccgcggtaat acgtagggtg cgagcgttaa tcggaattac | 540 |
| tgggcgtaaa gcgtgcgcag gcggttttgt aagacagatg tgaaatcccc gggctcaacc | 600 |
| tgggaactgc gtttgtgact gcaaggctag agtacggcag aggggggtgg aattcctggt | 660 |
| gtagcagtga aatgcgtaga gatcaagagg aacaccgatg gcgaaggcag cccCctgggc | 720 |
| ctgtactgac gttcatgcac gaaagcgtgg ggagcaaaca ggattagata ccctggtagt | 780 |
| ccacgcccta acgatgtcg actagtcgtt cggagcagca atgcactgag tgacgcagct | 840 |
| aacgcgtgaa gtcgaccgcc tggggagtac ggccgcaagg ttaaaactca aaggaattga | 900 |
| cggggacccg cacaagcggt ggatgatgtg gattaattcg atgcaacgcg aaaaacctta | 960 |
| cctacccttg acatgccagg aaccttgccg agaggcgagg gtgccttcgg gagcctggac | 1020 |
| acaggtgctg catggctgtc gtcagctcgt gtcgtgagat gttgggttaa gtcccgcaac | 1080 |
| gagcgcaacc cttgtcacta gttgccatca tttggttggg cactctagtg agactgccgg | 1140 |
| tgacaaaccg gaggaaggtg gggatgacgt caagtcctca tggcccttat gggtagggct | 1200 |
| tcacacgtca tacaatggtc ggtacagagg gttgccaagc cgcgaggtgg agccaatccc | 1260 |

```
ttaaagccga tcgtagtccg gatcgtagtc tgcaactcga ctacgtgaag tcggaatcgc    1320
tagtaatcgc agatcagcat gctgcggtga atacgttccc gggtcttgta cacaccgccc    1380
gtcacaccat gggagtgggt ttcaccagaa gtaggtagct taaccttcgg gagggcgct     1439
```

<210> SEQ ID NO 38
<211> LENGTH: 1439
<212> TYPE: DNA
<213> ORGANISM: unknown
<220> FEATURE:
<223> OTHER INFORMATION: Unknown clone from enriched environmental
     sample that by rDNA sequence analysis has highest identity to
     Thauera aromatica

<400> SEQUENCE: 38

```
tggctcagat tgaacgctgg cggcatgctt tacacatgca agtcgaacgg cagcgggggc      60
ttcggcctgc cggcgagtgg cgaacgggtg agtaatgcat cggaacgtgc ccatgtcgtg    120
ggggataacg tatcgaaagg tacgctaata ccgcatacgt cctgagggag agagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag agggggggtgg aattcctggt    660 gtagcagtga aatgcgtaga gatcaggagg aacaccgatg ggaaggcag ccccctgggc      720 ctgtactgac gctcatgcac gaaagcgtgg ggagcaaaca ggattagata cctggtagt      780 ccacgcccta aacgatgtcg actagtcgtt cggagcagca atgcactgag tgacgcagct    840
aacgcgtgaa gtcgaccgcc tggggagtac ggccgcaagg ttaaaactca aaggaattga    900
cggggacccg cacaagcggt ggatgatgtg gattaattcg atgcaacgcg aaaaacctta    960 cctaccccttg acatgccagg aaccttgccg agaggcgagg gtgccttcgg agcctggac   1020 acaggtgctg catggctgtc gtcagctcgt gtcgtgagat gttgggttaa gtcccgcaac   1080
gagcgcaacc cttgtcacta gttgccatca tttggttggg cactctagtg agactgccgg   1140
tgacaaaccg gaggaaggtg gggatgacgt caagtcctca tggcccttat gggtagggct   1200
tcacacgtca tacaatggtc ggtacagagg gttgccaagc cgcgaggtgg agccaatccc   1260
ttaaagccga tcgtagtccg gatcgtagtc tgcaactcga ctacgtgaag tcggaatcgc   1320
tagtaatcgc agatcagcat gctgcggtga atacgttccc gggtcttgta cacaccgccc   1380
gtcacaccat gggagtgggt ttcaccagaa gtaggtagct taaccttcgg gagggcgct    1439
```

<210> SEQ ID NO 39
<211> LENGTH: 1439
<212> TYPE: DNA
<213> ORGANISM: unknown
<220> FEATURE:
<223> OTHER INFORMATION: Unknown clone from enriched environmental
     sample that by rDNA sequence analysis has highest identity to
     Thauera aromatica

<400> SEQUENCE: 39

```
tggctcagat tgaacgctgg cggcatgctt tacacatgca agtcgaacgg cagcgggggc      60
```

-continued

```
ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag agggggtgg aattcctggt    660 gtatcagtga aatgcgtaaa gatcaagagg aacaccgatg gggaaggcag cccctgggc    720 ctgtactgac gttcatgcac gaaagcgtgg ggagcaaaca ggattagata ccctggtagt    780
ccacgcccta aacgatgtcg actagtcgtt cggagcagca atgcactgag tgacgcagct    840
aacgcgtgaa gtcgaccgcc tggggagtac ggccgcaagg ttaaaactca aggaattga    900 cggggacccg cacaagcggt ggatgatgtg gattaattcg atgcaacgcg aaaaacctta    960
cctacccttg acatgccagg aaccttgccg agaggcgagg gtgccttcgg gagcctggac   1020
acaggtgctg catggctgtc gtcagctcgt gtcgtgagat gttgggttaa gtcccgcaac   1080
gagcgcaacc cttgtcacta gttgccatca tttggttggg cactctagtg agactgccgg   1140
tgacaaaccg gaggaaggtg gggatgacgt caagtcctca tggcccttat gggtagggct   1200
tcacacgtca taatggtc ggtacagagg gttgccaagc cgcgaggtgg agccaatccc   1260
ttaaagccga tcgtagtccg gatcgtagtc tgcaactcga ctacgtgaag tcggaatcgc   1320
tagtaatcgt agatcagcat gctgcggtga atacgttccc gggtcttgta cacaccgccc   1380
gtcacaccat gggagtgggt ttcaccagaa gtaggtagct taaccttcgg gagggcgct   1439
```

<210> SEQ ID NO 40
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 40

```
tggctcagat tgaacgctgg cggcatgctt tacacatgca agtcgaacgg cagcgggggc     60
ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctcaccta ggcgacgatc cgtagcgggt ctgagaggat gatccgccac actgggactg    300
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacggcag agggggtgg aattcctggt    660
```

```
gtagcagtga aatgcgtaga gatcaggagg aacaccgatg gcgaaggcag ccccctgggc      720
ttgtactgac gctcatgcac gaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aaggaattga      900
cggggacccg cacaagcggt ggatgatgtg gattaattcg atgcaacgcg aaaaacctta      960
cctacccttg acatgccagg aaccttgccg agaggcgagg gtgccttcgg gagcctggac     1020
acaggtgctg catggctgtc gtcagctcgt gtcgtgagat gttgggttaa gtcccgcaac     1080
gagcgcaacc cttgtcacta gttgccatca tttggttggg cactctagtg agactgccgg     1140
tgacaaaccg gaggaaggtg gggatgacgt caagtcctca tggcccttat gggtagggct     1200
tcacacgtca tacaatggtc ggtacagagg gttgccaagc cgcgaggtgg agccaatccc     1260
ttaaagccga tcgtagtccg gatcgtagtc tgcaactcga ctacgtgaag tcggaatcgc     1320
tagtaatcgc agatcagcat gctgcggtga atacgttccc gggtcttgta cacaccgccc     1380
gtcacaccat gggagtgggt ttcaccagaa gtaggtagct taaccttcgg gagggcgct     1439
```

<210> SEQ ID NO 41
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica

<400> SEQUENCE: 41

```
tggctcagat tgaacgctgg cggcatgctt tacacatgca agtcgaacgg cagcgggggc       60
ttcggcctgc cggcgagtgg cgaacgggtg agtaatgcat cggaacgtgc ccatgtcgtg      120
ggggataacg tatcgaaagg tacgctaata ccgcatacgt cctgagggag aaagcggggg      180
atcttcggac ctcgcgcgat tggagcggcc gatgtcggat tagctagtag gtgaggtaaa      240
ggctcaccta gccgacgatc cgtagccggg ctgagaggat gatccgccac actgggactg      300
agacacggcc cagactccta cgggaggcag cagtggggaa ttttggacaa tgggcgcaag      360
cctgatccag ccatgccgcg tgagtgaaga aggccttcgg gttgtaaagc tctttcggcc      420
gggaagaaat cgtggtctct aacataggcc atggatgacg gtaccggact aagaagcacc      480
ggctaactac gtgccagcag ccgcggtaat acgtagggtg cgagcgttaa tcggaattac      540
tgggcgtaaa gcgtgcgcag gcggttttgt aagacagatg tgaaatcccc gggctcaacc      600
tgggaactgc gtttgtgact gcaaggctag agtacggcag agggggtgg aattcctggt       660 gtagcagtga aatgcgtaga gatcaggagg aacgccgatg gcgaagacag ccccctgggc      720
ctgtactgac gctcatgcac gaaagcgtgg ggagcaaaca ggattagata ccctggtagt      780
ccacgcccta aacgatgtcg actagtcgtt cggagcagca atgcactgag tgacgcagct      840
aacgcgtgaa gtcgaccgcc tggggagtac ggccgcaagg ttaaaactca aaggaattga      900
cggggacccg cacaagcggt ggatgatgtg gattaattcg atgcaacgcg aaaaacctta      960
cctacccttg acatgccagg aaccttgccg agaggcgagg gtgccttcgg gagcctggac     1020
acaggtgctg catggctgtc gtcagctcgt gtcgtgagat gttgggttaa gtcccgcaac     1080
gagcgcaacc cttgtcacta gttgccatca tttggttggg cactctagtg agactgccgg     1140
tgacaaaccg gaggaaggtg gggatgacgt caagtcctca tggcccttat gggtagggct     1200
tcacacgtca tacaatggtc ggtacagggg gttgccaagc cgcgaggtgg agccaatccc     1260
```

```
ttaaagccga tcgtagtccg gatcgtagtc tgcaactcga ctacgtgaag tcggaatcgc   1320
tagtaatcgc agatcagcat gctgcggtga atacgttccc gggtcttgta cacaccgccc   1380
gtcacaccat gggagtgggt ttcaccagaa gtaggtagct taaccttcgg gagggcgct    1439
```

<210> SEQ ID NO 42
<211> LENGTH: 1475
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 42

```
tggctcagga cgaacgctgg cggcgtgcct aacacatgca agtcgagcga agtgactctg     60
agagaaattt tcggatggat cgaagagtca tcttagcggc ggacgggtga gtaacgcgtg    120
agaaacctgc ctttcacaaa gggatagcct cgggaaactg ggattaatac cttatgaaac    180
tgaattaccg catggtagat cagtcaaagc gaataagcgg tgaaagatgg tctcgcgtcc    240
tattagctag ttggtgaggt aacggctcac caaggcttcg ataggtagcc ggcctgagag    300
ggtgaacggc cacactggaa ctgagacacg gtccagactc ctacgggagg cagcagtggg    360
gaatattgca caatggagga aactctgatg cagcgacgcc gcgtgaatga tgaaggcctt    420
cgggttgtaa agttctgtcc ttggggaaga taatgacggt acccaaggag gaagccccgg    480
ctaactacgt gccagcagcc gcggtaatac gtaggggcg agcgttgtcc ggaattattg     540
ggcgtaaagg gttcgcaggc ggtctgataa gtcagatgtg aaaggcgtag gctcaaccta    600
cgtaagcatt tgaaactgtc agacttgagt taaggagagg aaagtggaat tcctagtgta    660
gcggtgaaat gcgtagatat taggaggaat accagtggcg aagggsgact ttctggactt    720
atactgacgc tgaggaacga aagcgtgggg agsaaacagg attagatacc ctggtagttc    780
cacgccgtaa acgawgagtg ctaggtgktg ggggtcaaac ctcggtgccg caasctaacg    840
cattaagcac tccgcctggg gggtacgtac gcmagtatga aactcaaagg aattgacggg    900
gacccgcaca agcggtggat gatgtggatt aattcgatgc aacgcgaaaa accttaccta    960
cccttgacat gccaggaacc ttgccgagag gcgagggtgc cttcgggagc ctggacacag   1020
gtgctgcatg gctgtcgtca gctcgtgtcg tgagatgttg ggttaagtcc cgcaacgagc   1080 gcaaccttg tcactagttg ccatcatttg gttgggcact ctagtgagac tgccggtgac    1140 aaacggagg aagtgggga tgacgtcaag tcctcatggc cctatgggt agggcttcac      1200 acgtcataca atggtcggta cagagggttg ccaagccgcg aggtggagcc aatcccttaa    1260
agccgatcgt agtccggatc gtagtctgca actcgactac gtgaagtcgg aatcgctagt   1320
aatcgcagat cagcatgctg cggtgaatac gttcccgggt cttgtacaca ccgcccgtca   1380 ccatgggag gtgggtttca ccagaagtag gtagcttaac cttcgggaac cacggtgaga    1440
ttcatgactg gggtgaagtc gtaacaaggt aaccg                              1475
```

<210> SEQ ID NO 43
<211> LENGTH: 1481
<212> TYPE: DNA
<213> ORGANISM: unknown
<220> FEATURE:
<223> OTHER INFORMATION: Unknown clone from enriched environmental
      sample that by rDNA sequence analysis has highest identity to
      Spirochaeta sp. MET-E

<400> SEQUENCE: 43

| | |
|---|---|
| tggctcagaa cgaacgctgg cggcgcgttt aagcatgca agtcgagcgg caagggcctt | 60 |
| tgggccccta gagcggcgga cgggtgagta acacgtggac aatctgcccc ccggccgggg | 120 |
| atagcccagg gaaacctgga ttaataccgg atgagacggg acgcacgatg gtgcggtccg | 180 |
| ggaaaggcgc tgcggcgccg ccgggggatg agtccgcgac ccattagctg gacggcgggg | 240 |
| taaaggccca ccgtggcgac gatgggtagc cggcctgaga gggtggacgg ccacattgga | 300 |
| actgagacac ggtccagact cctacgggag gcagcagcta agaatcttcc gcaatgggcg | 360 |
| aaagcctgac ggagcgacgc cgcgtgaacg aagaaggccg tgaggttgta agttcttttt | 420 |
| cgggaggggg aattaccgtg gcagggaatg gccgcgggat gacgtgaatc cggaacaag | 480 |
| ccccggctaa ctacgtgcca gcagccgcgg taacacgtag ggggcgagcg ttgttcggaa | 540 |
| tcattgggcg taaagggcgt gcaggcggca ctgcaagtcc ggcgtgaaag accccggccc | 600 |
| aaccgggggg gtgcgctgga aactgcggtg cttgagtaca ggagggatg ccggaattcc | 660 |
| aggtgtaggg gtgaaatctg tagatatctg gaagaacacc gatggcgaag gcaggcatct | 720 |
| ggccatgtac tgacgctgag acgcgaaggt gcggggagca acaggtttta gataccctgg | 780 |
| tagtccgcac agtaaacgat gtgcaccagg gtggcggggg tagaaccccc ggtaccgtag | 840 |
| caaacgcatt aagtgcaccg cctggggagt atgctcgcaa gggtgaaact caaaggaatt | 900 |
| gacgggggcc cgcacaagcg gaggagcatg tggtttaatt cgatgatacg cgaggaacct | 960 |
| tacctgggct cgaacgtaag atgactgtag gtgaaagctt acatctcttc ggagcatttt | 1020 |
| acgaggtgct gcatggttgt cgtcagctcg tgccgtgagg tgtcgggtta agtcccataa | 1080 |
| cgagcgcaac ccctacccttt agttgccatc aggtaatgct ggggactcta aggaactgc | 1140 |
| ctacgcaagt agtgaggaag gcggggatga cgtcaaatca gcacggccct tacgtccagg | 1200 |
| gctacacacg tgctacaatg gccgatacag agggcagcta cctggtgaca ggatgcaaat | 1260 |
| ctccaaagtc ggtctcagtt cggatcggag tctgcaaccc gactccgtga agttggattc | 1320 |
| gctagtaatc gcgcatcagc catggcgcgg tgaatacgtt cccgggcctt gtacacaccg | 1380 |
| cccgtcaagc catggaagct gggggggacct aaagtcgata accgcaagga gtcgcctagg | 1440 |
| gtaaaaccag tgactggggc taagtcgtaa caaggtaacc g | 1481 |

<210> SEQ ID NO 44
<211> LENGTH: 1488
<212> TYPE: DNA
<213> ORGANISM: unknown
<220> FEATURE:
<223> OTHER INFORMATION: Unknown clone from enriched environmental
sample that by rDNA sequence analysis has highest identity to
Azotobacter beijerinckii

<400> SEQUENCE: 44

| | |
|---|---|
| tggctcagat tgaacgctgg cggcaggcct aacacatgca agtcgagcgg atgagtggag | 60 |
| cttgctccat gattcagcgg cggacgggtg agtaatgcct aggaatctgc ctggtagtgg | 120 |
| gggacaacgt ttcgaaagga acgctaatac cgcatacgtc ctacgggaga aagtgggga | 180 |
| tcttcggacc tcacgctatc agatgagcct aggtcggatt agctagttgg cgaggtaaag | 240 |
| gctcaccaag gcgacgatcc gtaactggtc tgagaggatg atcagtcaca ctggaactga | 300 |
| gacacggtcc agactcctac gggaggcagc agtggggaat attggacaat gggcgaaagc | 360 |
| ctgatccagc catgccgcgt gtgtgaagaa ggccttcggg ttgtaaagct ctttcggccg | 420 |
| ggaagaaatc gtggtctcta acataggcca tggatgacgg taccggacta agaagcaccg | 480 |
| gctaactacg tgccagcagc cgcggtaata cgtagggtgc gagcgttaat cggaattact | 540 |

```
gggcgtaaag cgtgcgcagg cggttttgta agacagatgt gaaatccccg ggctcaacct    600
gggaactgcg tttgtgactg caaggctaga gtacggcaga gggggtgga attcctggtg    660 tagcagtgaa atgcgtagag atcaggagga acaccgatgg cgaaggcagc cccctgggcc    720
tgtactgacg ctcatgcacg aaagcgtggg agcaaacag gattagatac cctggtagtc    780
cacgccctaa acgatgtcga ctagtcgttc ggagcagcaa tgcactgagt gacgcagcta    840
acgcgtgaag tcgaccgcct ggggagtacg gccgcaaggt taaaactcaa aggaattgac    900
ggggacccgc acaagcggtg gatgatgtgg attaattcga tgcaacgcga aaaaccttac    960
ctacccttga catgccagga accttgccga gaggcgaggg tgccttcggg agcctggaca   1020
caggtgctgc atggctgtcg tcagctcgtg tcgtgagatg ttgggttaag tcccgcaacg   1080
agcgcaaccc ttgtcactag ttgccatcat ttggttgggc actctagtga gactgccggt   1140
gacaaaccgg aggaaggtgg ggatgacgtc aagtcctcat ggcccttatg ggtagggctt   1200
cacacgtcat acaatggtcg gtacagaggg ttgccaagcc gcgaggtgga gccaatccct   1260
taaagccgat cgtagtccgg atcgtagtct gcaactcgac tacgtgaagt cggaatcgct   1320
agtaatcgca gatcagcatg ctgcggtgaa tacgttcccg ggccttgtac acaccgcccg   1380
tcacaccatg agagttggca atacccgaag tccgtggggc aaccgtttac ggagccagcg   1440
gccgaaggta gggtcagcga ttggggtgaa gtcgtaacaa ggtaaccg               1488

<210> SEQ ID NO 45
<211> LENGTH: 1481
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 45
cggttacctt gttacgactt caccccagtc attgccccta ccttcgacag ctgccccctt     60
ttatggttag ctcactggct tcgggtattg acaactccca tggtgtgacg ggcggtgtgt    120
acaagacccg ggaacgcatt caccgcggca ttctgatccg cgattactag caactccgac    180
ttcatgcagg cgagttgcag cctgcaatcc gaactgggat cggcttttag agatttgctt    240
gccatcgctg acttgcttct cgttgtaccg accattgtag cacgtgtgta gcccaggaca    300
taaagggcat gatgatttga cgtcatcccc accttcctcc gatttgtcat cggcagtctc    360
tttagagtgc ccaacttaat gatggcaact aaagacaagg gttgcgctcg ttgcgggact    420
taacccaaca tctcacgaca cgagctgacg acaaccatgc accacctgtg tccgctgtac    480
cccgaaggat aaagatctat ctctaaaccg gtcagcggca tgtcaagccc tggtaaggtt    540
cttcgcgttg cttcgaatta aaccacatgc tccgctgctt gtgcgggtcc ccgtcaattc    600
ctttgagttt catacttgcg tacgtactcc ccaggcggag tgcttaatgc gttagctgcg    660
gcaccgaggt ttgacccccca acacctagca ctcatcgttt acggcgtgga ctaccagggt    720
atctaatcct gtttgctccc cacgctttcg ttcctcagcg tcagtataag tccagaaagt    780
cgccttcgcc actggtattc ctcctaatat ctacgcattt caccgctaca ctaggaattc    840
cactttcctc tccttaactc aagtctgaca gtttcaaatg cttacgtagg ttgagcctac    900 gccttcaca tctgacttat cagaccgcct gcgaaccctt tacgcccaat aattccggac    960
aacgctcgcc cctacgtat taccgcggct gctggcacgt agttagccgg ggcttcctcc   1020
ttgggtaccg tcattatctt ccccaaggac agaactttac aacccgaagg ccttcatcat   1080
```

```
tcacgcggcg tcgctgcatc agagtttcct ccattgtgca atattcccca ctgctgcctc    1140
ccgtaggagt ctggaccgtg tctcagttcc agtgtggccg ttcaccctct caggccggct    1200
acctatcgaa gccttggtga gccgttacct caccaactag ctaataggac gcgagaccat    1260 cttttcaccgc ttattcgctt tgactgatct accatgcgt  aattcagttt cataaggtat    1320
taatcccagt ttcccgaggc tatccctttg tgaaaggcag gtttctcacg cgttactcac    1380
ccgtccgccg ctaagatgac tcttcgatcc atccgaaaay ttctctcmga gtcacttcgc    1440
ggcacgccgc cagcgttcgt cctgagccak aatcaaactc t                        1481
```

<210> SEQ ID NO 46
<211> LENGTH: 1486
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 46

```
tggctcagat tgaacgctgg cggcaggcct aacacatgca agtcgagcgg atgagtggag      60
cttgctccat gattcagcgg cggacgggtg agtaatgcct aggaatctgc ctggtagtgg    120
gggacaacgt ttcgaaagga acgctaatac cgcatacgtc ctacgggaga agtggggga    180 tcttcggacc tcacgctatc agatgagcct aggtcggatt agctagttgg tgaggtaaag    240
gctcaccaag gcgacgatcc gtaactggtc tgagaggatg atcagtcaca ctggaactga    300
gacacggtcc agactcctac gggaggcagc agtggggaat attggacaat gggcgaaagc    360
ctgatccagc catgccgcgt gtgtgaagaa ggtcttcgga ttgtaaagca ctttaagttg    420
ggaggaaggg cagtaagtta ataccttgct gttttgacgt taccgacaga ataagcaccg    480
gctaacttcg tgccagcagc cgcggtaata cgaaggtgc aagcgttaat cggaattact    540
gggcgtaaag cgcgcgtagg tggttcgtta agttggatgt gaaagccccg ggctcaacct    600
gggaactgca tccaaaactg gcgagctaga gtatggcaga tggtggtgga atttcctgtg    660
tagcggtgaa atgcgtacat ataggaagga acaccagtgg cgaaggcgac cacctgggct    720
aatactgaca ctgaggtgcg aaagcgtggg gagcaaacag gattagatac cctggtagtc    780
cacgccctaa acgatgtcga ctagtcgttc ggagcagcaa tgcactgagt gacgcagcta    840
acgcgtgaag tcgaccgcct ggggagtacg gccgcaaggt taaaactcaa aggaattgac    900
ggggacccgc acaagcggtg gatgatgtgg attaattcga tgcaacgcga aaaaccttac    960
ctacccttga catgccagga accttgccga gaggcgaggg tgccttcggg agcctggaca   1020
caggtgctgc atggctgtcg tcagctcgtg tcgtgagatg ttgggttaag tcccgcaacg   1080
agcgcaaccc ttgtcactag ttgccatcat ttggttgggc actctagtga gactgccggt   1140
gacaaaccgg aggaaggtgg ggatgacgtc aagtcctcat ggcccttatg ggtagggctt   1200
cacacgtcat acaatggtcg gtacagaggg ttgccaagcc gcgaggtgga gccaatccct   1260
taaagccgat cgtagtccgg atcgtagtct gcaactcgac tacgtgaagt cggaatcgct   1320
agtaatcgca gatcagcatg ctgcggtgaa tacgttcccg ggtcttgtac acaccgcccg   1380
tcacaccatg ggagtgggtt tcaccagaag taggtagctt aaccttcggg agggcgctta   1440
ccacggtgag attcatgact ggggtgaagt cgtaacaagg taaccg                   1486
```

<210> SEQ ID NO 47
<211> LENGTH: 1442
<212> TYPE: DNA

<213> ORGANISM: unknown
<220> FEATURE:
<223> OTHER INFORMATION: Unknown clone from enriched environmental
      sample that by rDNA sequence analysis has highest identity to
      Ochrobactrum sp. mp-5

<400> SEQUENCE: 47

| | | | | |
|---|---|---|---|---|
| tggctcagaa | cgaacgctgg | cggcaggctt | aacacatgca | agtcgagcgc cccgcaaggg | 60 |
| gagcggcaga | cgggtgagta | acgcgtggga | acgtaccttt | tgctacggaa taactcaggg | 120 |
| aaacttgtgc | taataccgta | tgtgcccttc | ggggaaaga | tttatcggca aaggatcggc | 180 |
| ccgcgttgga | ttagctagtt | ggtgaggtaa | aggctcacca | aggcgacgat ccatagctgg | 240 |
| tctgagagga | tgatcagcca | cactgggact | gagacacggc | ccagactcct acgggaggca | 300 |
| gcagtgggga | atattggaca | atgggcgcaa | gcctgatcca | gccatgccgc gtgagtgatg | 360 |
| aaggccctag | ggttgtaaag | ctctttcacc | ggtgaagata | atgacggtaa ccggagaaga | 420 |
| agccccggct | aacttcgtgc | cagcagccgc | ggtratacga | aggggctag cgttgttcgg | 480 |
| atttactggg | cgtaaagcgc | acgtaggcgg | acttttaagt | caggggtgaa atcccggggc | 540 |
| tcaayccegg | aactgccttt | gatactggaa | gtcttgagta | tggtagaggt gagtggaatt | 600 |
| ccgagtgtag | aggtgaaatt | cgtagatatt | cggaggaaca | ccagtggcga aggcggctca | 660 |
| ctggaccatt | actgacgctg | aggtgcgaaa | gcgtggggag | caaacaggat tagatacect | 720 |
| ggtagtccac | gccgtaaacg | atgaatgtta | gccgttgggg | agtttactct cggtggcgc | 780 |
| agctaacgca | ttaaacattc | cgcctgggga | gtacggtcgc | aagattaaaa ctcaaaggaa | 840 |
| ttgacggggg | cccgcacaag | cggtggagca | tgtggtttaa | ttygaagcaa cgcgcagaac | 900 |
| cttaccagcc | cttgacatac | cggtcgcgga | cacagagatg | tgtctttcag ttcggctgga | 960 |
| ccggatacag | gtgctgcatg | gctgtcgtca | gctcgtgtcg | tgagatgttg ggttaagtcc | 1020 |
| cgcaacgagc | gcaaccctcg | cccttagttg | ccagcattta | gttgggcact ctaagggac | 1080 |
| tgccggtgat | aagccgagag | gaaggtgggg | atgacgtcaa | gtcctcatgg cccttacggg | 1140 |
| ctgggctaca | cacgtgctac | aatggtggtg | acagtgggca | gcgagcacgc gagtgtgagc | 1200 |
| taatctccaa | aagccatctc | agttcggatt | gcactctgca | actcgagtgc atgaagttgg | 1260 |
| aatcgctagt | aatcgcggat | cagcatgccg | cggtgaatac | gttcccgggc cttgtacaca | 1320 |
| ccgcccgtca | caccatggga | gttggtttta | cccgaaggcg | ctgtgctaac cgcaaggagg | 1380 |
| caggcgacca | cggtagggtc | agcgactggg | gtgaagtcgt | aacaaggtaa ccgaagggcg | 1440 |
| at | | | | | 1442 |

<210> SEQ ID NO 48
<211> LENGTH: 1478
<212> TYPE: DNA
<213> ORGANISM: unknown
<220> FEATURE:
<223> OTHER INFORMATION: Unknown clone from enriched environmental
      sample that by rDNA sequence analysis has highest identity to
      Anaeurovorax sp/EH8A

<400> SEQUENCE: 48

| | | | | |
|---|---|---|---|---|
| tggctcagga | tgaacgctgg | cggcgtgcct | aacacatgca | agtcgagcgg tatatagtgg | 60 |
| aatgaaactt | cggtcgagtg | aagctataga | gagcggcgca | cgggtgagta acgcgtaggc | 120 |
| aacctgcccc | atacagaggg | atagcctcgg | gaaaccggga | ttaaaacctc ataacgcgag | 180 |
| gagttcacat | ggactgctcg | ccaaagattc | atcggtatgg | gatgggcctg cgtctgatta | 240 |
| gctagttggt | gaggtaacgg | ctcaccaagg | cgacgatcag | tatccgacct gagagggtaa | 300 |

```
tcggccacat tggaactgag acacagtcca aactcctaca ggaggcagca gtggggaata      360
ttgcacaatg ggcgaaagcc tgatgcaaca acgccgcgtg agcgatgaac gcctttgggt      420
cgtaaagctc tgtccttggg gaagaaacaa atgacggtac ccttggaaga agccccggct      480
aactacgtgc cagcagccgc ggtaatacgt aggggggcgag cgttatccgg aattattggg      540
cgtaaagagt gcgtacgtgg ctatgtaagc gcgaggtgaa aggcaatagc ttaactattg      600
taagccttgc gaactgtgtg gcttgggtgc aggacaggaa agtggaattc ctattgtagc      660
ggtgaaatgc gtagatatta ggaggaacac cactggcgaa ggcgactttc tggactgtaa      720
ctgacactga ggcacgaaag cgtggggagc aaacaggatt agatacctg gtagtccacg       780 ccgtaaacga tgagcactag gtgtaggggt cgcaagactt cggtgccgca gttaacgcat      840
taagtgctcc gcctggggag tacgcacgca agtgtgaaac tcaaaggaat tgacggggac      900
ccgcacaagc agcggagcat gtggtttaat tcgaagcaac gcgaagaacc ttatcagggc      960
ttgacatccg tatgacagtc cgttaaccgg gacgttcttc ggacagagga gacaggtggt     1020
gcatggttgt cgtcagctcg tgtcgtgaga tgttgggtta agtcccgcaa cgagcgcaac     1080
ccttgtcttt agttgccatc atttggttgg gcactctagt gagactgccg gtgacaaacc     1140
ggaggaaggt ggggatgacg tcaagtcctc atggccctta tgggtagggc ttcacacgtc     1200
atacaatggt cggtacagag ggttgccaag ccgcgaggtg gagccaatcc cttaaagccg     1260
atcgtagtcc ggatcgtagt ctgcaactcg actacgtgaa gtcggaatcg ctagtaatcg     1320
cagatcagca tgctgcggtg aatacgttcc cgggtcttgt acacaccgcc cgtcacacca     1380
tgggagtggg tttcaccaga agtaggtagc ttaaccttcg ggagggcgct taccacggtg     1440
agattcatga ctggggtgaa gtcgtaacaa ggtaaccg                             1478

<210> SEQ ID NO 49
<211> LENGTH: 883
<212> TYPE: DNA
<213> ORGANISM: unknown
<220> FEATURE:
<223> OTHER INFORMATION: Unknown clone from enriched environmental
      sample that by rDNA sequence analysis has highest identity to
      Anaerovorax sp. EH8A

<400> SEQUENCE: 49
tggctcagga tgaacgctgg cggcgtgcct aacacatgca agtcgagcgg tatatagtgg       60
aacgaaactt cggtcgagtg aagccataga gagcggcgga cgggtgagta acgcgtaggc      120
aacctgcccc atacagaggg atagcctcgg gaaaccggga ttaaaacctc ataacgcgag      180
gagttcacat ggacttctcg ccaaagattc atcggtatgg gatgggcctg cgtctgatta      240
gctagttggt gaggtaacgg ctcaccaagg cgacgatcag tagccgacct gagagggtaa      300
tcggccacat tggaactgag acacggtcca aactcctacg ggaggcagca gtggggaata      360
ttgcacaatg ggcgaaagcc tgatgcagca acgccgcgtg agcgatgaag gcctttgggt      420
cgtaaagctc tgtccttggg gaagaaacaa atgacggtac ccttggagga agccccggct      480
aactacgtgc cagcagccgc ggtaatacgt aggggggcgag cgttatccgg aattattggg      540
cgtaaagagt gcgtaggtgg ccatgtaagc gcgggtgaa aggcaatagc ttaactattg       600
taagccttgc gaactgtgtg gcttgagtgc aggagaggaa agtggaattc ctagtgtagc      660
ggtgaaatgc gtagatatta ggaggaacac cagtggcgaa ggcgactttc tggactgtaa      720
ctgacactga ggcacgaaag cgtggggagc aaacaggatt agatacctg gtagtccacg       780 ccgtaaacga tgagcactag gtgtcggggt cgcaagactt cggtgccgca gttaacgcat      840
```

```
taagtgctcc gcctggggag tacgcacgca agtgtgaaac tca         883
```

<210> SEQ ID NO 50
<211> LENGTH: 521
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 50

```
acatgccact gaccgcatca gagatggtgc tttaccttcg ggtacagtgg acacaggtgg    60
tgcatggttg tcgtcagctc gtgtcgtgag atgttgggtt aagtcccgca acgagcgcaa   120
cccctgtttc tagttgccag cattaagttg ggcactctag agagactgcc gatgacaaat   180
cggaggaagg tggggatgac gtcaaatcat catgcccttt atgccctggg ctacacacgt   240
gctacaatgg tcggtacaac gaggagcaaa ccagcgatgg caagcaaatc tctaaaagcc   300
gatcccagtt cggattgcag gctgcaactc gcctgcatga agtcggagtt gctagtaatc   360
gcggatcaga atgtcgcggt gaatgcgttc ccgggtcttg tacacaccgc ccgtcacacc   420
atgggagttg tcaatacccg aagccagtga gctaaccagt aatggaggca gctgtcgaag   480
gtaggggcga tgactggggt gaagtcgtaa caaggtaacc g                       521
```

<210> SEQ ID NO 51
<211> LENGTH: 888
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 51

```
tacgtaagca tttgaaactg tcagacttga gttaaggaga ggaaagtgga attcctagtg    60
tagcggtgaa atgcgtagat attaggagga ataccagtgg cgaaggcgac tttctggact   120
tatactgacg ctgaggaacg aaagcgtggg gagcaaacag gattagatac cctggtagtc   180
cacgccgtaa acgatgagtg ctaggtgttg ggggtcaaac ctcggtgccg cagctaacgc   240
attaagcact ccgcctgggg agtacgtacg caagtatgaa actcaaagga attgacgggg   300
acccgcacaa gcagcggagc atgtggttta attcgaagca acgcgaagaa ccttaccagg   360
gcttgacatg ccgctgaccg gtgcagagat gcatctttat ccttcggggt acagcggaca   420
caggtggtgc atggttgtcg tcagctcgtg tcgtgagatg ttgggttaag tcccgcaacg   480
agcgcaaccc ttgtctttag ttgccatcat taagttgggc actctaaaga gactgccgat   540
gacaaatcgg aggaaggtgg ggatgacgtc aaatcatcat gccctttatg tcctgggcta   600
cacacgtgct acaatggtcg gtacaacgag aagcaagtca gcgatggcaa gcaaatctct   660
aaaagccgat cccagttcgg attgcaggct gcaactcgcc tgcatgaagt cggagttgct   720
agtaatcgcg gatcagaatg ccgcggtgaa tgcgttcccg ggtcttgtac acaccgcccg   780
tcacaccatg ggagttgtca atacccgaag ccagtgagct aaccataaaa ggaggcagct   840
gtcgaaggta ggggcaatga ctggggtgaa gtcgtaacaa ggtaaccg                888
```

<210> SEQ ID NO 52
<211> LENGTH: 888
<212> TYPE: DNA
<213> ORGANISM: unknown
<220> FEATURE:

<223> OTHER INFORMATION: Unknown clone from enriched environmental
      sample that by rDNA sequence analysis has highest identity to
      Finegoldia magna

<400> SEQUENCE: 52

```
tacgtaagca tttgaaactg tcagacttga gttaaggaga ggaaagtgga attcctagtg      60
tagcggtgaa atgcgtagat attaggagga ataccagtgg cgaaggcgac tttctggact     120
tatactgacg cggaggaacg aaagcgtggg gagcaaacag gattagatac cctggtagtc     180
cacgccgtaa acgatgagtg ctaggtgttg ggggtcaaac ctcggtgccg cagctaacgc     240
attaagcact ccgcctgggg agtacgtacg caagtatgaa actcaaagga attgacgggg     300
acccgcacaa gcagcggagc atgtggttta attcgaagca acgcgaagaa ccttaccagg     360
gcttgacatg ccgctgaccg gtttagagat agatctttac ccttcggggt acagcggaca     420
caggtggtgc atggttgtcg tcagctcgtg tcgtgagatg ttgggttaag tcccgcaacg     480
agcgcaaccc ttgtctttag ttgccatcat taagttgggc actctaaaga gactgccgat     540
gacaaatcgg aggaaggtgg ggatgacgtc aaatcatcat gccctttatg tcctgggcta     600
cacacgtgct acaatggtcg gtacaacgag aagcaagtca gcgatggcaa gcaaatctct     660
aaaagccgat cccagttcgg attgcaggct gcaactcgcc tgcatggagt cggagttgct     720
agtaatcgcg gatcagaatg ccgcggtgaa tgcgttcccg gtcttgtac acaccgcccg      780
tcacaccatg ggagttgtca atacccgaag ccagtgagct aaccataaaa gggggcagct     840
gtcgaaggta ggggcaatga ctggggtgaa gtcgtaacaa ggtaaccg                  888
```

<210> SEQ ID NO 53
<211> LENGTH: 1502
<212> TYPE: DNA
<213> ORGANISM: unknown
<220> FEATURE:
<223> OTHER INFORMATION: Unknown clone from enriched environmental
      sample that by rDNA sequence analysis has highest identity to
      Flexistipes sp. vp180

<400> SEQUENCE: 53

```
tggctcagaa cgaacgctgg cggcgtgctt aacacatgca agtcaaggag aaagtctctt      60
cggaggcgag taaactggcg cacgggtgag taacgcgtga ggaacctgcc catatgtctg     120
ggataacctg ctgaaaagcg ggctaatact ggatatattg tttaccgcat ggtgaacaag     180
gaaagttggt gcaagctaac gcatatggat ggtctcgcgt ctgattagct agttggtggg     240
gtaaaggctc accaaggcga cgatcagtag ccggtctgag agggtggccg gccacactgg     300
gactgagaca cggcccagac tcctacggga ggcagcagtg gggaattttg cacaatgggg     360
gcaaccctga tgcagcgacg ccgcgtgaac gaggaaggcc ttcgggtcgt aaagttcttt     420
cgacggggaa gaaatgttat acgagtaact gcgtataatt tgacggtacc tgtagaagca     480
gccccggcta actccgtgcc agcagccgcg gtaatacgga gggggcgagc gttgttcgga     540
gttactgggc gtaaagcgca cgtaggcggt gcggtaagtc agggttaaa ggtcacagct     600
caactgtgat aaggcctttg atactatcgt gctagagtgt cagagagggt agcggaattc     660
ccggtgtagc ggtgaaatgc gtatatatcg gaggaacac cagtggcgaa gggcggctac     720
ctggctgata actgacgctg aggtgcgaga gcgtggggag caaacaggat tagataccct     780
ggtagtccac gctgtaaacg atggacgtta ggtgttgggg aaccgacccc cctcagtgcc     840
gaagctaacg cgttaaacgt cccgcctggg gagtacggcc gcaaggttga aactcaaagg     900
aattgacggg ggcccgcaca agcggtggag cacgtggttt aattcgatgc taaccgaaga     960
```

```
accttacctg ggtttgacat ccctcgaatc ctgtagagat atgggagtgc ctggcttgcc    1020
aggagcgagg agacaggtgc tgcatggctg tcgtcagctc gtgccgtgag gtgttgggtt    1080
aagtcccgca acgagcgcaa cccctatttt tagttgccat cacgttaagg tgggcactct    1140
aaagagaccg ccggggataa cccggaggaa ggtggggatg acgtcaagtc atcatggccc    1200
ttatgtccag ggctacacac gtgctacaat ggtgcataca gagggcagcg agacagcgat    1260
gttaagcgaa tcccttaaag tgtacctcag ttcggattgc agtctgcaac tcgactgtat    1320
gaagccggaa tcgctagtaa tcgcaggtca gcaaaactgc ggtgaatacg ttcccgggcc    1380
ttgtacacac cgcccgtcac accacgggag tcggttgtac ctgaagccgg tgcccaacc    1440 gcaagggggg agccgtctat ggtatggctg gtaactgggg tgaagtcgta acaaggtaac    1500
cg                                                                  1502

<210> SEQ ID NO 54
<211> LENGTH: 1499
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus sp. EH11

<400> SEQUENCE: 54
agagtttgat tatggctcag attgaacgct ggcggcatgc tttacacatg caagtcgaac    60
ggcagcgggg gcttcggcct gccggcgagt ggcgaacggg tgagtaatgc atcggaacgt    120
gcccatgtcg tgggggataa cgtatcgaaa ggtacgctaa taccgcatac gtcctgaggg    180
agaaagcggg ggatcttcgg acctcgcgcg attggagcgg ccgatgtcgg attagctagt    240
aggtgaggta aaggctcacc taggcgacga tccgtagcgg gtctgagagg atgatccgcc    300
acactgggac tgagacacgg cccagactcc tacgggaggc agcagtgggg aattttggac    360
aatgggcgca agcctgatcc agccatgccg cgtgagtgaa gaaggccttc gggttgtaaa    420
gctctttcgg ccgggaagaa atcgtggtct ctaacatagg ccatggatga cggtaccgga    480
ctaagaagca ccggctaact acgtgccagc agccgcggta atacgtaggg tgcgagcgtt    540
aatcggaatt actgggcgta aagcgtgcgc aggcggtttt gtaagacaga tgtgaaatcc    600
ccgggctcaa cctgggaact gcgtttgtga ctgcaaggct agagtacggc agaggggggt    660
ggaattcctg gtgtagcagt gaaatgcgta gagatcagga ggaacaccga tggcgaaggc    720
agccccctgg gcctgtactg acgctcatgc acgaaagcgt ggggagcaaa caggattaga    780
taccctggta gtccacgccg taaacgatga gtgctaggtg ttgggggtca aacctcggtg    840
ccgcagctaa cgcattaagc actccgcctg gggagtacgg acgcaagtat gaaactcaaa    900
ggaattgacg gggacccgca caagcagcgg agcatgtggt ttaattcgaa gcaacgcgaa    960
gaaccttacc agggcttgac atgccgctga ccggtttaga gatagacctt tatccttcgg    1020
ggtacagcgg acacaggtgg tgcatggttg tcgtcagctc gtgtcgtgag atgttgggtt    1080
aagtcccgca acgagcgcaa cccttgtcac tagttgccag catttagttg ggcactctgg    1140
tgagactgcc ggtgacaaac cggaggaagg tggggatgac gtcaagtcct catggccctt    1200
atgggtaggg cttcacacgt catacaatgg tcggtacaga gggttgccaa gccgcgaggt    1260
ggagccaatc ccttaaagcc gaccgtagtc cggatcgtag tctgcaactc gactacgtga    1320
agtcggaatc gctagtaatc gcagatcagc atgctgcggt gaatacgttc ccgggtcttg    1380
tacacaccgc ccgtcacacc atgggagtgg gtttcaccag aagtaggtag cttaaccttc    1440
```
gggagggcgc ttaccacggt gagattcatg actggggtga agtcgtaaca aggtaaccg    1499

<210> SEQ ID NO 55
<211> LENGTH: 1475
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium chartatabidium

<400> SEQUENCE: 55
tggctcagga cgaacgctgg cggcgtgcct aacacatgca agtcgagcgg agaatgcaga 60
aatgtttaca tggaagtatt cttagcggcg gacgggtgag taacacgtgg gtaacctgcc 120
tcaaagtggg ggatagcctt ccgaaaggaa gattaatacc gcataagcct acagtgccgc 180
atggcacagc aggaaaagga gcaatccgct ttgagatgga cccgcggcgc attagctagt 240
tggtgaggta acggctcacc aaggcgacga tgcgtagccg acctgagagg gtgatcggcc 300
acattggaac tgagacacgg tccagactcc tacgggaggc agcagtgggg aatattgcac 360
aatgggcgaa agcctgatgc agcaacgccg cgtgagtgat gaaggccttc gggtcgtaaa 420
gctctttgat cagggatgat aatgacagta cctgaaaaac aagccacggc taactacgtg 480
ccagcagccg cggtaatacg taggtggcga gcgttgtccg gaattactgg gcgtaaagga 540
tgcgtaggtg gatacttaag tgggatgtga aatccccggg ctcaacccgg gaactgcatt 600
ccaaactggg tatctagagt gcaggagagg aaagcggaat tcctagtgta gcggtgaaat 660
gcgtagagat caggaggaac accgatggcg aaggcagccc cctgggcctg tactgacgct 720
catgcacgaa agcgtgggga gcaaacaggg atagataccc tggtagtcca cgccctaaac 780
gatgtcgaat aagtcgttcc gaccagcaat gcactgagtg acgcagctaa cgcgtgaagt 840
cgaccgcctg gggagtacgg ccgcaaggtt aaaactcaaa ggaattgacg gggacccgca 900
caagcggtgg atgatgtgga ttaattcgat gcaacgcgaa aaccttacc tacccttgac 960 atgccaggaa ccttgccgag aggcgagggt gccttcggga gcctggacac aggtgctgca 1020
tggctgtcgt cagctcgtgt cgtgagatgt tgggttaagt cccgcaacga gcgcaaccct 1080
tgtcactagt tgccatcatt tggttgggca ctctagtgag actgccggtg acaaaccgga 1140
ggaaggtggg gatgacgtca agtcctcatg gcccttatgg gtagggcttc acacgtcata 1200
caatggtcgg tacagagggt tgccaagccg cgaggtggag ccaatccctt aaagccgatc 1260
gtagtccgga tcgtagtctg caactcgact acgtgaagtc ggaatcgcta gtaatcgcag 1320
atcagcatgc tgcggtgaat acgttcccgg gtcttgtaca caccgcccgt cacaccatgg 1380
gagtgggctt caccagaagt aggtagctta accttcggga gggcgcttac cacggtgaga 1440
ttcatgactg gggtgaagtc gtaacaaggt aaccg 1475

<210> SEQ ID NO 56
<211> LENGTH: 1492
<212> TYPE: DNA
<213> ORGANISM: unknown
<220> FEATURE:
<223> OTHER INFORMATION: Unknown clone from enriched environmental sample that by rDNA sequence analysis has highest identity to Deferribacter desulfuricans

<400> SEQUENCE: 56
tggctcagaa cgaacgctgg cggcgtgctt aacacatgca agtcaaggag aaagtctctt 60
cggaggcgag taaactggcg cacgggtgag taacgcgtga ggaacctgcc catatgtctg 120

-continued

```
ggataacctg ctgaaaagcg ggctaatact ggatatattg tttaccgcat ggtgaacaag      180
gaaagttggt gcaagctaac gcatatggat ggtctcgcgt ctgattagct agttggtggg      240
gtaaaggctc accaaggcaa cgatcagtag ccggtctgag agggtggccg gccacactgg      300
gactgagaca cggcccagac tcctacggga ggcagcagtg gggaattttg cacaatgggg      360
gcaaccctga tgcagcgacg ccgcgtgaac gaggaaggcc ttcgggtcgt aaagttcttt      420 cgacgggaa gaaatgttat acgagtaact gcgtataatt tgacggtacc cgtagaagca      480
gccccggcta actccgtgcc agcagccgcg gtaatacgga gggggcgagc gttgttcgga      540
gttactgggc gtaaagcgca cgtacgcggt gcggtaagtc aggggttaaa ggtcacagct      600
caactgtgat aaggcctttg atactatcgt gctagagtgt cagagagggt agcggaattc      660
ccggtgtagc ggtgaaatgc gtagatatcg gaggaacac cagtagcgaa ggcggctacc       720
tggctgataa ctgacgctga ggtgcgagag cgtgggagc aaacaggatt agatacctg        780 gtagtccacg ccctaaacga tgtcgactag tcgttcggag cagcaatgca ctgagtgacg      840
cagctaacgc gtgaagtcga ccgcctgggg agtacggccg caaggttaaa actcaaagga     900
attgacgggg acccgcacaa gcggtggatg atgtggatta attcgatgca acgcgaaaaa      960
ccttacctac ccttgacatg ccaggaacct tgccgagagg cgagggtgcc ttcgggagcc     1020
tggacacagg tgctgcatgg ctgtcgtcag ctcgtgtcgt gagatgttgg gttaagtccc     1080
gcaacgagcg caacccttgt cactagttgc catcatttgg ttgggcactc tagtgagact     1140
gccggtgaca aaccggagga aggtggggat gacgtcaagt cctcatggcc cttatgggta     1200
gggcttcaca cgtcatacaa tggtcggtac agagggttgc caagccgcga ggtggagcca     1260
atcccttaaa gccgatcgta gtccggatcg tagtctgcaa ctcgactacg tgaagtcgga     1320
atcgctagta atcgcagatc agcatgctgc ggtgaatacg ttcccgggtc ttgtacacac     1380
cgcccgtcac accatgggag tgggtttcac cagaagtagg tagcttaacc ttcgggaggg     1440
cgcttaccac ggtgagattc atgactgggg tgaagtcgta acaaggtaac cg             1492
```

<210> SEQ ID NO 57
<211> LENGTH: 1519
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 57

```
tggctcagaa cgaacgctgg cggcgtgctt aacacatgca agtcaagggg aaagtctctt       60
cggaggcgag taaactggcg cacgggtgag taacgcgtga ggaacctgcc catatgtctg      120
ggataacctg ctgaaaagcg ggctaatact ggatatattg tttaccgcat ggtgaacaag      180
gaaagttggt gcaagctaac gcatatggat ggtctcgcgt ctgattagct agttggtggg      240
gtaaaggctc accaaggcaa cgatccgtag cgggtctgag aggatggtcc gccacactgg      300
gactgagaca cggcccagac tcctacggga ggcagcagtg gggaattttg acaatgggc       360 gcaagcctga tccagccatg ccgcgtgagt gaagaaggcc ttcgggttgt aaagctcttt      420
cggccgggaa gaaatcgtgg tctctaacat aggccatgga tgacggtacc ggactaagaa      480
gcaccggcta actccgtgcc agcagccgcg gtaatacgta gggtgcgagc gttaatcgga      540
attactgggc gtaaagcgtg cgcaggcggt tttgtaagac agatgtgaaa tccccgggct      600
caacctggga actgcgtttg tgactgcaag gctagagtac ggcagagggg ggtggaattc      660
```

-continued

```
ctggtgtagc agtgaaatgc gtagagatca ggaggaacac cgatggcgaa ggcagccccc      720
tgggcctgta ctgacgctca tgcacgaaag cgtggggagc aaacaggatt agataccctg      780
gtagtccacg ccctaaacga tgtcgactag tcgttcggag cagcaatgca ctgagtgacg      840
cagctaacgc gtgaagtcga ccgcctgggg agtacggccg caaggttaaa actcaaagga      900
attgacgggg acccgcacaa gcggtggatg atgtggatta attcgatgca acgcgaaaaa      960
ccttacctac ccttgacatg ccaggaacct tgccgagagg cgaggtgcc ttcgggagcc      1020 tggacacagg tgctgcatgg ctgtcgtcag ctcgtgtcgt gagatgttgg gttaagtccc     1080
gcaacgagcg caaccettgt cactagttgc catcatttgg ttgggcactc tagtgagact     1140
gccggtgaca aaccggagga aggtggggat gacgtcaagt cctcatggcc cttatgggta     1200
gggcttcaca cgtcatacaa tggtcggtac agagggttgc caagccgcga ggtggagcca     1260
atcccttaaa gccgatcgta gtccggatcg tagtctgcaa ctcgactacg tgaagtcgga     1320
atcgctagta atcgcagatc agcatgctgc ggtaaatacg ttcccgggtc ttgtacacac     1380
cgcccgtcac accatgggag tgggtttcac cagaagtagg tagcttaacc ttcgggaggg     1440
cgcttaccac ggtgagattc atgactgggg tgaagtcgta acaaggtaac cgaagggcga     1500
atcaatcgcc tatgactgg                                                   1519
```

<210> SEQ ID NO 58
<211> LENGTH: 373
<212> TYPE: DNA
<213> ORGANISM: unknown
<220> FEATURE:
<223> OTHER INFORMATION: Unknown clone from enriched environmental
    sample that by rDNA sequence analysis has highest identity to
    Flexistipes sp. vp180

<400> SEQUENCE: 58

```
tggctcagaa cgaacgctgg cggcgtgctt aacacatgca agtcaaggag aaaatctctt       60
cgggggcgag taaactggcg cacgggtgag taacgcgtga ggaacctgcc catatgtctg      120
ggataacctg ctgaaaagcg ggctaatact ggatatattg tttaccgcat ggtggacaag     180
gaaagttggt gtaagctaac gcatatggat ggtctcgcgt ctgattagct agttggtggg     240
gtaaaggctc accaaggcga cgatcagtag ccggtctgag agggtggccg gccacactgg     300
gactgagaca cggcccatac tcctacggga ggcagcagtg gggaattttg cacaatgggg     360
gcaaccctga tgc                                                         373
```

<210> SEQ ID NO 59
<211> LENGTH: 1431
<212> TYPE: DNA
<213> ORGANISM: unknown
<220> FEATURE:
<223> OTHER INFORMATION: Unknown clone from enriched environmental
    sample that by rDNA sequence analysis has highest identity to
    Ochrobactrum lupini

<400> SEQUENCE: 59

```
tggctcagaa cgaacgctgg cggcaggctt aacacatgca agtcgagcgc cccgcaagga       60
gagcggcaga cgggtgagta acgcgtggga acgtaccttt tgctacggaa taactcaggg     120
aaacttgtgc taataccgta tgtgcccttc ggggggaaaga tttatcggca aaggatcggc     180
ccgcgttgga ttagctagtt ggtgaggtaa aggctcacca aggcgacgat ccatagctgg     240
tctgagagga tgatcagcca cactgggact gagacacggc ccagactcct acggaggca     300 gcagtgggga atattggaca atgggcgcaa gcctgatcca gccatgccgc gtgagtgatg     360
```

-continued

| | |
|---|---|
| aaggccctag ggttgtaaag ctctttcacc ggtgaagata atgacggtaa ccggagaaga | 420 |
| agccccggct aacttcgtgc cagcagccgc ggtaatacga agggggctag cgttgttcgg | 480 |
| atttactggg cgtaaagcgc acgtaggcgg actttttaagt cagggtgaa atcccggggc | 540 |
| tcaaccccgg aactgccttt gatactggaa gtcttgagta tggtagaggt gagtggaatt | 600 |
| ccgagtgtag aggtgaaatt cgtagatatt cggaggaaca ccagtggcga aggcggctca | 660 |
| ctggaccatt actgacgctg aggtgcgaaa gcgtggggag caaacaggat tagataccct | 720 |
| ggtagtccac gccgtaaacg atgaatgtta gccgttgggg agtttactct cggtggcgc | 780 |
| agctaacgca ttaaacattc cgcctgggga gtacggtcgc aagattaaaa ctcaaaggaa | 840 |
| ttgacgggga cccgcacaag cggtggatga tgtggattaa ttcgatgcaa cgcgaaaaac | 900 |
| cttacctacc cttgacatgc caggaacctt gccgagaggc gagggtgcct tcgggagcct | 960 |
| ggacacaggt gctgcatggc tgtcgtcagc tcgtgtcgtg agatgttggg ttaagtcccg | 1020 |
| caacgagcgc aacccttgcc actagttgcc atcatttggt tgggcactct agtgagactg | 1080 |
| ccggtgacaa accggaggaa ggtggggatg acgtcaagtc ctcatggccc ttatgggtag | 1140 |
| ggcttcacac gtcatacaat ggtcggtaca gagggttgcc aagccgcgag gtggagccaa | 1200 |
| tcccttaaag ccgatcgtag tccggatcgt agtctgcaac tcgactacgt gaagtcggaa | 1260 |
| tcgctagtaa tcgcagatca gcatgctgcg gtgaatrcgt tcccgggtct tgtacacacc | 1320 |
| gcccgtcaca ccatgggagt gggtttcacc agaagtaggt agcttaacct tcgggagggc | 1380 |
| acttaccacg gtgagattca tgactggggt gaagtcgtaa caaggtaacc g | 1431 |

<210> SEQ ID NO 60
<211> LENGTH: 1454
<212> TYPE: DNA
<213> ORGANISM: unknown
<220> FEATURE:
<223> OTHER INFORMATION: Unknown clone from enriched environmental sample that by rDNA sequence analysis has highest identity to Pseudomonas pseudoalcligenes

<400> SEQUENCE: 60

| | |
|---|---|
| tggctcagat tgaacgctgg cggcaggcct aacacatgca agtcgagcgg atgagtggag | 60 |
| cttgctccat gattcagcgg cggacgggtg agtaatgcct aggaatctgc ctggtagtgg | 120 |
| gggacaacgt ttcgaaagga acgctaatac cgcatacgtc ctacgggaga aagtggggga | 180 |
| tcttcggacc tcacgctatc agatgagcct aggtcggatt agctagttgg cgaggtaaag | 240 |
| gctcaccaag gcgacgatcc gtaactggtc tgagaggatg atcagtcaca ctggaactga | 300 |
| gacacggtcc agactcctac gggaggcagc agtggggaat attggacaat gggcgaaagc | 360 |
| ctgatccagc catgccgcgt gtgtgaagaa ggtcttcgga ttgtaaagca ctttaagttg | 420 |
| ggaggaaggg cagtaagtta ataccttgct gttttgacgt taccgacaga ataagcaccg | 480 |
| gctaacttcg tgccagcagc cgcggtaata cgaagggtgc aagcgttaat cggaattact | 540 |
| gggcgtaaag cgcgcgtagg tggttcgtta agttggatgt gaaagccccg ggctcaacct | 600 |
| gggaactgca tccaaaactg gcgagctaag ttatggcaga gggggtgga aatttcctgt | 660 |
| gtagcggtga aatgggtaga tataggaagg aacaccagtg gcgaaggcga ccacctgggc | 720 |
| taatactgac actgaggtgc gaaagcgtgg ggagcaaaca ggattagata ccctggtagt | 780 |
| ccacgccgta aacgatgtcg actagccgtt gggatccttg agatcttagt ggcgcagcta | 840 |
| acgcattaag tcgaccgcct ggggagtacg gccgcaaggt taaaactcaa atgaattgac | 900 |
| gggggcccgc acaagcggtg gagcatgtgg tttaattcga agcaacgcga agaaccttac | 960 |

```
caggccttga catgctgaga acctgccaga gatggcgggg tgccttcggg aactcagaca    1020
caggtgctgc atggctgtcg tcagctcgtg tcgtgagatg ttgggttaag tcccgtaacg    1080
agcgcaaccc ttgtccttag ttaccagcac gttatggtgg gcactctaag gagactgccg    1140
gtgacaaacc ggaggaaggt ggggatgacg tcaagtcatc atggccctta cggcctgggc    1200
tacacacgtg ctacaatggt cggtacaaag ggttgccaag ccgcgaggtg gagctaatcc    1260
cataaaaccg atcgtagtcc ggatcgcagt ctgcaactcg actgcgtgaa gtcggaatcg    1320
ctagtaatcg tgaatcagaa tgtcacggtg aatacgttcc cgggccttgt acacaccgcc    1380
cgtcacacca tgggagtggg ttgctccaga agtagctagt ctaaccttcg gggggacggt    1440
taccacggag tgat                                                     1454

<210> SEQ ID NO 61
<211> LENGTH: 854
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas purida

<400> SEQUENCE: 61
tgggaactgc atccaaaact ggcgagctag agtatggcag agggtggtgg aatttcctgt      60
gtagcggtga aatgcgtaga tataggaagg aacaccagtg gcgaaggcga ccacctgggc     120
taatactgac actgaggtgc gaaagcgtgg agagcaaaca ggattagata ccctggtagt     180
ccacgccgta aacgatgtcg actagccgtt gggatccttg agatcttagt ggcgcagcta     240
acgcattaag tcgaccgcct ggggagtacg gccgcaaggt taaaactcaa atgaattgac     300
gggggcccgc acaagcggtg gagcatgtgg tttaattcga agcaacgcga agaaccttac     360
caggccttga catgcagaga actttccaga gatggattgg tgccttcggg agctctgaca     420
caggtgctgc atggctgtcg tcagctcgtg tcgtgagatg ttgggttaag tcccgtaacg     480
agcgcaaccc ttgtccttag ttaccagcac gttaaggtgg gcactctaag gagactgccg     540
gtgacaaacc ggaggaaggt ggggatgacg tcaagtcatc atggccctta cggcctgggc     600
tacacacgtg ctacaatggt cggtacaaag ggttgccaag ccgcgaggtg gagctaatcc     660
cataaaaccg atcgtagtcc ggatcgcagt ctgcaactcg actgcgtgaa gtcggaatcg     720
ctagtaatcg tgaatcagaa tgtcacggtg aatacgttcc cgggccttgt acacaccgcc     780
cgtcacacca tgggagtggg ttgctccaga agtagctagt ctaaccttcg gggggacggt     840
taccacggag tgat                                                       854

<210> SEQ ID NO 62
<211> LENGTH: 854
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas pseudoalcligenes

<400> SEQUENCE: 62
tgggaactgc atccaaaact ggcgagctag agtatggcag agggtggtgg aatttcctgt      60
gtagcggtga aatgcgtaga tataggaagg aacaccagtg gcgaaggcga ccacctgggc     120
taatactgac actgaggtgc gaaagcgtgg agagcaaaca ggattagata ccctggtagt     180
ccacgccgta aacgatgtcg actagccgtt gggatccttg agatcttagt ggcgcagcta     240
```

```
acgcattaag tcgaccgcct ggggagtacg gccgcaaggt taaaactcaa atgaattgac      300
gggggcccgc acaagcggtg gagcatgtgg tttaattcga agcaacgcga agaaccttac      360
caggccttga catgcagaga actttccaga gatggattgg tgccttcggg agctctgaca      420
caggtgctgc atggctgtcg tcagctcgtg tcgtgagatg ttgggttaag tcccgtaacg      480
agcgcaaccc ttgtccttag ttaccagcac gttaaggtgg gcactctaag gagactgccg      540
gtgacaaacc ggaggaaggt ggggatgacg tcaagtcatc atggccctta cggcctgggc      600
tacacacgtg ctacaatggt cggtacaaag ggttgccaag ccgcgaggtg gagctaatcc      660
cataaaaccg atcgtagtcc ggatcgcagt ctgcaactcg actgcgtgaa gtcggaatcg      720
ctagtaatcg tgaatcagaa tgtcacggtg aatacgttcc cgggccttgt acacaccgcc      780
cgtcacacca tgggagtggg ttgctccaga agtagctagt ctaaccttcg ggggacggt      840 taccacggag tgat                                                        854

<210> SEQ ID NO 63
<211> LENGTH: 1448
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium chartatabidium

<400> SEQUENCE: 63
tggctcagga cgaacgctgg cggcgtgcct aacacatgca agtcgagcgg agaatgcaga       60
aatgtttaca tggaagcgtt cttagcggcg gacgggtgag taacacgtgg gtaacctgcc      120
tcaaagtggg ggatagcctt ccgaaaggaa gattaatacc gcataagcct acagtgccgc      180
atggcacagc aggaaaagga gcaatccgct ttgagatgga cccgcggcgc attagctagt      240
tggtgaggta acggctcacc aaggcgacga tgcgtagccg acctgagagg gtgatcggcc      300
acattggaac tgagacacgg tccagactcc tacgggaggc agcagtgggg aatattgcac      360
aatgggcgaa agcctgatgc agcaacgccg cgtgagtgat gaaggccttc gggtcgtaaa      420
gctctttgat cagggatgat aatgacagta cctgaaaaac aagccacggc taactacgtg      480
ccagcagccg cggtaatacg taggtggcga gcgttgtccg gaattactgg gcgtaaagga      540
tgcgtaggtg atacttaagt gggatgtgaa atccccgggg ctcaacccgg gaactgcatt      600
ccaaactggg tatctagagt gcaggagagg aaagcggaat tcctagtgta gcggtgaaat      660
gcgtagatat taggaggaac accagtgcg aaggcggctt tctggactgt aactgacact      720
gaggcatgaa agcgtgggta gcaaacagga ttagataccc tggtagtcca cgccgtaaac      780
gatgggtact aggtgtagga ggtatcgacc ccttctgtgc cgtcgttaac acaataagta      840
ccccgcctgg ggagtacggt cgcaagacta aaactcaaag gaattgacgg gggcccgcac      900
aagcagcgga gcatgtggtt taattcgaag caacgcgaag aaccttacct agacttgaca      960
tctcctgaat taccCttaac cggggaagcc cttcgggcca ggaagacagg tggtgcatgg     1020
ttgtcgtcag ctcgtgtcgt gagatgttgg gttaagtccc gcaacgagcg caacccttat     1080
ttttagttgc taccatttgg ttgagcactc taaagagact gccgggtta accggaggga     1140 aggtggggat gacgtcaaat catcatgccc cttatgtcta gggctacaca cgtgctacaa     1200
tggtgagaac aaagagacgc gagaccgcga ggtggagcaa atctcataaa actcatccca     1260
gttcggattg caggctgaaa ctcgcctgca tgaagccgga gttgctagta atcgcgaatc     1320
agcatgtcgc ggtgaatacg ttcccgggcc ttgtacacac cgcccgtcac accatgagag     1380
```

```
ttggcaatac ccgaagtccg tggggcaacc agttaatgga gccagcggcc gaaggtaggg    1440
tcagcgat                                                             1448

<210> SEQ ID NO 64
<211> LENGTH: 1486
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 64
tggctcagga cgaacgctgg cggcgtgcct aacacatgca agtcgagcga agtgactcgg      60
agagaagttt tcgaatggat cgaagagtca tcttagcggc ggacgggtga gtaacgcgtg    120
agaaacctgc ctttcacaaa gggatagcct cgggaaactg ggattaatac cttatgaaac    180
tgaattaccg catggtagat cagtcaaagc gaataagcgg tgaaagatgg tctcgcgtcc    240
tattagctag ttggtgaggt aacggctcac caaggcttcg ataggtagcc ggcctgagag    300
ggtgaacggc cacactggaa ctgagacacg gtccagactc ctacgggagg cagcagtggg    360
gaatattgca caatggagga aactctgatg cagcgacgcc gcgtgaatga tgaaggcctt    420
cgggttgtaa agttctgtcc ttggggaaga taatgacggt acccaaggag gaagccccgg    480
ctaactacgt gccagcagcc gcggtaatac gtaggggcg agcgttgtcc ggaattattg     540
ggcgtaaagg gttcgcaggc ggtctgataa gtcagatgtg aaaggcgtag gctcaaccta    600
cgtaagcatt tgaaactgtc agacttgagt taaggagagg aaagtggaat tcctagtgta    660
gcggtgaaat gcgtagatat taagaggaat accagtggcg aaggcgactt tctggactta    720
tactgacgct taggaacgaa agcgtgggga gcaaacagga ttagataccc tggtagtcca    780
cgccgtaaac gatgagtgct aggtgttggg ggtcaaacct cggtgccgca gctaacgcat    840
taagcactcc gcctggggag tacgtacgca agtatgaaac tcaaaggaat tgacggggac    900
ccgcacaagc agcggagcat gtggtttaat tcgaagcaac gcgaagaacc ttaccagggc    960
ttgacatgcc gctgaccggt ttagagatag acctttatcc ttcggggtac agcggacaca   1020
ggtggtgcat ggttgtcgtc agctcgtgtc gtgagatgtt gggttaagtc ccgcaacgag   1080 cgcaacccctt gtctttagtt gccatcatta agttgggcac tctaaagaga ctgccgatga   1140
caaatcggag gaaggtgggg gtgacgtcaa atcatcatgc cctttatgtc ctgggctaca   1200
cacgtgctac aatggtcggt acaacgaaa gcaagccagc gatggcaagc aaatctctaa    1260
aagccgatcc cagttcggat tgcaggctgc aactcgcctg catgaagtcg gagttgctag   1320
taatcgcgga tcagaatgcc gcggtgaatg cgttcccggg tcttgtacac accgcccgtc   1380
acaccatggg agttgtcaat acccgaagcc agtgagctaa ccataaaagg gggcagctgt   1440
cgaaggtagg ggcaatgact ggggtgaagt cgtaacaagg taaccg                  1486

<210> SEQ ID NO 65
<211> LENGTH: 881
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 65
tggctcagga cgaacgctgg cggcgtgcct aacacatgca agtcgagcga agtgactcgg      60
```

```
agagaaattt tcggatggat cgaagagtca tcttagcggc ggacgggtga gtaacgcgtg      120
agaaacctgc ctttcacaaa gggatagcct cgggaaactg ggattaatac cttatgaaac      180
tgaattaccg catggtagat cagtcaaagc gaataagcgg tgaaagatgg tctcgcgtcc      240
tattagctag ttggtgaggt aacggctcac caaggcttcg ataggtagcc ggcctgagag      300
ggtgaacggc cacactggaa ctgagacacg gtccagactc ctacgggagg cagcagtggg      360
gaatattgca caatggagga aactctgatg cagcgacgcc gcgtgaatga tgaaggcctt      420
cgggttgtaa agttctgtcc ttggggaaga taatgacggt acccaaggag aagccccgg       480 ctaactacgt gccagcagcc gcggtaatac gtaggggggcg agcgttgtcc ggaattattg      540
ggcgtaaagg gttcgcaggc ggtctgataa gtcagatgtg aaaggcgtag gctcaaccta      600
cgtaagcatt tgaaactgtc agacttgagt taaggagagg aaagtggaat tcctagtgta      660
gcggtgaaat gcgtagatat taggaggaat accagtggcg aaggcgactt tctggactta      720
tactgacgct gaggaacgaa agcgtgggga gcaaacagga ttagataccc tggtagtcca      780
cgccgtaaac gatgagtgct aggtgttggg ggtcaaacct cggtgccgca gctaacgcat      840
taagcactcc gcctggggag tacgtacgca agtatgaaac t                         881
```

<210> SEQ ID NO 66
<211> LENGTH: 1393
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 66

```
tggctcagga cgaacgctgg cggcgtgcct aacacatgca agtcgagcga agtgactctg       60
agagaaattt tcggatggat cgaagagtca tcttagcggc ggacgggtga gtaacgcgtg      120
agaaacctgc ctttcacaaa gggatagcct cgggaaactg ggattaatac cttatgaaac      180
tgaattaccg catggtagat cagtcaaagc gaataagcgg tgaaagatgg tctcgcgtcc      240
tattagctag ttggtgaggt aacggctcac caaggcttcg ataggtagcc ggcctgagag      300
ggtgaacggc cacactggaa ctgagacacg gtccagactc ctacgggagg cagcagtggg      360
gaatattgca caatggagga aactctgatg cagcgacgcc gcgtgaatga tgaaggcctt      420
cgggttgtaa agttctgtcc ttggggaaga taatgacggt acccaaggag aagccccgg       480 ctaactacgt gccagcagcc gcggtaatac gtaggggggcg agcgttgtcc ggaattattg      540
ggcgtaaagg gttcgcaggc ggtctgataa gtcagatgtg aaaggcgtag gctcaaccta      600
cgtaagcatt tgaaactgtc agacttgagt taaggagagg aaagtggaat tcctagtgta      660
gcggtgaaat gcgcagatat taggaggaat accagtggcg aaggcgactt tctggactta      720
tactgacgct gaggaacgaa agcgtgggga gcaaacagga ttagataccc tggtagtcca      780
cgccgtaaac gatgagtgct aggtgttggg ggtcaaacct cggtgccgca gctaacgcat      840
taagcactcc gcctggggag tacgtacgca agtatgaaac tcaaaggaat tgacgggac      900 ccgcacaagc agcggagcat gtggtttaat tcgaagcaac gcgaagaacc ttaccagggc      960
ttgacatgcc gctgaccggt ttagagatag atctttatcc ttcggggtac ggcggacaca     1020
ggtggtgcat ggttgtcgtc agctcgtgtc gtgagatgtt gggttaagtc ccgcaacgag     1080
cgcaaccctt gtctttagtt gccatcatta agttgggcac tctaaagaga ctgccgatga     1140
caaatcggag gaaggtgggg atgacgtcaa atcatcatgc cctttatgtc ctgggctaca     1200
```

-continued

| cacgtgctac aatggtcggt acaacgagaa gcaagtcagc gatggcaagc aaatctctaa | 1260 |
| cagccgatcc cagttcggat tgcaggctgc aactcgcctg catgaagtcg gagttgctag | 1320 |
| taatcgcgga tcagaatgcc gcggtgaatg cgttcccggg tcttgtacac accgcccgtc | 1380 |
| acaccatggg agt | 1393 |

<210> SEQ ID NO 67
<211> LENGTH: 1440
<212> TYPE: DNA
<213> ORGANISM: unknown
<220> FEATURE:
<223> OTHER INFORMATION: Unknown clone from enriched environmental
      sample that by rDNA sequence analysis has highest identity to
      Thauera aromatica
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (667)..(667)
<223> OTHER INFORMATION: n is a, c, g, or t

<400> SEQUENCE: 67

| tggctcagat tgaacgctgg cggcatgctt tacacatgca agtcgaacgg cagcgggggc | 60 |
| ttcggcctgc cggcgagtgg cgaacgggtg agtaatgcat cggaacgtgc ccatgtcgtg | 120 |
| ggggataacg tatcgaaagg tacgctaata ccgcatacgt cctgagggag aaagtggggg | 180 |
| atcttcggac ctcacgctat cagatgagcc taggtcggat tagctagttg gcgaggtaaa | 240 |
| ggctcaccaa ggcgacgatc cgtagcgggt ctgagaggat gatccgccac actgggactg | 300 |
| agacacggcc cagactccta cgggaggcag cagtggggaa ttttggacaa tgggcgcaag | 360 |
| cctgatccag ccatgccgcg tgagtgaaga aggccttcgg gttgtaaagc tctttcggcc | 420 |
| gggaagaaat cgtggtctct aacataggcc atgatgacg gtaccggact aagaagcacc | 480 |
| ggctaactac gtgccagcag ccgcggtaat acgtagggtg cgagcgttaa tcggaattac | 540 |
| tgggcgtaaa gcgtgcgcag gcggttttgt aagacagatg tgaaatcccc gggctcaacc | 600 |
| tgggaactgc gtttgtgact gcaaggctag agtacgcag aaggggtgg aattcctggt | 660 |
| gtancantga aatgcgtaaa gatcaagagg aacaccgatg gcgaaagcag ccccctgggc | 720 |
| ctgtactgac cctcatgcac gaaagcgtgg ggagcaaaca agattaaata ccctggtagt | 780 |
| ccacgcccta aacgatgtcg actagtcgtt tggagcagca atgcactgag tgacgcagct | 840 |
| aacgcgtgaa gtcgaccgcc tggggagtac ggccgcaagg ttaaaactca aggaattga | 900 |
| cggggacccg cacaagcggt ggatgatgtg gattaattg atgcaacgcg aaaaacctta | 960 |
| cctacccttg acatgccagg aaccttgccg agaggcgagg gtgccttcgg gagcctggac | 1020 |
| acaggtgctg catggctgtc gtcagctcgt gtcgtgagat gttgggttaa gtcccgcaac | 1080 |
| gagcgcaacc cttgtcacta gttgccatca tttggttggg cactctagtg agactgccgg | 1140 |
| tgacaaaccg gaggaaggtg gggatgacgt caagtcctca tggcccttat gggtagggct | 1200 |
| tcacacgtca tacaatggtc ggtacagagg gttgccaagc cgcgaggtgg agccaatccc | 1260 |
| ttagagccga tcgtagtccg gatcgtagtc tgcaactcga ctacgtgaag tcggaatcgc | 1320 |
| tagtaatcgc agatcagcat gctgcggtga atacgttccc gggtcttgta cacaccgccc | 1380 |
| gtcacaccat gggagtgggt ttcaccagaa gtaggtagct aaccttcgg gagggcgctt | 1440 |

<210> SEQ ID NO 68
<211> LENGTH: 1452
<212> TYPE: DNA

<213> ORGANISM: unknown
<220> FEATURE:
<223> OTHER INFORMATION: Unknown clone from enriched environmental
sample that by rDNA sequence analysis has highest identity to
Thauera aromatica

<400> SEQUENCE: 68

| | | | | | |
|---|---|---|---|---|---|
| tggctcagga | cgaacgctga | cggcgtgcct | aacacatgca | agtcgagcgg | agaatgcaga | 60 |
| aatgtttaca | tggaagtatt | cttagcggcg | gacgggtgag | taacacgtgg | gtaacctgcc | 120 |
| tcaaagtggg | ggatagcctt | ccgaaaggaa | gattaatacc | gcataagcct | acagtgccgc | 180 |
| atggcacagc | aggaaaagga | gcaatccgct | ttgagatgga | cccgcggcgc | attagctagt | 240 |
| tggtgaggta | acggctcacc | aaggcgacga | tgcgtagccg | acctgagagg | gtgatcggcc | 300 |
| acattggaac | tgagacacgg | cccagactcc | tacgggaggc | agcagtgggg | aattttggac | 360 |
| aatgggcgca | agcctgatcc | agccatgccg | cgtgagtgaa | gaaggccttc | gggttgtaaa | 420 |
| gctctttcgg | ccgggaagaa | atcgtggtct | ctaacatagg | ccatggatga | cggtaccgga | 480 |
| ctaagaagca | ccggctaact | acgtgccagc | agccgcggta | atacgtaggg | tgcgagcgtt | 540 |
| aatcggaatt | actgggcgta | aagcgtgcgc | aggcggtttt | gtaagacaga | tgtgaaatcc | 600 |
| ccgggctcaa | cctgggaact | gcgtttgtga | ctgcaaagct | agagtacggc | agaagggggt | 660 |
| ggaattcctg | gtgtagcagt | gaaatgcgta | gagatcagga | ggaacaccga | tggcgaaggc | 720 |
| agccccctgg | ggcctgtact | gacgctcatg | cacgaaagcg | gggggagcaa | acaggattag | 780 |
| ataccctggt | agtccacgcc | ctaaacgatg | tcgactagtc | gttcggagca | gcaatgcact | 840 |
| gagtgacgca | gctaacgcgt | gaagtcgacc | gcctggggag | tacggccgca | aggttaaaac | 900 |
| tcaaaggaat | tgacggggac | ccgcacaagc | ggtggatgat | gtggattaat | tcgatgcaac | 960 |
| gcgaaaaacc | ttacctaccc | ttgacatgcc | aggaaccttg | ccgagaggcg | agggtgcctt | 1020 |
| cgggagcctg | gacacaggtg | ctgcatggct | gtcgtcagct | cgtgtcgtga | gatgttgggt | 1080 |
| taagtcccgc | aacgagcgca | acccttgtca | ctagttgcca | tcatttggtt | gggcactcta | 1140 |
| gtgagactgc | cggtgacaaa | ccggaggaag | gtgggggatga | cgtcaagtcc | tcatggccct | 1200 |
| tatgggtagg | gcttcacacg | tcatacaatg | gtcggtacag | agggttgcca | agccgcgagg | 1260 |
| tggagccaat | cccttaaagc | cgatcgtagt | ccggatcgta | gtctgcaact | cgactacgtg | 1320 |
| aagtcggaat | cgctagtaat | cgcagatcag | catgctgcgg | tgaatacgtt | cccgggtctt | 1380 |
| gtacacaccg | cccgtcacac | catgggagtg | ggtttcacca | gaagtaggta | gcttaacctt | 1440 |
| cgggagggcg | ct | | | | | 1452 |

<210> SEQ ID NO 69
<211> LENGTH: 1440
<212> TYPE: DNA
<213> ORGANISM: unknown
<220> FEATURE:
<223> OTHER INFORMATION: Unknown clone from enriched environmental
sample that by rDNA sequence analysis has highest identity to
Azoarcus sp. EH21

<400> SEQUENCE: 69

| | | | | | |
|---|---|---|---|---|---|
| tggctcagat | tgaacgctgg | cggcatgctt | tacacatgca | agtcgaacgg | cagcggggc | 60 |
| ttcggcctgc | cggcgagtgg | cgaacgggtg | agtaatgcat | cggaacgtgc | ccatgtcgtg | 120 |
| ggggataacg | tatcgaaagg | tacgctaata | ccgcatacgt | cctgagggag | aaagcggggg | 180 |
| atcttcggac | ctcgcgcgat | tggagcggcc | gatgtcggat | tagctagtag | gtgaggtaaa | 240 |
| ggctcaccta | ggcgacgatc | cgtagcgggt | ctgagaggat | gatccgccac | actgtgactg | 300 |

```
agacacggcc cagactccta cgggaggcag cagtggggaa ttttggacaa tgggcgcaag    360
cctgatccag ccatgccgcg tgagtgaaga aggccttcgg gttgtaaagc tctttcggcc    420
gggaagaaat cgtggtctct aacataggcc atggatgacg gtaccggact aagaagcacc    480
ggctaactac gtgccagcag ccgcggtaat acgtagggtg cgagcgttaa tcggaattac    540
tgggcgtaaa gcgtgcgcag gcggttttgt aagacagatg tgaaatcccc gggctcaacc    600
tgggaactgc gtttgtgact gcaaggctag agtacgcag aggggggtgg aattcctggt     660
gtaacaatga aatgcgtaga gatcaggagg aacacggatg cgaaggcag ccccctgggc     720
ctgtactgac gctcatgcac gaaagcgtgg ggagcaaaca ggattagata ccctggtagt    780
ccacgccgta acgatgtcg actagccgtt gggatccttg agatcttagt ggcgcagcta     840
acgcattaag tcgaccgcct ggggagtacg gccgcaaggt taaaactcaa atgaattgac    900
gggggcccgc acaagcggtg gagcatgtgg tttaattcga gcaacgcga gaaccttac      960
caggccttga catgcagaga actttccaga gatggattgg tgccttcggg agctctgaca   1020
caggtgctgc atggctgtcg tcagctcgtg tcgtgagatg ttgggttaag tcccgtaacg   1080
agcgcaaccc ttgtccttag ttaccagcac gttaaggtgg gcactctaag gagactgccg   1140
gtgacaaacc ggaggaaggt ggggatgacg tcaagtcatc atggccctta cggcctgggc   1200
tacacacgtg ctacaatggt cggtacaaag ggttgccaag ccgcgaggtg gagctaatcc   1260
cataaaaccg atcgtagtcc ggatcgtagt ctgcaactcg actacgtgaa gtcggaatcg   1320
ctagtaatcg cagatcagca tgctgcggtg aatacgttcc cgggtcttgt acacaccgcc   1380
cgtcacacca tgggagtggg tttcaccaga agtaggtagc ttaaccttcg ggagggcgct   1440
```

<210> SEQ ID NO 70
<211> LENGTH: 1438
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 70

```
tggctcagga cgaacgctgg cggcgtgcct aacacatgca agtcgagcga agtgactctg     60
agagaaattt tcggatggat cgaagagtca tcttagcggc ggacgggtga gtaacgcgtg    120
agaaacctgc ctttcacaaa gggatagcct cgggaaactg ggattaatac cttatgaaac    180
tgaattaccg catggtagat cagtcaaagc gaataagcgg tgaaagatgg tctcgcgtcc    240
tattagctag ttggtgaggt aacggctcac caaggcttcg ataggtagcc ggcctgagag    300
ggtgaacggc cacactggaa ctgagacacg gtccagactc ctacgggagg cagcagtggg    360
gaatattgca caatggagga aactctgatg cagcgacgcc gcgtgaatga tgaaggcctt    420
cggggttgtaa agttctgtcc ttggggaaga taatgacggt acccaaggag gaagcccgg    480
ctaactacgt gccagcagcc gcggtaatac gtagggtgcg agcgttaatc ggaattactg    540
ggcgtaaagc gtgcgcaggc ggttttgtaa gacagatgtg aaatccccgg ctcaacctg    600
ggaactgcgt ctgtgactgc aaggctagag tacggcagag gggggtggaa ttcctggtgt    660
agcagtgaaa tgcgtacaga tcacgaggaa caccgatggc gaaggcagcc cctggccct    720
gtactgacgt tcatgcacaa aagcgtgggg agcaaacagg gattagatac cctggtagtc    780
cacgccctaa cgatgttgaa ttagtcgttc ggagcagcaa tgcactgagt gacgcagcta    840
acgcgtgaag tcgaccgcct ggggagtacg gccgcaaggt taaaactcaa aggaattgac    900
```

| | |
|---|---|
| ggggacccgc acaagcggtg gatgatgtgg attaattcga tgcaacgcga aaaaccttac | 960 |
| ctacccttga catgccagga accttgccga gaggcgaggg tgccttcggg agcctggaca | 1020 |
| caggtgctgc atggctgtcg tcagctcgtg tcgtgagatg ttgggttaag tcccgcaacg | 1080 |
| agcgcaaccc ttgtcactag ttgccatcat ttggttgggc actctagtga gactgccggt | 1140 |
| gacaaaccgg aggaaggtgg ggatgacgtc aagtcctcat ggcccttatg ggtagggctt | 1200 |
| cacacgtcat acaatggtcg gtacagaggg ttgccaagcc gcgaggtgga gccaatccct | 1260 |
| taaagccgat cgtagtccgg atcgtagtct gcaactcgac tacgtgaagt cggaatcgct | 1320 |
| agtaatcgca gatcagcatg ctgcggtgaa tacgttcccg ggtcttgtac acaccgcccg | 1380 |
| tcacaccatg ggagtgggtt tcaccagaag taggtagctt aaccttcggg agggcgct | 1438 |

<210> SEQ ID NO 71
<211> LENGTH: 1437
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 71

| | |
|---|---|
| tggctcagat tgaacgctgg cggcaggcct aacacatgca agtcgagcgg atgagtggag | 60 |
| cttgctccat gattcagcgg cggacgggtg agtaatgcct aggaatctgc ctggtagtgg | 120 |
| gggacaacgt ttcgaaagga acgctaatac cgcatacgtc ctacgggaga agtgggggga | 180 |
| tcttcggacc tcacgctatc agatgagcct aggtcggatt agctagttgg tgaggtaaag | 240 |
| gctcaccaag gcgacgatcc gtaactggtc tgagaggatg atcagtcaca ctggaactga | 300 |
| gacacggtcc agactcctac gggaggcagc agtggggaat attggacaat gggcgaaagc | 360 |
| ctgatccagc catgccgcgt gtgtgaagaa ggtcttcgga ttgtaaagca ctttaagttg | 420 |
| ggaggaaggg cagtaagtta ataccttgct gttttgacgt taccgacaga ataagcaccg | 480 |
| gctaacttcg tgccagcagc cgcggtaata cgaagggtgc aagcgttaat cggaattact | 540 |
| gggcgtaaag cgcgcgtagg tggttcgtta agttggatgt gaaagccccg ggctcaacct | 600 |
| gggaactgca tccaaaacta gcgagctaga gtatggcaga gggtggtgga atttcctgtg | 660 |
| tagcggtgaa atgcgtagat ataggaagga acaccagtgg cgaaggcgac cacctggggt | 720 |
| aatactgaca ctgaagtgcg aaagcggggg gagcaaacag gattagatac cctggtattc | 780 |
| cacgccgtaa acgatgtcga ctagccgttg ggatccttga gatcttagtg gcgcagctaa | 840 |
| cgcattaagt cgaccgcctg gggagtacgg ccgcaaggtt aaaactcaaa ggaattgacg | 900 |
| gggacccgca caagcggtgg atgatgtgga ttaattcgat gcaacgcgaa aaaccttacc | 960 |
| taccccttgac atgccaggaa ccttgccgag aggcgagggt gccttcggga gcctggacac | 1020 |
| aggtgctgca tggctgtcgt cagctcgtgt cgtgagatgt gggttaagt cccgcaacga | 1080 |
| gcgcaaccct tgtcactagt tgccatcatt tggttgggca ctctagtgag actgccggtg | 1140 |
| acaaaccgga ggaaggtggg gatgacgtca agtcctcatg gcccttatgg gtagggcttc | 1200 |
| acacgtcata caatggtcgg tacagagggt tgccaagccg cgaggtggag ccaatccctt | 1260 |
| aaagccgatc gtagtccgga tcgtagtctg caactcgact acgtgaagtc ggaatcgcta | 1320 |
| gtaatcgcag atcagcatgc tgcggtgaat acgttcccgg gtcttgtaca caccgcccgt | 1380 |
| cacaccatgg gagtgggttt caccagaagt aggtagctta accttcggga gggcgct | 1437 |

<210> SEQ ID NO 72

```
<211> LENGTH: 1452
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 72
agagtttgat tctggctcag attgaacgct ggcggcatgc tttacacatg caagtcgaac       60
ggcagcgggg gcttcggcct gccggcgagt ggcgaacggg tgagtaatgc atcggaacgt      120
gcccatgtcg tgggggataa cgtatcgaaa ggtacgctaa taccgcatac gtcctgaggg      180
agaaagcggg ggatcttcgg acctcgcgcg attggagcgg ccgatgtcgg attagctagt      240
aggtgaggta aaggctcacc taggcgacga tccgtagcgg gtctgagagg atgatccgcc      300
acactgggac tgagacacgg cccagactcc tacgggaggc agcagtgggg aattttggac      360
aatgggcgca agcctgatcc agccatgccg cgtgagtgaa gaaggccttc gggttgtaaa      420
gctctttcgg ccgggaagaa atcgtggtct ctaacatagg ccatggttga cgttaccgac      480
agattaagca ccggctaact tcgtgccagc agccgcggta atacgaaggg tgcaagcgtt      540
aatcggaatt actgggcgta aagcgcgcgt aggtggttcg ttaagttgga tgtgaaagcc      600
ccgggctcaa cctgggaact gcatccaaaa ctggcgagct agagtatggc agagggtggt      660
ggaatttcct gtgtagcggt gaaatgcgta catataggaa ggaacaccag tggcgaaggc      720
gaccacctgg gctaatactg acactgaggt gcgaaagcgt ggggagcaaa caggattaga      780
taccctggta gtccacgccg taaacgatgt cgactagccg ttgggatcct tgagatctta      840
gtggcgcagc taacgcatta agtcgaccgc ctggggagta cggccgcaag gttaaaactc      900
aaatgaattg acggggccc gcacaagcgg tggagcatgt ggtttaattc gaagcaacgc       960
gaagaacctt accaggcctt gacatgctga gaacctgcca gagatggcgg ggtgccttcg     1020
ggaactcaga cacaggtgct gcatggctgt cgtcagctcg tgtcgtgaga tgttgggtta     1080
agtcccgtaa cgagcgcaac ccttgtcctt agttaccagc acgttatggt gggcactcta     1140
aggagactgc cggtgacaaa ccggaggaag gtggggatga cgtcaagtca tcatggccct     1200
tacggcctgg gctacacacg tgctacaatg gtcggtacaa agggttgcca agccgcgagg     1260
tggagctaat cccataaaac cgatcgtagt ccggatcgca gtctgcaact cgaccgcgtg     1320
aagtcggaat cgctagtaat cgtgaatcag aatgtcacgg tgaatacgtt cccgggcctt     1380
gtacacaccg cccgtcacac catggggggtg ggttgctcca gaagtagcta gtctaacctt     1440
cggggggacg gt                                                         1452

<210> SEQ ID NO 73
<211> LENGTH: 893
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 73
cggttacctt gttacgactt caccctcctc gccggacgta ccttcggaac cgccccccct       60
cgcgggttgg gctggcgact tcgggtaccc ccgactcgga tggtgtgacg ggcggtgtgt      120
acaaggcccg ggaacgtatt caccgcgcca tgctgatgcg cgattactag cgattccaac      180
ttcatggagt cgggttgcag actccaatcc gtactgggac cggctttaag ggattggctc      240
```

```
cacctcgcgg cttggcaacc ctctgtaccg accattgtat gacgtgtgaa gccctaccca     300
taagggccat gaggacttga cgtcatcccc accttcctcc ggtttgtcac cggcagtctc     360
actagagtgc ccaaccaaat gatggcaact agtgacaagg gttgcgctcg ttgcgggact     420
taacccaaca tctcacgaca cgagctgacg acagccatgc agcacctgtg tccaggctcc     480
cgaaggcacc ctcgcctctc ggcaaggttc ctggcatgtc aagggtaggt aaggtttttc     540
gcgttgcatc gaattaatcc acatcatcca ccgcttgtgc gggtcccgtt caattccttt     600
gagttttaac cttgcggccg tactccccag gcggtcgact tcacgcgtta gctgcgtcac     660
tcagtgcatt gctgctccga acgactagtc gacatcgttt agggcgtgga ctaccagggt     720
atctaatcct gtttgctccc cacgctttcg tgcatgagcg tcagtacagg cccaggggc     780 tgccttcgcc atcggtgttc ctcctgatct ctacgcattt cactgctaca ccaggaattc     840 caccccctc tgccgtactc tagccttgca gtcacaaacg cagttcccag gtt            893

<210> SEQ ID NO 74
<211> LENGTH: 846
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 74
agcggtttgt agacagatgt gaatcccggc tcaactggac tgcgtttgat gcaagctaga      60
gtcgcagagg gggggaatct gtgtagcagt gaatgcgtag agatcagagg acacgatgcg     120
aagcagcccc tgggctgtac tgacgtcatg cacgaaagcg ggggagcaaa caggattaga     180
tacctggtag tcacgcctaa acgatgtcga ctagtcgtcg gagcagcaat gcactgagtg     240
acgcagctaa cgcgtgaagt cgaccgctgg ggagtacggc cgcaaggtta aaactcaaag     300
gaattgacgg ggacccgcac aagcggtgga tgatgtggat taattcgatg caacgcgaaa     360
aaccttacct acccttgaca tgccaggaac cttgccgaga ggcgagggtg ccttcgggag     420
cctggacaca ggtgctgcat ggctgtcgtc agctcgtgtc gtgagatgtt gggttaagtc     480
ccgcaacgag cgcaacccct gtcactagtt gccatcattt ggttgggcac tctagtgaga     540
ctgccggtga caaaccggag gaaggtgggg atgacgtcaa gtcctcatgg cccttatggg     600
tagggcttca cacgtcatac aatggtcggt acagagggtt gccaagccgc gaggtggagc     660
caatccctta aagccgatcg tagtccggat cgtagtctgc aactcgacta cgtgaagtcg     720
gaatcgctag taatcgcaga tcagcatgct gcggtgaata cgttcccggg tcttgtacac     780
accgcccgtc acaccatggg agtgggtttc accagaagta ggtagcttaa ccttcgggag     840
ggcgct                                                                846

<210> SEQ ID NO 75
<211> LENGTH: 1426
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium chartatabidium

<400> SEQUENCE: 75
tggctcagga cgaacgctgg cggcgtgcct aacacatgca agtcgagcgg agaatgcaga      60
aatgtttaca tggaagtatt cttagcggcg gacgggtgag taacacgtgg gtaacctgcc     120
```

```
tcgaagtggg ggatagcctt ccgaaaggaa gattaatacc gcataagcct acagtgccgc    180
atggcacagc aggaaaagga gcaatccgct ttgagatgga cccgcggcgc attagctagt    240
tggtgaggta acggctcacc aaggcgacga tgcgtagccg acctgagagg gtgatcggcc    300
acattggaac tgagacacgg tccagactcc tacgggaggc agcagtgggg aatattgcac    360
aatgggcgaa agcctgatgc agcaacgccg cgtgagtgat gaaggccttc gggtcgtaaa    420
gctctttgat cagggatgat aatgacagta cctgaaaaac aagccacggc taactacgtg    480
ccagcagccg cggtaatacg taggtggcga cgttgtccg gaattactgg gcgtaaagga     540
tgcgtaggtg gatacttaag tgggatgtga atccccggg ctcaacccgg gaactgcatt     600
ccaaactggg tatctagagt gcaggagagg aaagcggaat tcctagtgta gcggtgaaat    660
gcgtagatat taggaggaac accagtggcg aaggcggctt tctggactgt aactgacact    720
gaggcatgaa agcgtgggta gcaaacagga ttagataccc tggtagtcca cgccgtaaac    780
gatgggtact aggtgtagga ggtatcgacc ccttctgtgc cgttgttaac acaataagta    840
ccccgcctgg ggagtacggt cgcaagacta aaactcaaag gaattgacgg ggcccgcac    900 aagcagcgga gcatgtggtt taattagaag caacgcgaaa aaccttacct acccttgaca    960
tgccaggaac cttgccgaga ggcgagggtg ccttcgggag cctggacaca ggtgctgcat   1020
ggctgtagtc agctcgtgtc gtgagatgtt gggttaagtc cgcaacgag cgcaaccctt    1080 gtcactagtt gccatcattt ggttgggcac tctagtgaga ctgccggtga caaaccggag   1140
gaaggtgggg atgacgtcaa gtcctcatgg cccttatggg tagggcttca cacgtcatac   1200
aatggtcggt acagagggtt gccaagtcgt gaggtggagc caatcccta aagccgatcg    1260 tagtccggat cgtagtctgc aactcgacta cgtgaagtcg gaatcgctag taatcgcaga   1320
tcagcatggt gcggtgaata cgttcccggg tcttgtacac accgcccgtc acaccatggg   1380
agtgggtttc accagaagta ggtagcttaa ccttcgggag ggcgct                  1426
```

<210> SEQ ID NO 76
<211> LENGTH: 1420
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium aceticum

<400> SEQUENCE: 76

```
tggctcagat tgaacgctgg cggcatgctt tacacatgca agtcgaacgg cagcggggc      60 ttcggcctgc cggcgagtgg cgaacgggtg agtaatgcat cggaacgtgc ccatgtcgtg    120
ggggataacg tatcgaaagg tacgctaata ccgcatacgt cctgagggag aaagcggggg    180
atcttcggac ctcgcgcgat tggagcggcc gatgtcggat tagctagtag gtgaggtaaa    240
ggctaaccta ggcgacgatc cgtagcgggt ctgagagggt gaacggccac actgaactg     300 agacacggtc cagactccta cgggaggcag cagtgggaa tattgcacaa tggaggaaac    360
tctgatgcag cgacgccgcg tgaatgatga aggccttcgg gttgtaaagt tctgtccttg    420
gggaagataa tgacggtacc caaggaggaa gccccggcta actacgtgcc agcagccgcg    480
gtaatacgta gggggcgagc gttgtccgga attattgggc gtaaagggtt cgcaggcggt    540
ctgataagtc agatgtgaaa ggcgtaggct caacctacgt aagcatttga aactgtcaga    600
cttgagttaa ggagaggaaa gtggaattcc tagtgtagcg gtgaaatgcg tagatattag    660
gaggaatacc agtggcgaag gcgactttct ggacttatac tgacgctgag gaacgaaagc    720
```

```
gtggggagca aacaggatta gatacccggg tagtccacgc cgtaaacgat gagtgctagg      780
tgttgggggt caaacctcgg tgccgcagct aacgcattaa gcactccgcc tggggagtac      840
gtacgcaagt atgaaactca aggaattga cggggacccg cacaagcagc ggagcatgtg      900
gtttaattcg aagcaacgcg aagaaccta ccagggcttg acatgccgct gaccggttta      960
gagatagatc tttacccttc ggggtacagc ggacacaggt ggtgcatggt tgtcgtcagc     1020
tcgtgtcgtg agatgttggg ttaagtcccg caacgagcgc aacccttgtc tttagttgcc     1080
atcattaagt tgggcactct aaagagactg ccgatgacaa atcggaggaa ggtggggatg     1140
acgtcaaatc atcatgccct ttatgtcctg gctacacac gtgctacaat ggtcggtaca      1200
acgagaagca agtcagcgat ggcaagcaaa tctctaaaag ccgatcccag ttcggattgc     1260
aggctgcaac tcgcctgcat gaagtcgag ttgctagtaa tcgcggatca gaatgccgcg      1320
gtgaatgcgt tcccgggtct tgtacacacc gcccgtcaca ccatgggagt tgtcaatacc     1380
cgaagccagt gagctaacca taaaaggagg cagctgtcga                            1420
```

<210> SEQ ID NO 77
<211> LENGTH: 1430
<212> TYPE: DNA
<213> ORGANISM: unknown
<220> FEATURE:
<223> OTHER INFORMATION: Unknown clone from enriched environmental
      sample that by rDNA sequence analysis has highest identity to
      Deferribacter desulfuricans

<400> SEQUENCE: 77

```
agagtttgat tatggctcag aacgaacgct ggcggcgtgc ttaacacatg caagtcaagg       60
agaaagtctc ttcgggggcg agtaaactgg cgcacgggtg agtaacgcgt gaggaacctg      120
cccatatgtc tgggataacc tgctgaaaag cgggctaata ctggatatat tgtttaccgc     180
atggtggaca aggaaagttg gtgtaagcta acgcatatgg atggtctcgc gtctgattag      240
ctagttggtg gggtaaaggc tcaccaaggc aacgatcagt agcgggtctg agaggatgat      300
ccgccacact gggactgaga cacggcccag actcctacgg gaggcagcag tggggaatat     360
tgcacaatgg gcgaaagcct gatgcagcaa cgccgcgtga gtgatgaagg ccttcgggtc      420
gtaaagctct ttgatcaggg atgataatga cagtacctga aaaacaagcc acggctaact     480
acgtgccagc agccgcggta atacgtatgt ggcgagcgtt gtccggaatt attgggcgta      540
aagggttcgc aggcggtctg ataagtcaga tgtgaaaggc gtaggctcaa cctacgtaag     600
catttgaaac tgtcagactt gagttaagga gaggaaagtg gaattcctag tgtagcggtg      660
aaatgcgtag atattaggag gaataccagt ggcgaaggcg actttctgga cttatactga     720
cgctgaggaa cgaaagcgtg gggagcaaac aggattagat accctggtag tccacgccgt      780
aaacgatgag tgctaggtgt tgggggtcaa acctcggtgc cgcagctaac gcattaagca     840
ctccgcctgg ggagtacgta cgcaagtatg aaactcaaag gaattgacgg ggacccgcac      900
aagcagcgga gcatgtggtt taattcgaag caacgcgaag aaccttacca gggcttgaca     960
tgccgctgac cggtttagag atagatcttt acccttcggg gtacgcgga cacaggtggt      1020 gcatggttgt cgtcagctcg tgtcgtgaga tgttggtta agtcccgcaa cgagcgcaac     1080
ccttattttt agttgctacc attcagttga gcactctaaa gagactgccc gggttaaccg     1140
ggaggaaggt ggggatgacg tcaaatcatc atgcccctta tgtctagggc tacacacgtg    1200
ctacaatggc cggtacagag ggttgccaag ccgcgaggtg gagccaatcc cttaaagccg     1260
atcgtagtcc ggatcgtagt ctgcaactcg actacgtgaa gtcggaatcg ctagtaatcg     1320
```

```
cagatcagca tgctgcggtg aatacgttcc cgggtcttgt acacaccgcc cgtcacacca    1380
tgggagtggg tttcaccaga agtaggtagc ttaaccttcg ggagggcgct              1430

<210> SEQ ID NO 78
<211> LENGTH: 1436
<212> TYPE: DNA
<213> ORGANISM: unknown
<220> FEATURE:
<223> OTHER INFORMATION: Unknown clone from enriched environmental
      sample that by rDNA sequence analysis has highest identity to
      Bacteroides sp. EH30

<400> SEQUENCE: 78
tggctcagga tgaacgctag cggcaggctt aatacatgca agtcgaacgg gattcgaggt     60
agcaatactt tgatgagagt ggcgcacggg tgcgtaacgc gtatgcaacc tacctttaac   120
tgggagatag ccccgagaaa tcgggattaa taccccataa cattacgaat ggcatcaat    180 ttgtgattaa agctccggcg gttagagatg ggcatgcgtg acattagctg gttggtgagg   240
taacggctca ccaaggcaac gatgtctagg ggtcctgaga gggttatccc ccacactggt   300
actgagacac ggaccagact cctacgggag gcagcagtaa ggaatattgg tcaatgggcg   360
caagcctgaa ccagccatgc cgcgtgcagg aagacggccc tatggttgt aaactgcttt    420 tatcagggaa taaaccccg ctcgtgagcg gggctgaagg tacctgagga ataagcatcg    480
gctaactccg tgccagcagc cgcggtaata cggaggatgc aagcgttatc cggattcatt   540
gggtttaaag ggtgcgcagg cggattggta agtcaggggt gaaatcccac agctcaactg   600
tggaactgcc tttgatactg tcagtctaga gtatagttga agttggcgga atgtgtcatg   660
tagcggtgaa atgcttagat atgacacaga acaccgatcg cgaaggcagc tagctaagct   720
ataactgacg ctcatgcacg aaagcgtggg gatcaaacag gattagatac cctggtagtc   780
cacgctgtaa acgatgatta ctcgatgttg cgatacaca gtcagcgttt gagcgaaagc    840
aataagtaat ccacctgggg agtacggccg caaggttaaa actcaaatga attgacgggg   900
gcccgcacaa gcggtggagc atgtggttta attcgaagca acgcgaagaa ccttaccagg   960
ccttgacatg cagagaactt tccagagatg gattggtgcc ttcgggagct ctgacacagg  1020
tgctgcatgg ctgtcgtcag ctcgtgtcgt gagatgttgg gttaagtccc gtaacgagcg  1080
caacccttgt ccttagttac cagcacgtta aggtgggcac tctaaggaga ctgccggtga  1140
caaaccggag gaaggtgggg atgacgtcaa gtcatcatgg cccttacggc ctgggctaca  1200
cacgtgctac aatggtcggt acaaagggtt gccaagccgc gaggtggagc taatcccata  1260
aaaccgatcg tagtccggat cgcagtctgc aactcgactg cgtgaagtcg gaatcgctag  1320
taatcgtgaa tcagaatgtc acggtgaata cgttcccggg ccttgtacac accgcccgtc  1380
acaccatggg agtgggtttc accagaagta ggtagcttaa ccttcgggag gcgct        1436

<210> SEQ ID NO 79
<211> LENGTH: 1439
<212> TYPE: DNA
<213> ORGANISM: unknown
<220> FEATURE:
<223> OTHER INFORMATION: Unknown clone from enriched environmental
      sample that by rDNA sequence analysis has highest identity to
      Finegoldia magna

<400> SEQUENCE: 79
tggctcagga cgaacgctgg cggcgtgcct aacacatgca agtcgagcga agtgactcgg     60
agagaagttt tcggatggat cgaagagtca tcttagcggc ggacgggtga gtaacgcgtg   120
```

-continued

| | |
|---|---|
| agaaacctgc ctttcacaaa gggatagcct cgggaaactg ggattaatac cttatgaaac | 180 |
| tgaattaccg catggtagat cagtcaaagc gaataagcgg tgaaagatgg tctcgcgtcc | 240 |
| tattagctag ttggtgaggt aacggctcac caaggcttcg ataggtagcc ggcctgagag | 300 |
| ggtgaacggc cacactggaa ctgagacacg gtccagactc ctacgggagg cagcagtggg | 360 |
| gaatattgca caatggagga aactctgatg cagcgacgcc gcgtgaatga tgaaggcctt | 420 |
| cgggttgtaa agttctgtcc ttggggaaga taatgacggt acccaaggag aagccccgg | 480 |
| ctaactacgt gccagcagcc gcggtaatac gtaggggggcg agcgttgtcc ggaattattg | 540 |
| ggcgtaaagg gttcgcaggc ggtctgataa gtcagatgtg aaaggcgtag gctcaaccta | 600 |
| cgtaagcatt tgaaactgtc agacttgagt taaggagagg aaagtggaat tcctagtgta | 660 |
| gcggtgaaat gcgtagatat taggaggaat accagtggcg aaggcgactt tctggactta | 720 |
| tactgacgct gaggaacgaa agcgtgggga gcaaacagga ttagataccc tggtaattcc | 780 |
| cgccgtaaac gatgagtgct aggtgttggg ggtcaaacct cggtgccgca gctaacgcat | 840 |
| taagcactcc gcctggggag tacgtacgca agtatgaaac tcaaaggaat tgacggggac | 900 |
| ccgcacaagc agcggagcat gtggtttaat ttgaagcaac gcgaagaacc ttaccagggc | 960 |
| ttgacatgcc gctgaccggt gcagagatgc atctttatcc ttcggggtac agcggacaca | 1020 |
| ggtggtgcat ggttgtcgtc agctcgtgtc gtgagatgtt gggttaagtc ccgcaacgag | 1080 |
| cgcaacccct gtctttagtt gccatcatta agttgggcac tctaaagaga ctgccgatga | 1140 |
| caaatcggag gaaggtgggg atgacgtcaa atcatcatgc cctttatgtc ctgggctaca | 1200 |
| cacgtgctac aatggtcggt acaacgagaa gcaagtcagc gatggcaagc aaatctctaa | 1260 |
| aagccgatcc cagttcggat tgcagtctgc aactcgactg catgaagtcg gaatcgctag | 1320 |
| taatcgcagg tcagcaaaac tgcggtgaat acgttcccgg gccttgtaca caccgcccgt | 1380 |
| cacaccacgg gagtcggttg tacctgaagc cggtggccca accgcaaggg gggagccgt | 1439 |

<210> SEQ ID NO 80
<211> LENGTH: 882
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas putida

<400> SEQUENCE: 80

| | |
|---|---|
| tggctcagat tgaacgctgg cggcatgctt tacacatgca agtcgaacgg cagcggggc | 60 |
| ttcggcctgc cggcgagtgg cgaacgggtg agtaatgcct aggaatctgc ctggtagtgg | 120 |
| gggacaacgt ttcgaaagga acgctaatac cgcatacgtc ctacgggaga agtgggggga | 180 |
| tcttcggacc tcacgctatc agatgagcct aggtcggatt agctagttgg tgaggtaaag | 240 |
| gctcaccaag gcgacgatcc gtaactggtc tgagaggatg atcagtcaca ctggaactga | 300 |
| gacacggtcc agactcctac gggaggcagc agtggggaat attggacaat gggcgaaagc | 360 |
| ctgatccagc catgccgcgt gtgtgaagaa ggtcttcgga ttgtaaagca ctttaagttg | 420 |
| ggaggaaggg cagtaagtta ataccttgct gttttgacgt taccgacaga ataagcaccg | 480 |
| gctaacttcg tgccagcagc cgcggtaata cgaagggtgc aagcgttaat cggaattact | 540 |
| gggcgtaaag cgcgcgtagg tggttcgtta agttagatgt gaaagccccg ggctcaacct | 600 |
| gggaactgca tccaaaactg gcgagctaga gtatggcaga gggtggtgga atttcctgtg | 660 |
| tagcggtgaa atgcgtagat ataggaagga acaccagtgg cgaaggcgac cacctgggct | 720 |

```
aatactgaca ctgaggtgcg aaagcgtggg gagcaaacag gattagatac cctggtagtc        780
cacgccgtaa acgatgtcga ctagccgttg ggatccttga gatcttagtg gcgcagctaa        840
cgcattaagc gtaccgcctg gggagtacgg ccgcaaggtt ga                           882
```

<210> SEQ ID NO 81
<211> LENGTH: 1442
<212> TYPE: DNA
<213> ORGANISM: unknown
<220> FEATURE:
<223> OTHER INFORMATION: Unknown clone from enriched environmental
      sample that by rDNA sequence analysis has highest identity to
      Clostridium aceticum

<400> SEQUENCE: 81

```
tggctcagga tgaacgctgg cggcgtgcct aacacatgca agtcgagcgg tatatagtgg         60
aatgaaactt cggtcgagtg aagctataga gagcggcgga cgggtgagta acgcgtaggc        120
aacctgcccc atacagaggg atagcctcgg gaaaccggga ttaaaacctc ataacgcgag        180
gagttcacat ggactgctcg ccaaagattc atcggtatgg gatgggcctg cgtctgatta        240
gctagttggt gaggtaacgg ctcaccaagg cgacgatcag tagccgacct gagagggtaa        300
tcggccacat tggaactgag acacggtcca aactcctacg ggaggcagca gtggggaatt        360
ttgcacaatg ggggcaaccc tgatgcagcg acgccgcgtg aacgaggaag gccttcgggt        420
cgtaaagttc tttcgacggg aagaaatgt tatacgagta actgcgtata atttgacggt        480
acctgtagaa gcagccccgg ctaactccgt gccagcagcc gcggtaatac ggaggggggcg       540 agcgttgttc ggagttactg ggcgtaaagc gcacgtaggc ggtgcggtaa gtcagggggtt       600 aaaggtcaca gctcaactgt gataaggcct ttgatactat cgtgctagag tgtcagagag        660
ggtagcggaa ttcccggtgt agcggtgaaa tgcgtagata tcgggaggaa caccagtagc        720
gaaggcggct acctggctga taactgacgc tgaggtgcga gagcgtgggg agcaaacagg        780
attagatacc ctggtagtcc acgctgtaaa cgatggacgt taggtgttgg gggaaccgac        840
cccctcagtg ccaagctaa cgcgttaaac gtcccgcctg gggagtacgg ccgcaaggtt        900
gaaactcaaa ggaattgacg ggggcccgca caagcggtgg agcatgtggt ttaattcgaa        960
gcaacgcgca gaaccttacc agcccttgac ataccggtcg cggacacaga gatgtgtctt       1020
tcagttcggc tggaccggat acaggtgctg catggctgtc gtcagctcgt gccgtgagat       1080
gttgggttaa gtcccgcaac gagcgcaacc ctcgcccttat gttgccagca tttagttggg      1140
cactctaagg ggactgccgg tgataagccg agaggaaggt ggggatgacg tcaagtcctc       1200
atggccctta cgggctgggc tacacacgtg ctacaatggt ggtgacagtg ggcagcgagc       1260
acgcgagtgt gagctaatct ccaaaagcca tctcagttcg gattgcactc tgcaactcga       1320
gtgcatgaag ttggaatcgc tagtaatcgc ggatcagcat gccgcggtga atacgttccc       1380
gggccttgta cacaccgccc gtcacaccat gggagttggt tttacccgaa ggcgctgtgc       1440
ta                                                                     1442
```

<210> SEQ ID NO 82
<211> LENGTH: 861
<212> TYPE: DNA
<213> ORGANISM: unknown
<220> FEATURE:
<223> OTHER INFORMATION: Unknown clone from enriched environmental
      sample that by rDNA sequence analysis has highest identity to
      Anaerovorax sp. EH34

<400> SEQUENCE: 82

```
gtgaaaggca atagcttaac tattgtaagc cttgcgaact gtgtggcttg agtgcaggag     60
aggaaagtgg aattcctagt gtagcggtga aatgcgtaga tattaggagg aacaccagtg    120
gcgaaggcga ctttctggac tgtaactgac actgaggcac gaaagcgtgg gagcaaacag    180
gattagatac cctggtagtc cacgccgtaa acgatgagca ctaggtgtcg gggtcgcaag    240
acttcggtgc cgcagttaac gcattaagtg ctccgcctgg ggagtacgca cgcaagtgtg    300
aaactcaaag gaattgacgg ggacccgcac aagcagcgga gcatgtggtt taattcgaag    360
caacgcgaag aaccttacca gggcttgaca tccctctgac agtcccttaa ccgggacctt    420
cttcggacag aggagacagg tggtgcatgg ttgtcgtcag ctcgtgtcgt gagatgttgg    480
gttaagtccc gcaacgagcg caacccttgt ctttagttgc catcattcag ttgggcactc    540
tagagagact gccgaggata actcggagga aggtggggat gacgtcaaat catcatgccc    600
cttatgccct gggctacaca cgtgctacaa tggctggtac aaagagacgc aagaccgcga    660
ggtggagcaa atctcaaaaa ccagtcccag ttcggattgc aggctgcaac tcgcctgcat    720
gaagttggag ttgctagtaa tcgcagatca gaatgctgcg gtgaatgcgt tcccgggtct    780
tgtacacacc gcccgtcaca ccatgggagt tgtcaatacc cgaagccagt gagctaacca    840
taaaaggagg cagctgtcga a                                              861
```

<210> SEQ ID NO 83
<211> LENGTH: 620
<212> TYPE: DNA
<213> ORGANISM: unknown
<220> FEATURE:
<223> OTHER INFORMATION: Unknown clone from enriched environmental
      sample that by rDNA sequence analysis has highest identity to
      Pseudomonas putida

<400> SEQUENCE: 83

```
tggctcagat tgaacgctgg cggcaggcct aacacatgca agtcgagcgg atgaatggag     60
cttgctccat gattcagcgg cggacgggtg agtaatgcct aggaatctgc ctggtagtgg    120
gggacaacgt ttcgaaagga acgctaaatac cgcatacgtc ctacgggaga agtgggggga    180
tcttcggacc tcacgctatc agatgagcct aggtcggatt agctagttgg cgaggtaaag    240
gctcaccaag gcgacgatcc gtaactggtc tgagaggatg atcagtcaca ctggaactga    300
gacacggtcc agactcctac gggaggcagc agtggggaat attggacaat gggcgaaagc    360
ctgatccagc catgccgcgt gtgtgaagaa ggtcttcgga ttgtaaagca ctttaagttg    420
ggaggaaggg cagtaagtta ataccttgct gttttgacgt taccgacaga ataagcaccg    480
gctaacttcg tgccagcagc cgcggtaata cgtaaggtgc gagcgttaat cggaattact    540
gggcgtaaag cgtgcgcagg cggttttgta agacagatgt gaaatccccg ggctcatcct    600
gggaactgcg tctgtgactg                                                620
```

<210> SEQ ID NO 84
<211> LENGTH: 854
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 84

```
gccctgggct caacatgggc atccatccag acaggcgagc tagagtatag cagaggggtg     60
gtgtaatttc cagcgtagcg atgaaatgag ttgagatagg aagccacacc agaagggaag    120
```

-continued

```
cagaccacct gggataatca tgacagtgag gtacgaaagc gtgcggagca acaagataa      180 catacccgtg cagtccatgc agtaaatgat gtcgcctagc cgatgggatc catcagatcg     240
gagcggcgca gctaatgcac taagtgcacc gcgtggggag tacggccgca aggtttcaaa    300
tcaaatgaat tggcggggga ccgcacaagc ggcgcagcat gtggtttaat tcgaagcaac    360
gagcagaacc ttaccaggcc atcccatgca tagaactttc cagagaggga tcggggcctt    420
ccggaggtgt gacaccggtg gcgccaggcc gttgttaagt tgggtcctgg gatggtgggg   480
taaattccgt aacagagggc aaccctgtct ttagttaccc acccgttaag gtgggcactc    540
taaggagacc gccggggaca aaccggagga aggtggggat gacgtcaagt catcatggcc    600
cttacggcct gggctacaca cgtgctacaa tggtcggtac aaagggttgc caagccgcga    660
ggtggagcta atcccataaa accgatcgta gtccggatcg cagtctgcaa ctcgactgcg   720
tgaagtcgga atcgctagta atcgtgaatc agaatgtcac ggtgaatacg ttcccgggcc   780
ttgtacacac cgcccgtcac accatgggag tgggttgctc cagaagtagc tagtctaacc    840
ttcgggggga cggt                                                      854
```

<210> SEQ ID NO 85
<211> LENGTH: 824
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azotobacter beijerinckii

<400> SEQUENCE: 85

```
caaatctcgc ctcaactcgc gcttggtttg catgcagctt cgtagtgtga gcgagtggat    60
cctgcttgca atgaatgagt caagtcagat ggagcacgga tggcagggat ctcctcgcgc   120
atgtactacg tcttgcacgc aagagtgagg agcaaacaag caatagctac ctgttactcc    180 tcccctcaa tgatgatgat tattagtcgt agcagcaaaa ctctggtgtc gaagctaata    240
cggaagtctc acctggggag tactgcgcat tataaatact caaaggattt tggtgtcgcc   300
ccccagcggg gatatgtgga ttaattagat gaaacgcgaa aaaccttccc tcccctcgac   360
atacgacgaa ccctttgaga ggggagggtg cttttgggag cctggacaca ggtgccgcat   420
gggtgtcgtc acctcgtgtc gtgagatgtt gggttatgtc tcgcaacgag cgcaacccct   480
gtcactagcg ccatcatttg gggggcact ctagtgagac cccggtgaca aaccggagga   540 agggggggg gacgtcaagt cctcatggcc cttatgggta gggcttccca cgtctcacaa    600
tggtcggtac agaggggtc ccagccccg aggggagcc aatcccaaa gccgatcgta      660 gtccggatgg tagtttgcaa ctcgcctacg tgaagtcgga atcgtttgta attgcagatc   720
accatggtgc ggggaatacc ttcccgggtt tggtacccc cgccctccc cccatggggg   780 ggggtttccc cggaagtagg aagcttaccc ttcggggggg gggt                     824
```

<210> SEQ ID NO 86
<211> LENGTH: 827
<212> TYPE: DNA
<213> ORGANISM: unknown
<220> FEATURE:
<223> OTHER INFORMATION: Unknown clone from enriched environmental
      sample that by rDNA sequence analysis has highest identity to
      Azoarcus sp. EH36

```
<400> SEQUENCE: 86
tatggaagag agtcggttag tgcgtggagg agctgcgtat gtatctactt ctctccgctc        60
tcctctctgc atgcgtgtca gacagccaga gggggcgggg tccccatcca tcgttgtctt       120
actttatgca ttaatgatac aacaggagta aacccccctc ttctgtatat agcatcgcag       180
tagcaacaac agctgttggg tggagcaggg gatgatttat catatgtcta aaacagcccg       240
cgcgcacgct ttatgcacag tatttgattg aaactcgcac cccctgtat atccccgggg        300 tgccgcacac atagttaggg ggtgtttttt tttccggcac ccccaccccg cgcgtgttag       360
agagaccgtg atttttttg gcggagagag agctttataa accgaagggt tttcactcac        420
ccgcggcagg gggggatcag gcttgcgccc cttttcaaaa aattcccccc ggcccccccc       480 cgagggggg tggggccgtt tttcagtccc cagggggggg gggtatcctc ttttcacccc        540
cccggattgt tgtggagggg ggggtttca ccccacggaa agatacaaac ccattaagcg        600
ctccaatcgc gggaggtcgg aagatccccc gcttttccc tcaggaggtt tggggtatta        660
gggtaccttt cgatacgttt tcccccccgc cagggcacg tttcgagcca ttattcaccc        720
gtttgcccct tgccggcagg ccgaagcccc ccctcccttt ggaatggcat ttgtaaagca       780
tgcccccagg gttcaatttg agccaaaata aaacttaaag gggaat                     827

<210> SEQ ID NO 87
<211> LENGTH: 349
<212> TYPE: DNA
<213> ORGANISM: unknown
<220> FEATURE:
<223> OTHER INFORMATION: Unknown clone from enriched environmental
      sample that by rDNA sequence analysis has highest identity to
      FLexistipes sp. vp180

<400> SEQUENCE: 87
ctattgtcag ttgccatcaa gtaaggtggg cactgtaaag agtccgctgg ggataacccg        60
gaggaaggtg gggacgatgt caagtcatca tggtcgtgat gtacagggtt acgcacctga      120
tacaatggtg catacagagg gcagtgagac accgacgtta agagaatacg ttaaagtgca       180
cctcacttcg gaatgcagta tgcaaatcga atgcatggtg ttggaattgt tagtaattgc       240
aggtcagcaa tagtggggtg attacgttcc cgggcatggt acacaccgcc agtcacacca      300
tgggagtcgg ttgtacatga agccggtggc ccaaccgcaa gggggagc                   349
```